(12) United States Patent
Lee et al.

(10) Patent No.: US 10,918,727 B2
(45) Date of Patent: Feb. 16, 2021

(54) PEPTIDE WITH ABILITY TO PENETRATE CELL MEMBRANE

(71) Applicant: ICURE BNP CO., LTD., Eumseong-gun (KR)

(72) Inventors: Kyung Lim Lee, Seoul (KR); Hea Duk Bae, Seoul (KR); Jee Hye Maeng, Seoul (KR)

(73) Assignee: ICURE BNP CO., LTD., Eumseong-Gun (KR)

( * ) Notice: Subject to any disclaimer, the term of this patent is extended or adjusted under 35 U.S.C. 154(b) by 0 days.

(21) Appl. No.: 16/092,190

(22) PCT Filed: Apr. 6, 2017

(86) PCT No.: PCT/KR2017/003790
§ 371 (c)(1),
(2) Date: Oct. 8, 2018

(87) PCT Pub. No.: WO2017/176076
PCT Pub. Date: Oct. 12, 2017

(65) Prior Publication Data
US 2019/0111141 A1    Apr. 18, 2019

(30) Foreign Application Priority Data

| Apr. 6, 2016 | (KR) | 10-2016-0042530 |
|---|---|---|
| Apr. 6, 2016 | (KR) | 10-2016-0042531 |
| Apr. 6, 2016 | (KR) | 10-2016-0042533 |
| Apr. 6, 2017 | (KR) | 10-2017-0044845 |

(51) Int. Cl.

| A61K 47/42 | (2017.01) |
|---|---|
| A61K 47/64 | (2017.01) |
| C07K 7/06 | (2006.01) |
| C07K 7/08 | (2006.01) |
| A61P 3/04 | (2006.01) |
| A61P 3/10 | (2006.01) |
| A61K 38/26 | (2006.01) |
| A61K 38/28 | (2006.01) |
| A61K 47/34 | (2017.01) |
| A61K 38/00 | (2006.01) |
| A61K 47/18 | (2017.01) |
| A61K 9/00 | (2006.01) |
| A61K 47/10 | (2017.01) |
| A61K 47/20 | (2006.01) |
| A61K 47/26 | (2006.01) |

(52) U.S. Cl.
CPC .............. *A61K 47/42* (2013.01); *A61K 38/26* (2013.01); *A61K 38/28* (2013.01); *A61K 47/34* (2013.01); *A61K 47/64* (2017.08); *A61P 3/04* (2018.01); *A61P 3/10* (2018.01); *C07K 7/06* (2013.01); *C07K 7/08* (2013.01); A61K 9/0014 (2013.01); *A61K 9/0019* (2013.01); *A61K 9/0043* (2013.01); *A61K 38/00* (2013.01); *A61K 47/10* (2013.01); *A61K 47/18* (2013.01); *A61K 47/20* (2013.01); *A61K 47/26* (2013.01)

(58) Field of Classification Search
None
See application file for complete search history.

(56) References Cited

U.S. PATENT DOCUMENTS

| 9,907,857 B2 * | 3/2018 | Lee | C07K 14/46 |
|---|---|---|---|
| 2013/0129726 A1 * | 5/2013 | Lee | C07K 7/06 424/134.1 |
| 2013/0136742 A1 | 5/2013 | Lee et al. | |
| 2016/0324976 A1 * | 11/2016 | Lee | A61K 48/0008 |

FOREIGN PATENT DOCUMENTS

| JP | 2009-527251 A | 7/2009 |
|---|---|---|
| JP | 2015-508993 A | 3/2015 |
| KR | 10-2007-0117551 A | 12/2007 |
| KR | 10-1258279 | 4/2013 |
| KR | 10-2014-0098954 | 8/2014 |
| KR | 10-2015-0130249 | 11/2015 |
| KR | 10-0859972 | 9/2018 |
| WO | WO 2007/097561 A1 | 8/2007 |
| WO | WO 2014/086835 A1 | 6/2014 |

OTHER PUBLICATIONS

Bae et al., "On employing a translationally controlled tumor protein-derived protein transduction domain analog for transmucosal delivery of drugs," *Journal of Controlled Release* 170(3): 358-364 (Jun. 18, 2013).
Kim et al., "Cellular uptake mechanism of TCTP-PTD in human lung carcinoma," *Molecular Pharmaceutics* 12(1): 194-203 (2015).
(Continued)

*Primary Examiner* — Maury A Audet
(74) *Attorney, Agent, or Firm* — Sughrue Mion, PLLC

(57) ABSTRACT

Disclosed are a translationally controlled tumor protein derived-protein transduction domain (TCTP-PTD) having the ability to penetrate the cell membrane, and to the use thereof. The TCTP-PTD peptide is capable of improving the ability of a target substance to penetrate the cell membrane to thereby effectively deliver the target substance into a living body, including cells, tissue and blood. Thus, the TCTP-PTD peptide may be used for research purposes in vitro, and may be used for clinical purposes, including treatment of various diseases, delivery of contrast agents, etc., and may also be used for diagnostic purposes and in cosmetic applications.

25 Claims, 25 Drawing Sheets
Specification includes a Sequence Listing.

(56) References Cited

OTHER PUBLICATIONS

Jarver and Langel,"The use of cell-penetrating peptides as a tool for gene regulation." *Drug Discov. Today* vol. 9, pp. 395-402 (2004).
Lee, et al. "Neuroprotective effect of Cu,Zn-superoxide dismutase fused to a TCTP-derived protein transduction domain." *European Journal of Pharmacology* vol. 666, pp. 87-92 (2011).
Morris, et al. "A peptide carrier for the delivery of biologically active proteins into mammalian cells." *Nat. Biotechnol.* vol. 19, pp. 1173-1176 (2001).

* cited by examiner

[Fig. 1]
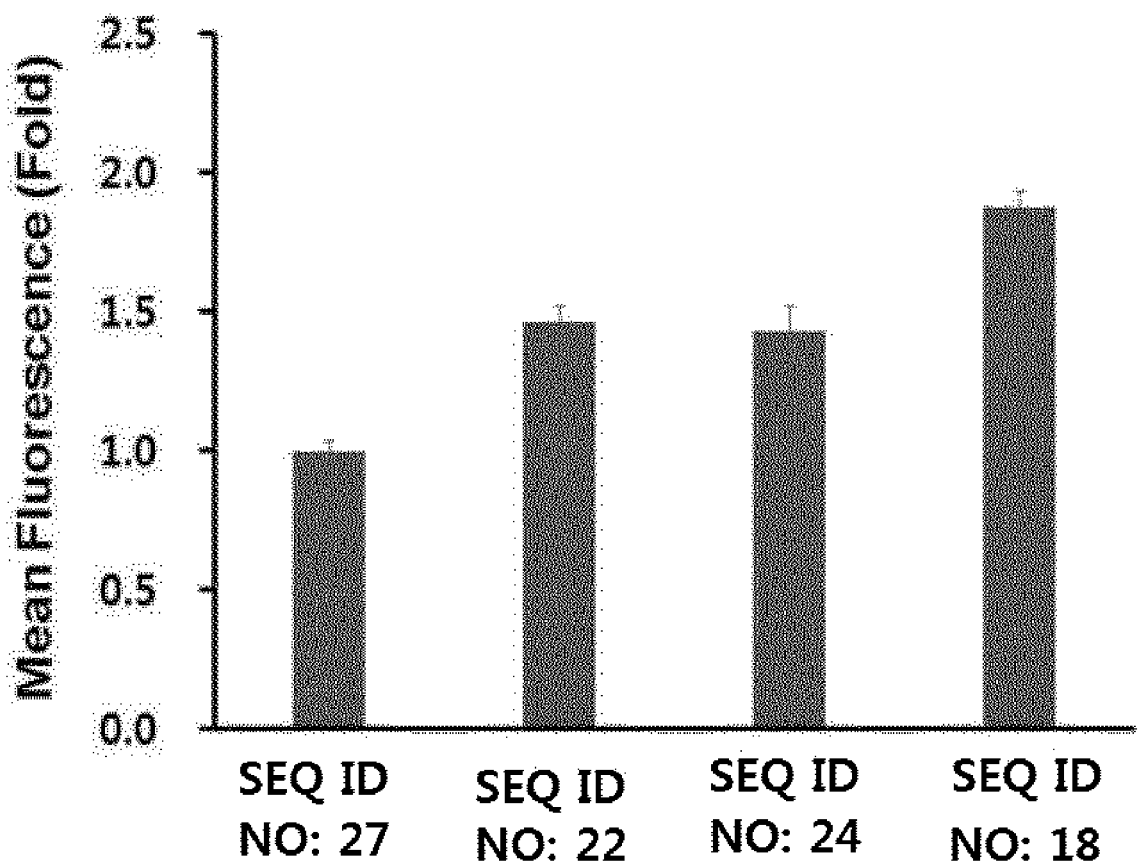

[Fig. 2]
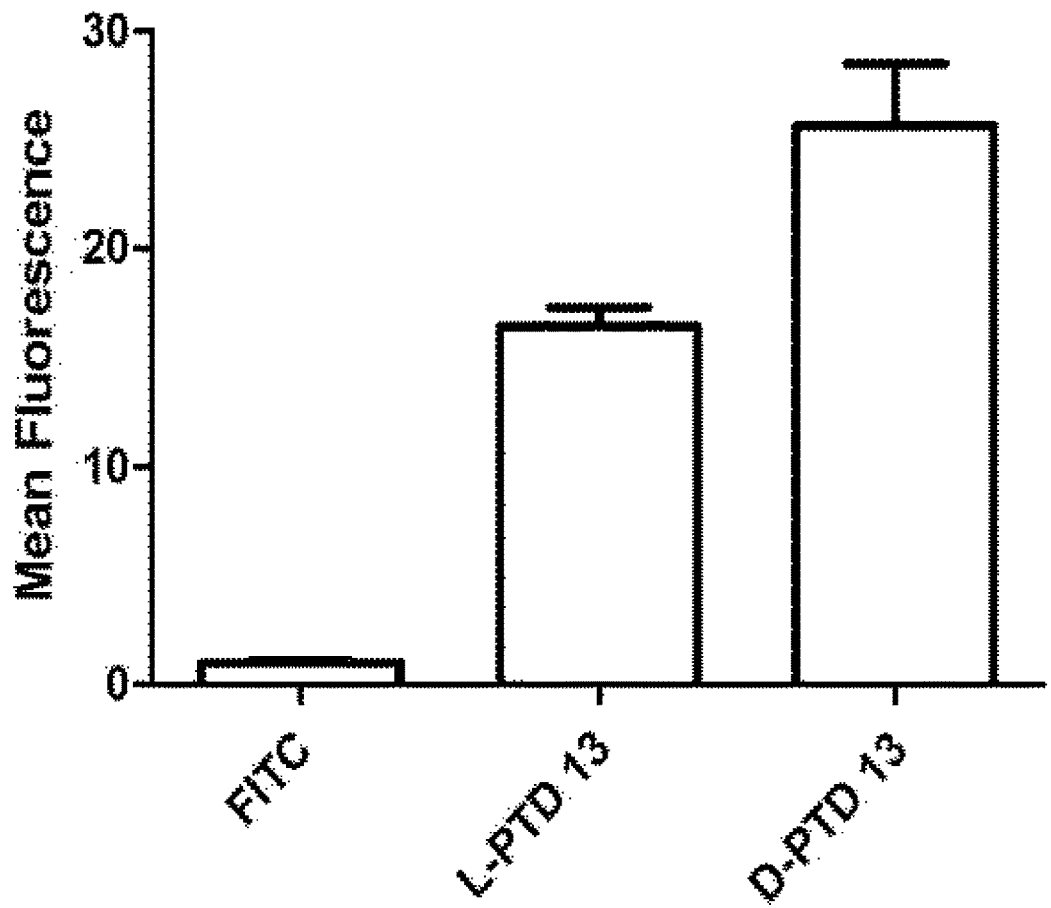
[Fig. 3]
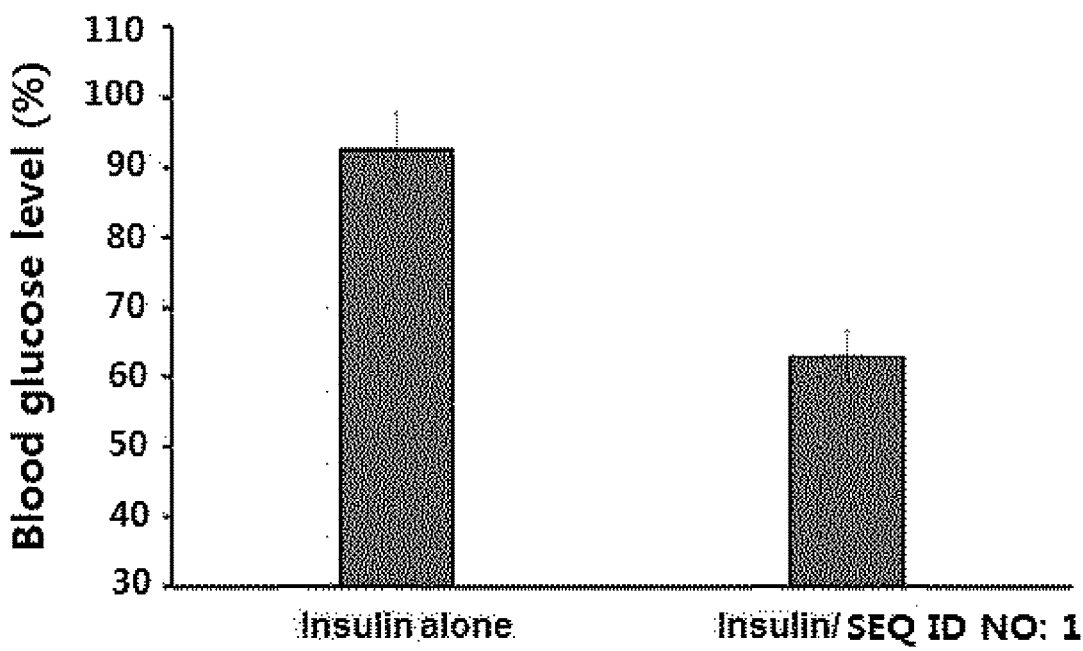

[Fig. 4]
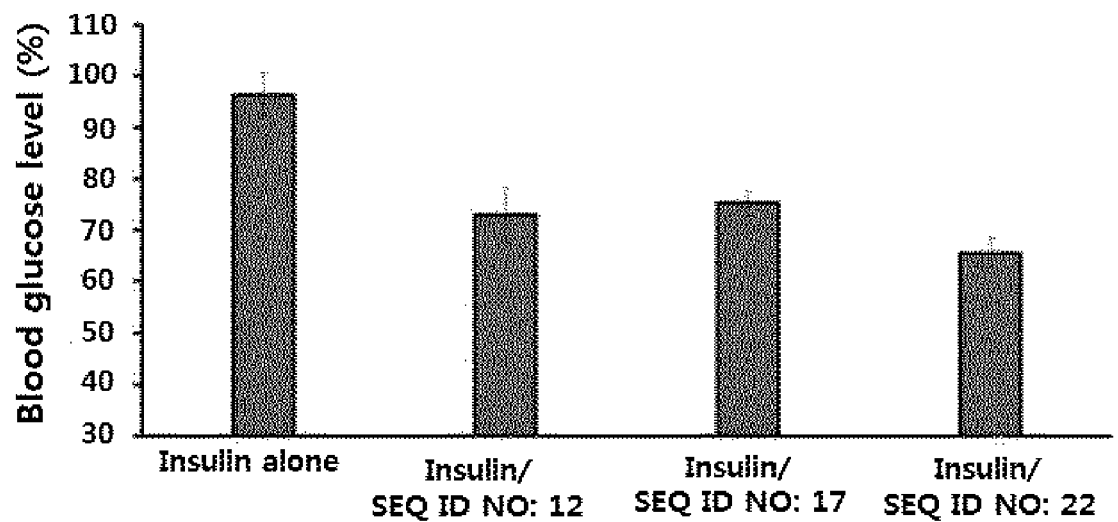
[Fig. 5]
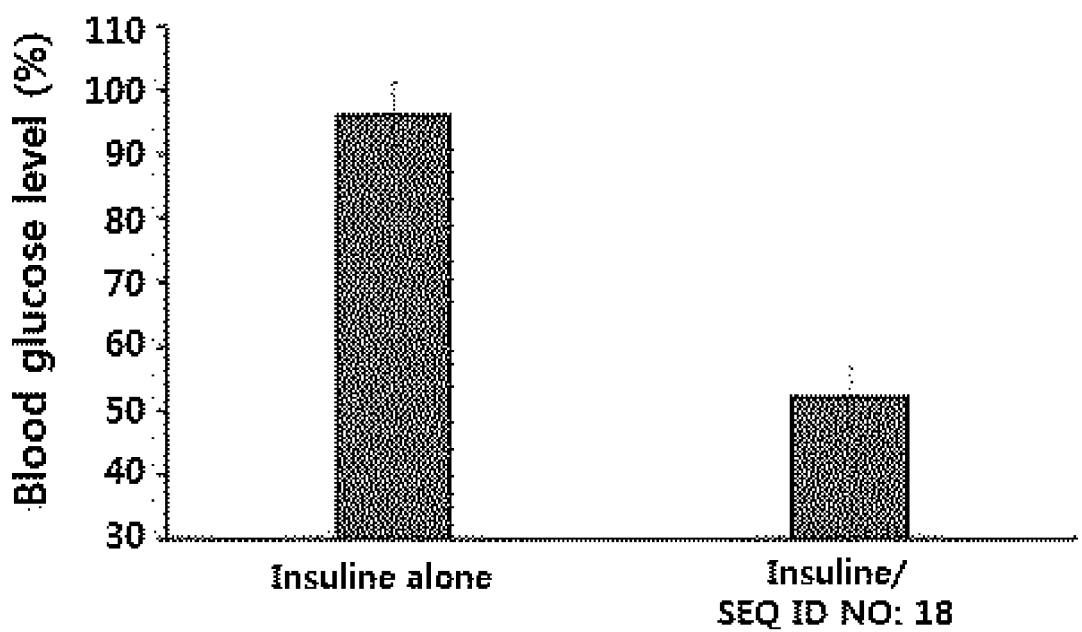

[Fig. 6]
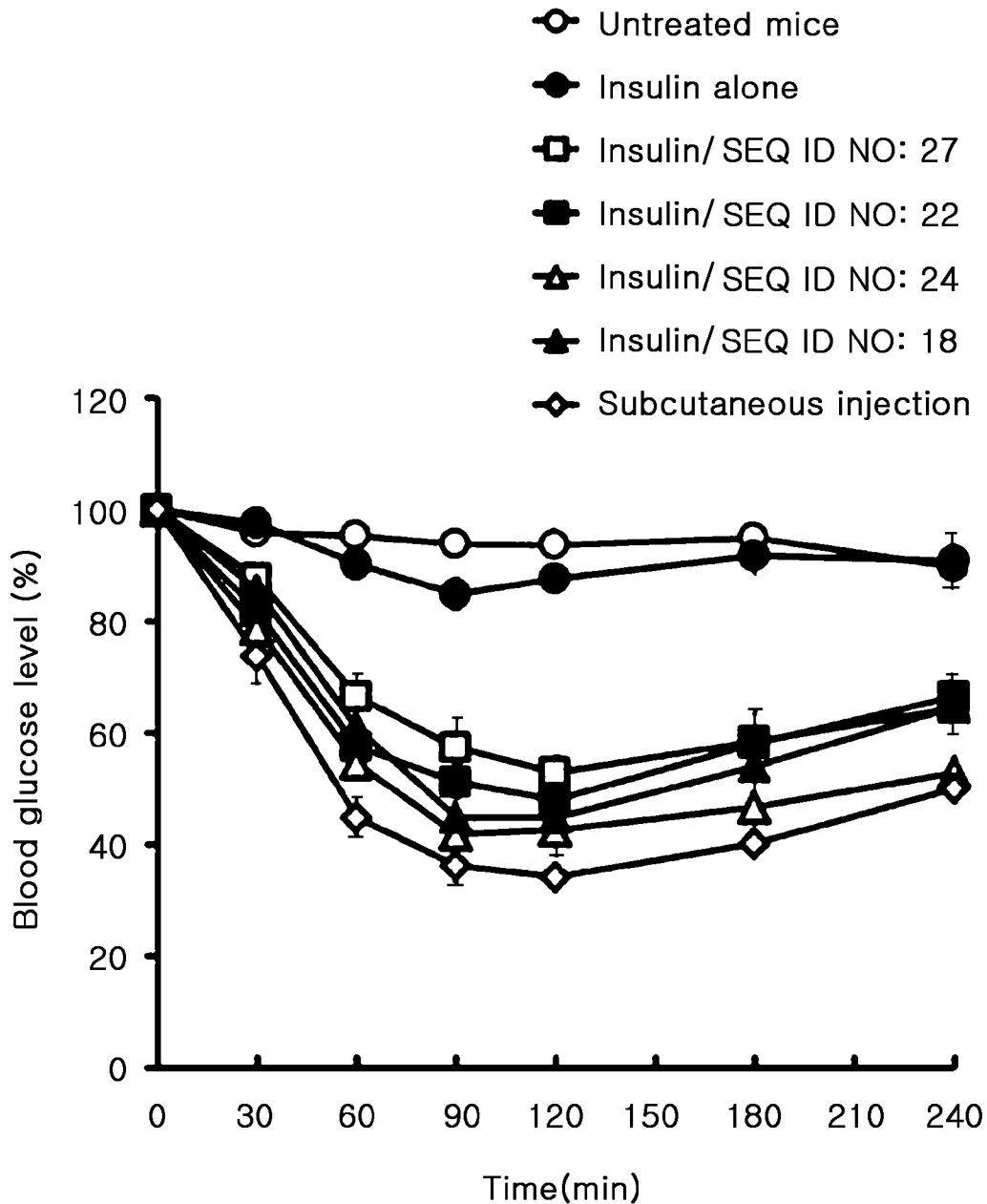

[Fig. 7]
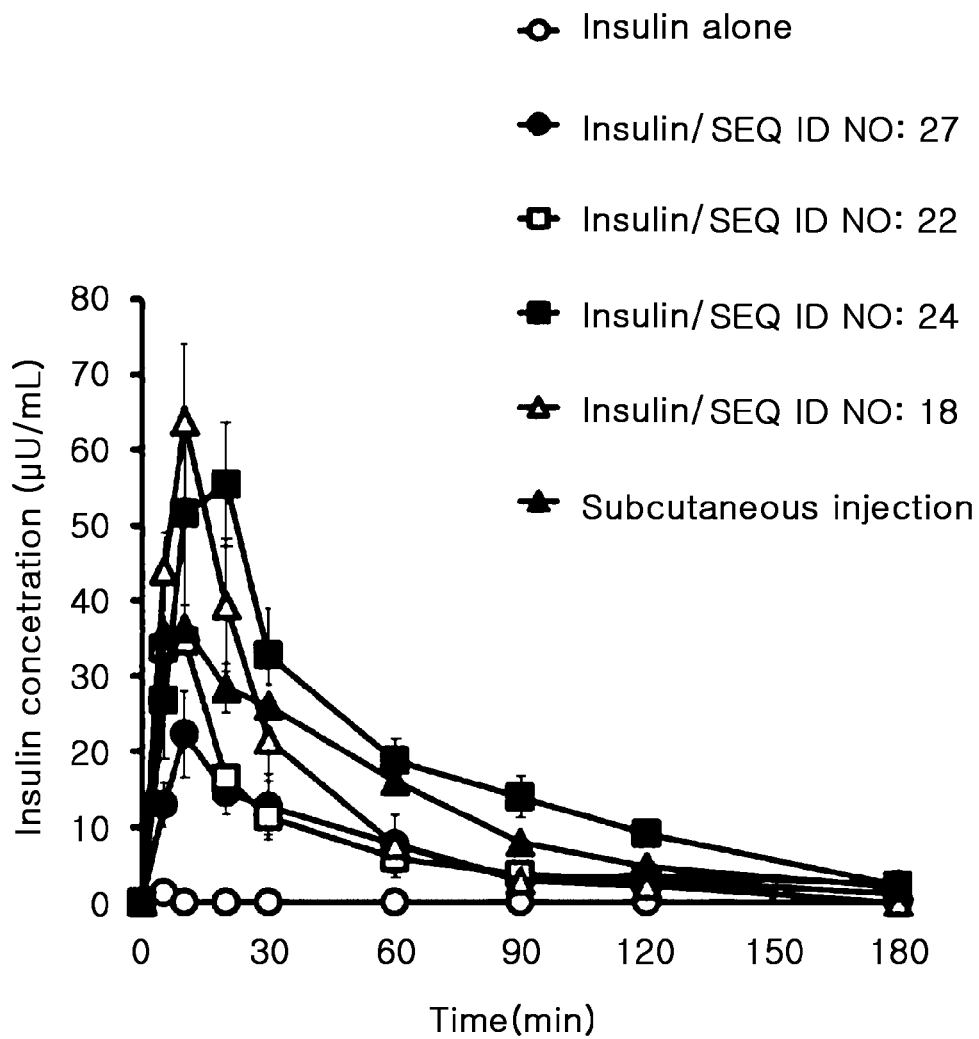

[Fig. 8]
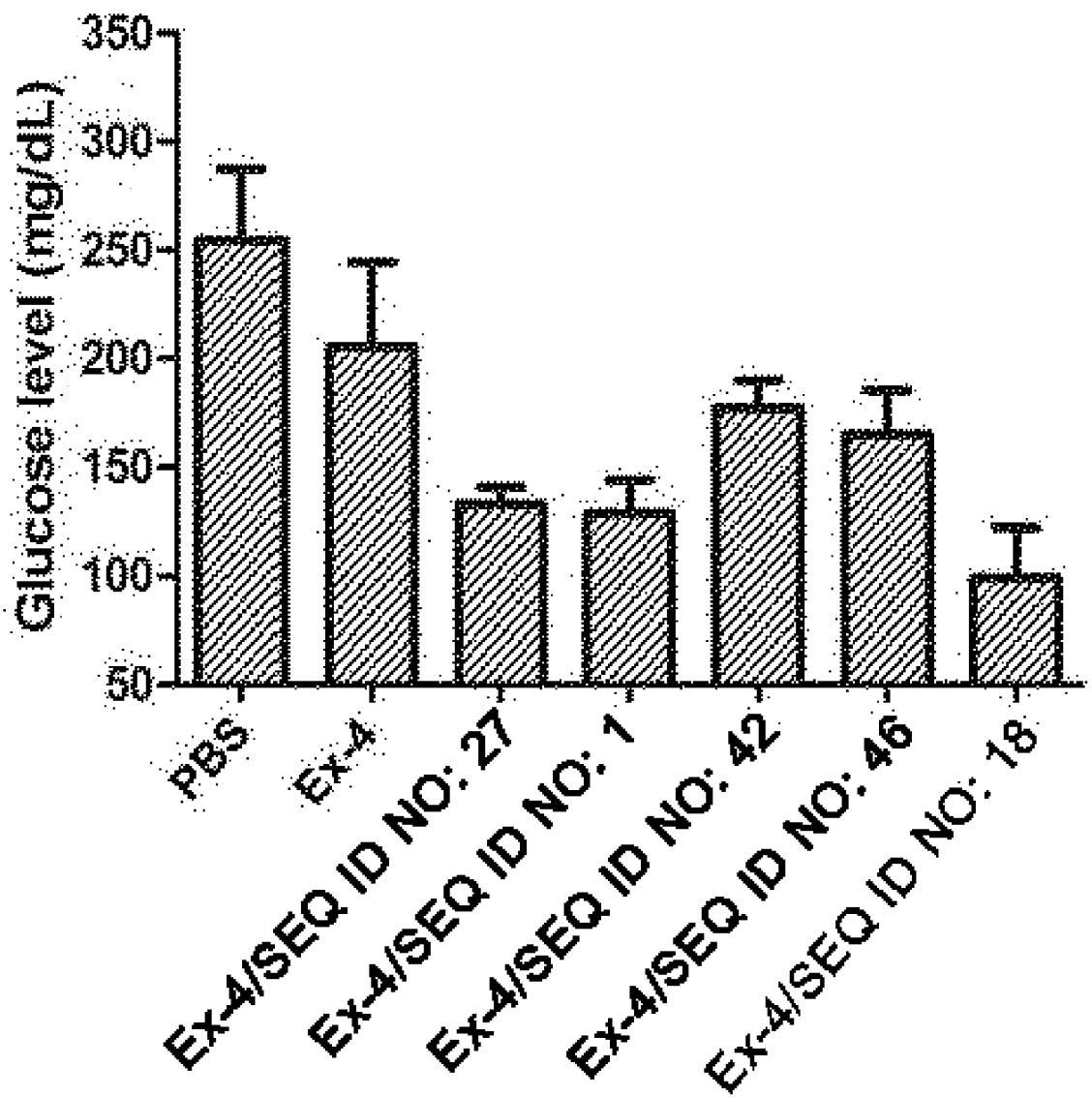

[Fig. 9]
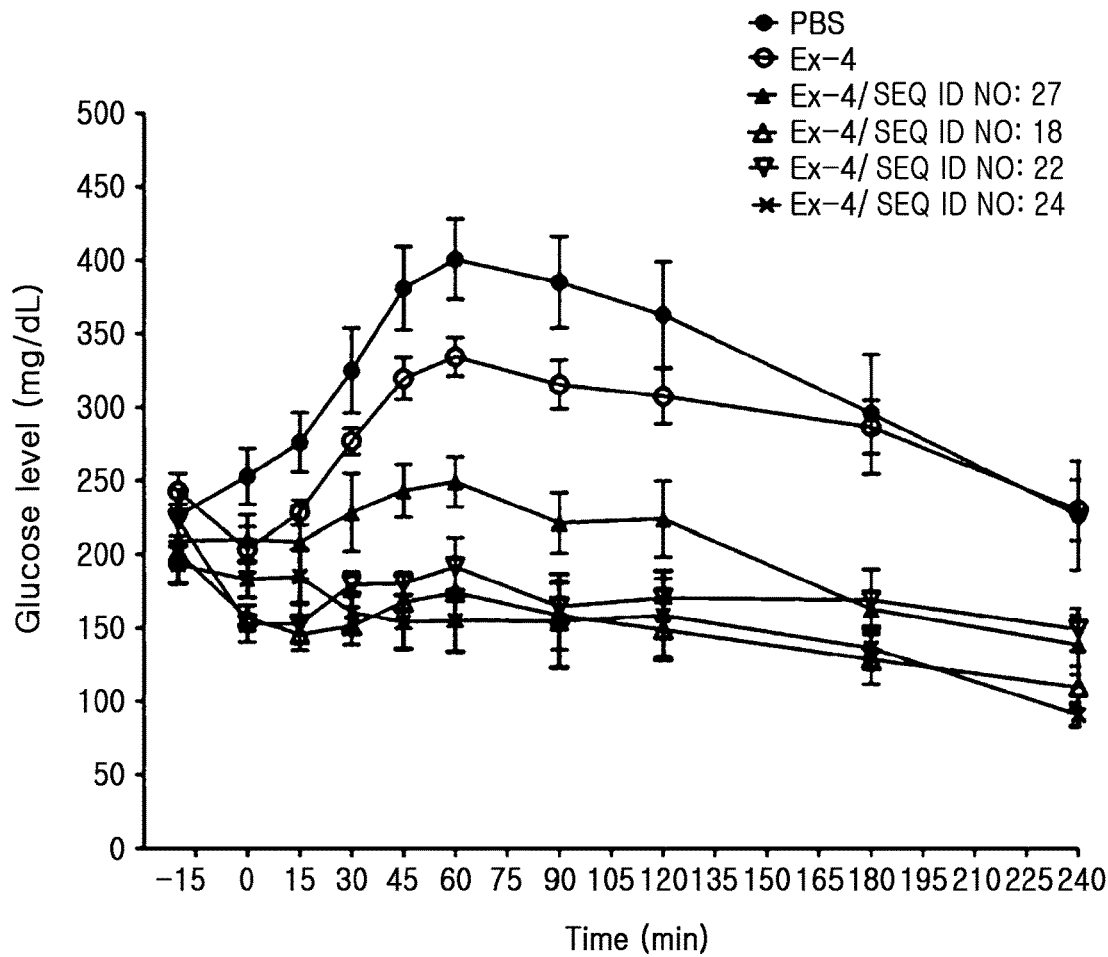
[Fig. 10]
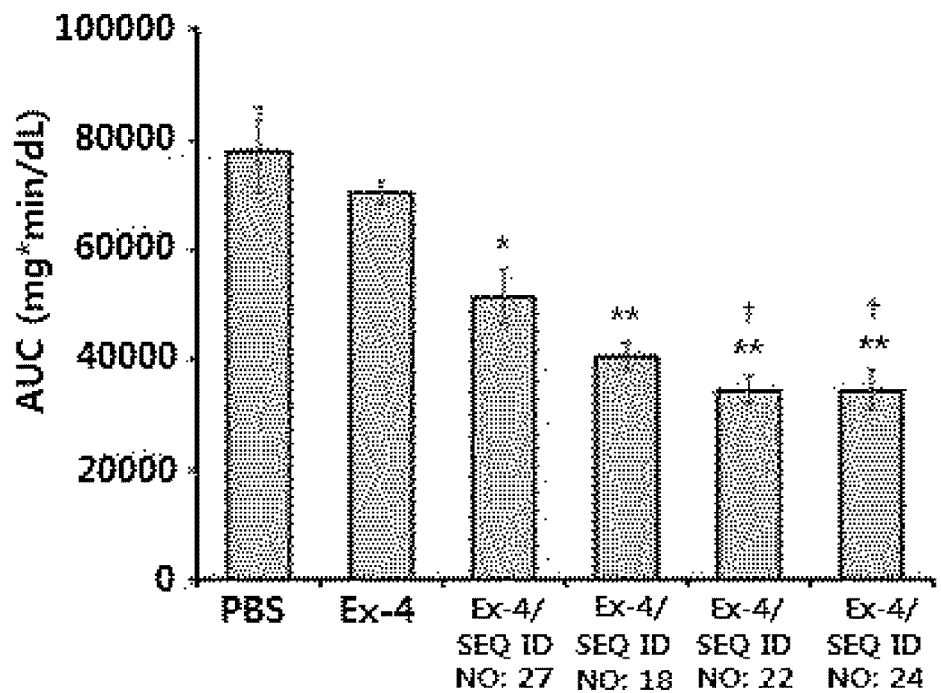

[Fig. 11]
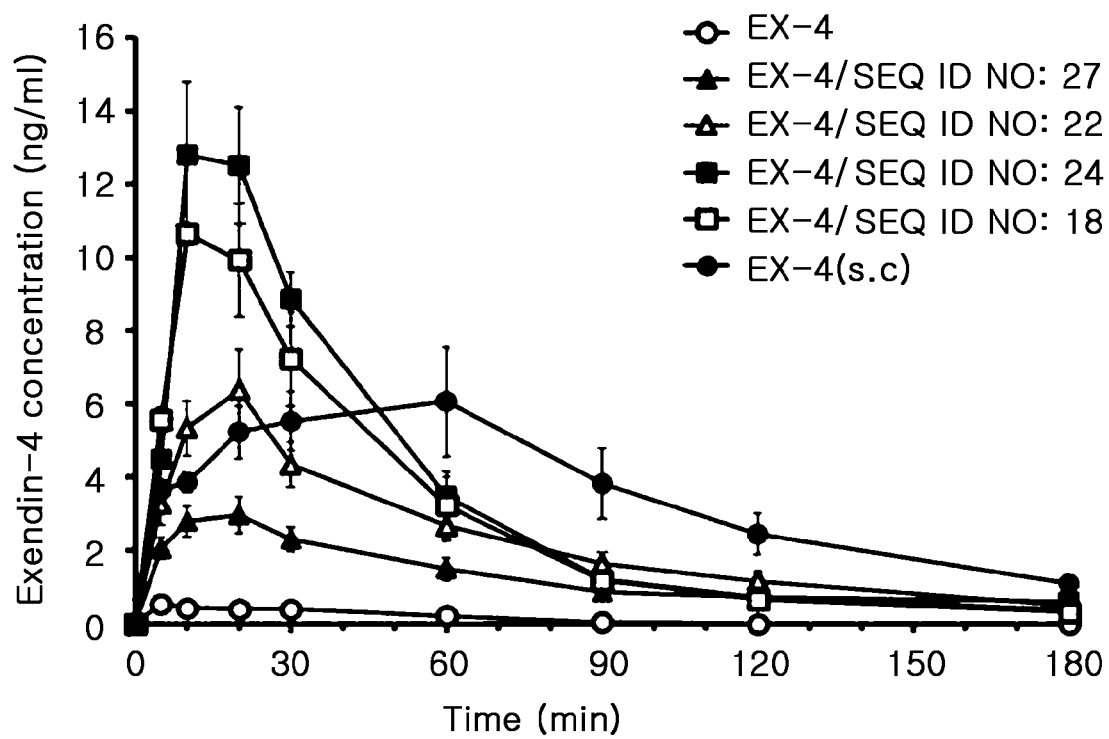

[Fig. 12]
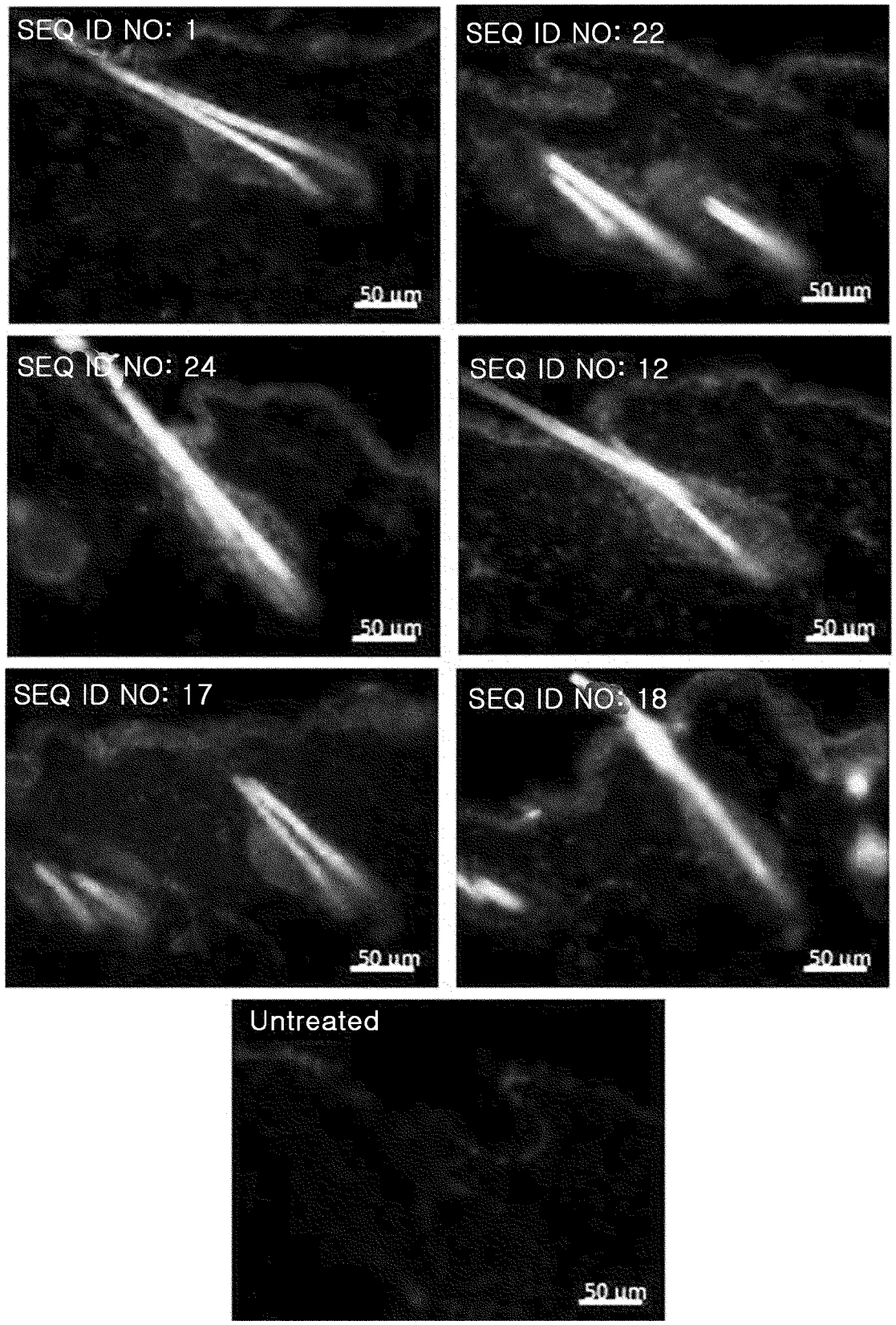

[Fig. 13]
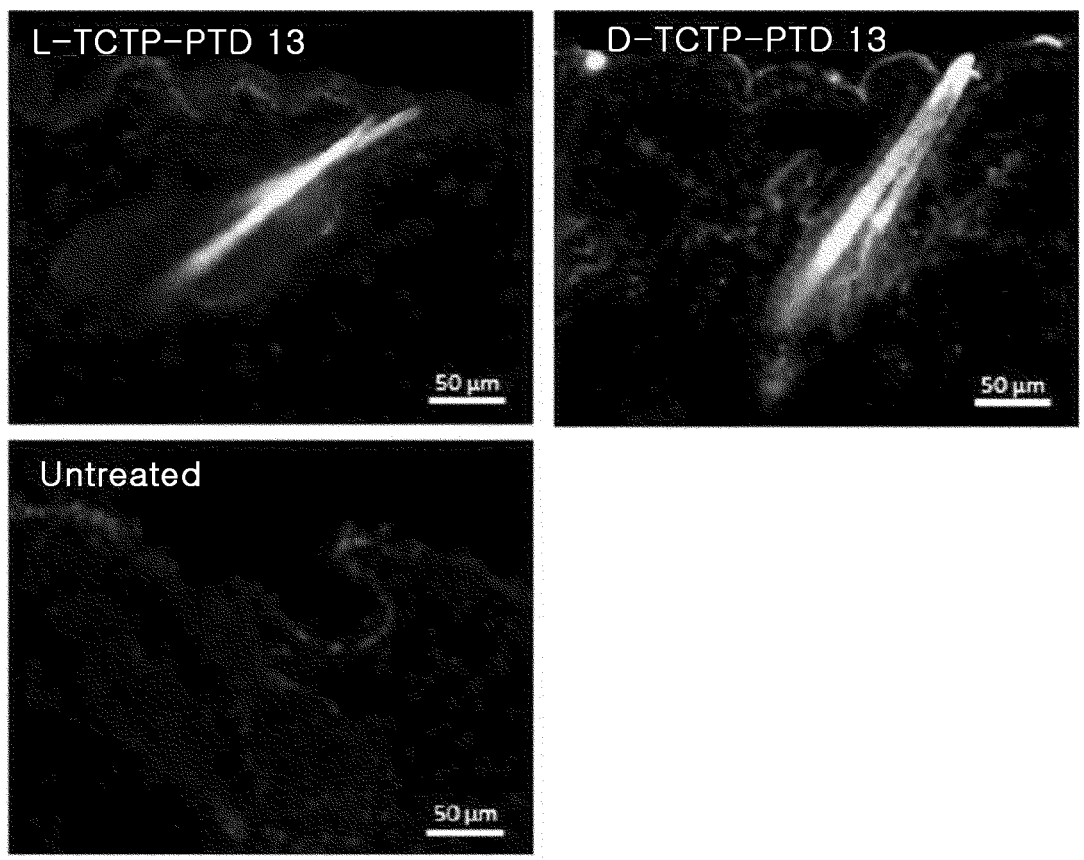

[Fig. 14]
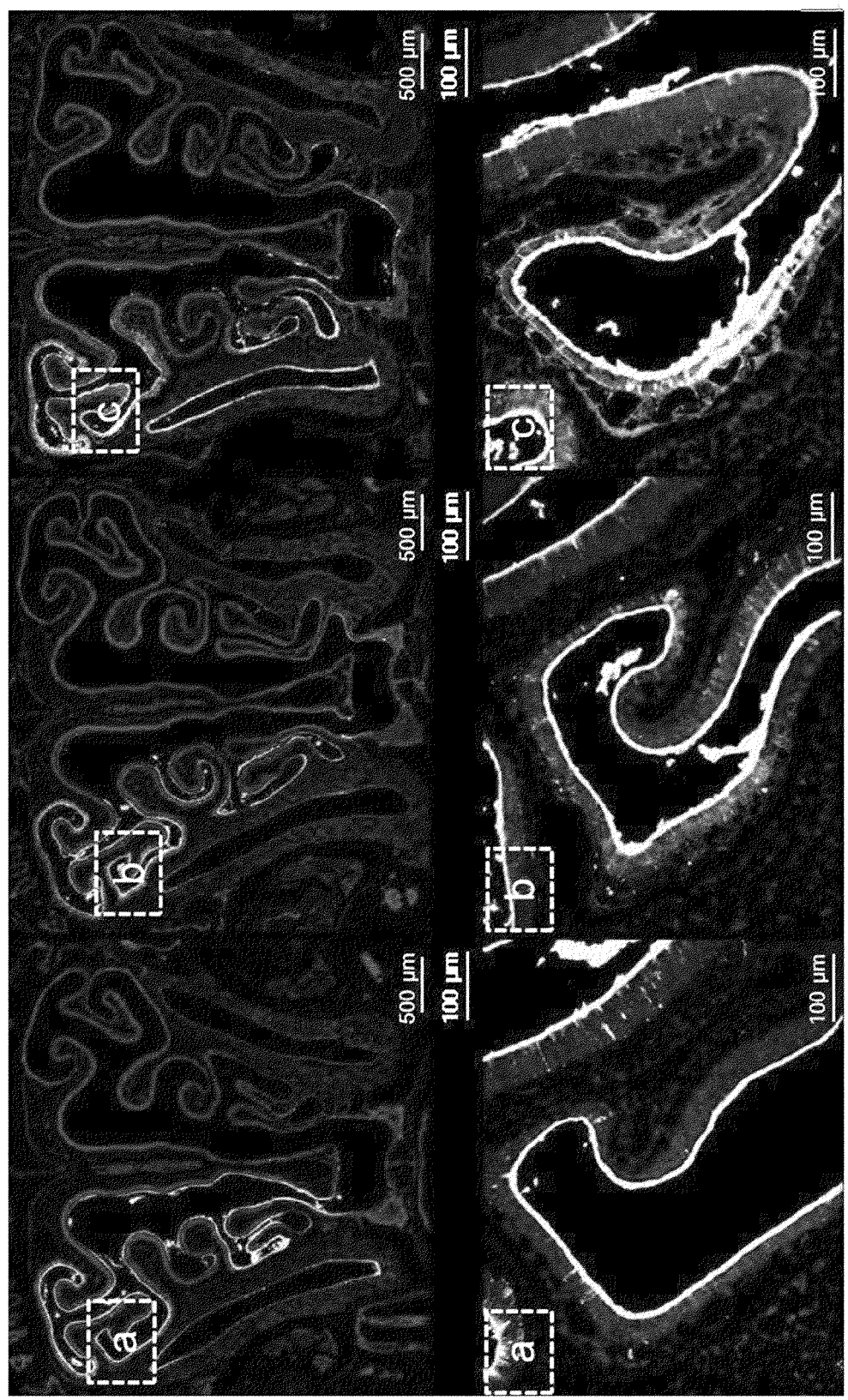

[Fig. 15]
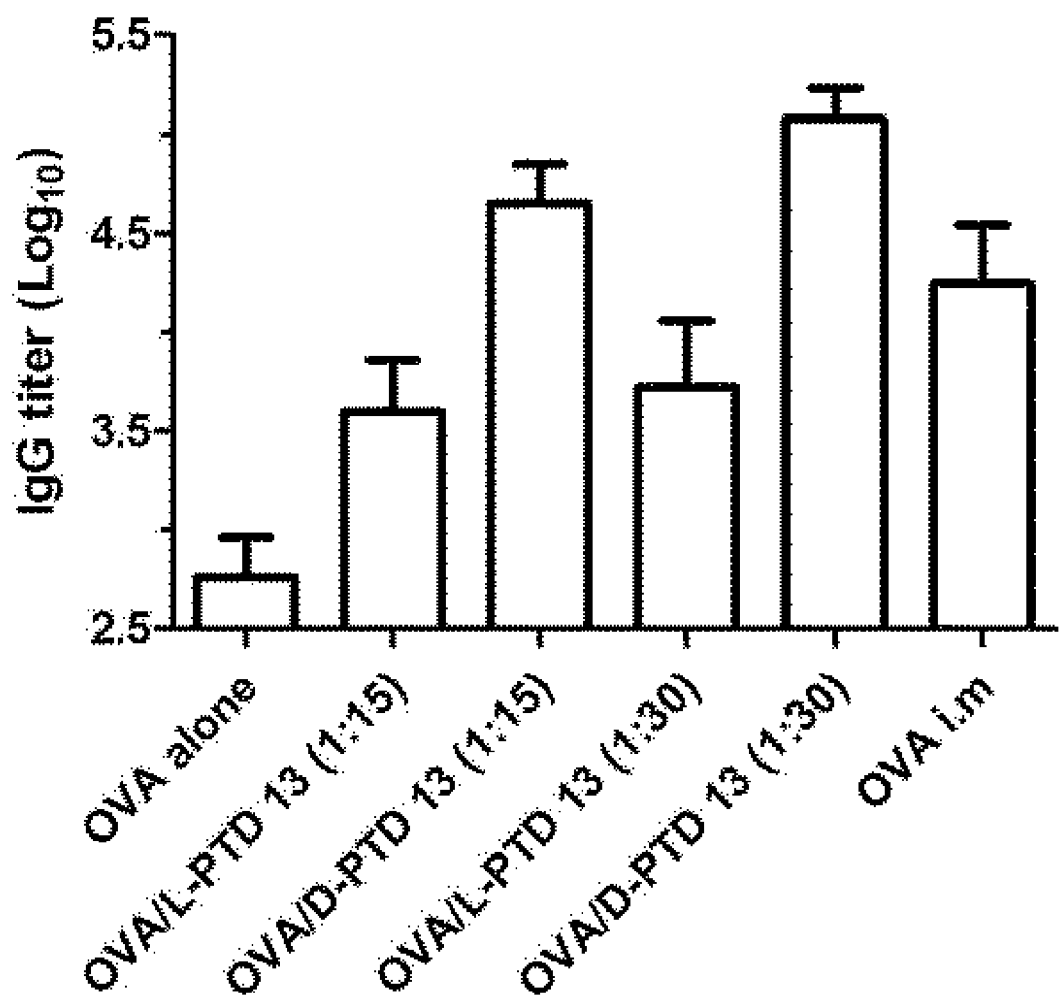

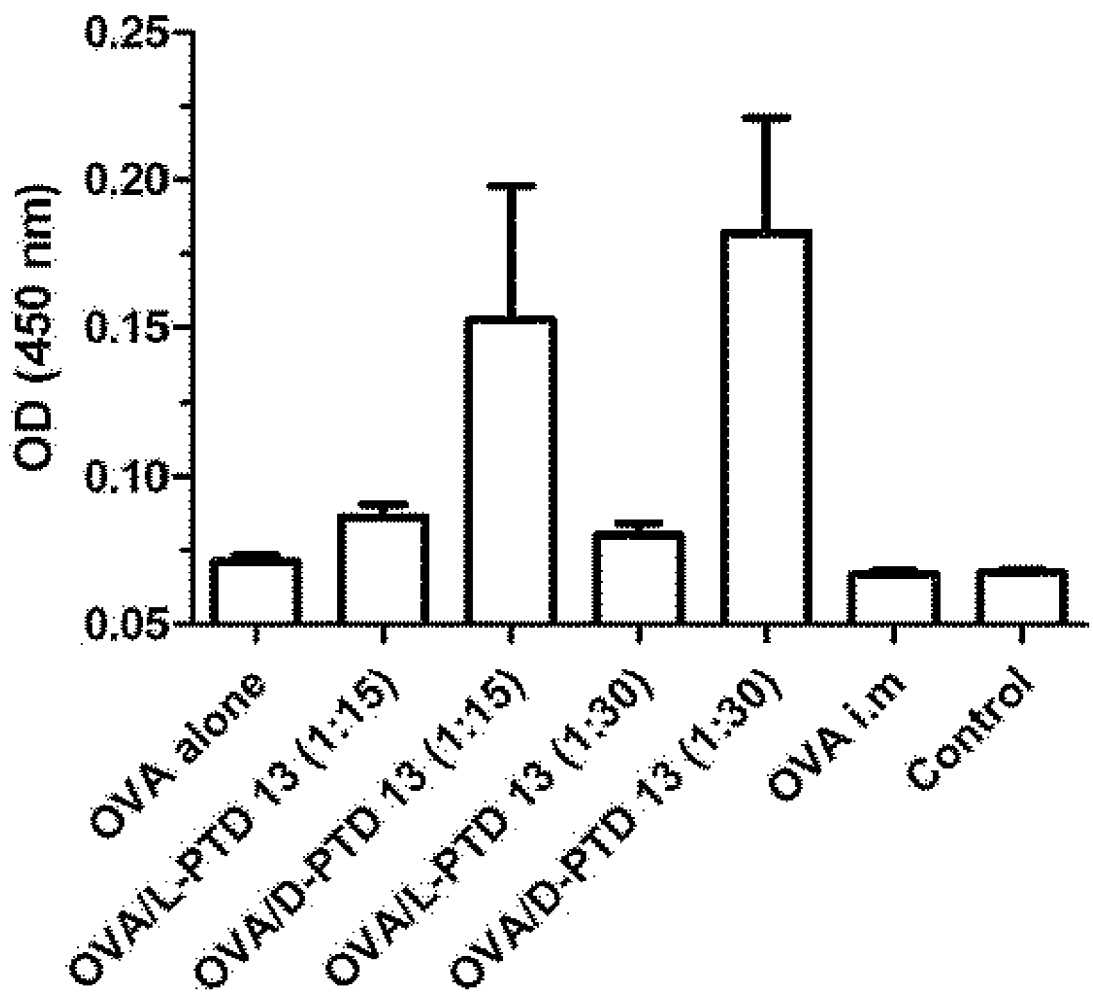
[Fig. 16]

[Fig. 17]
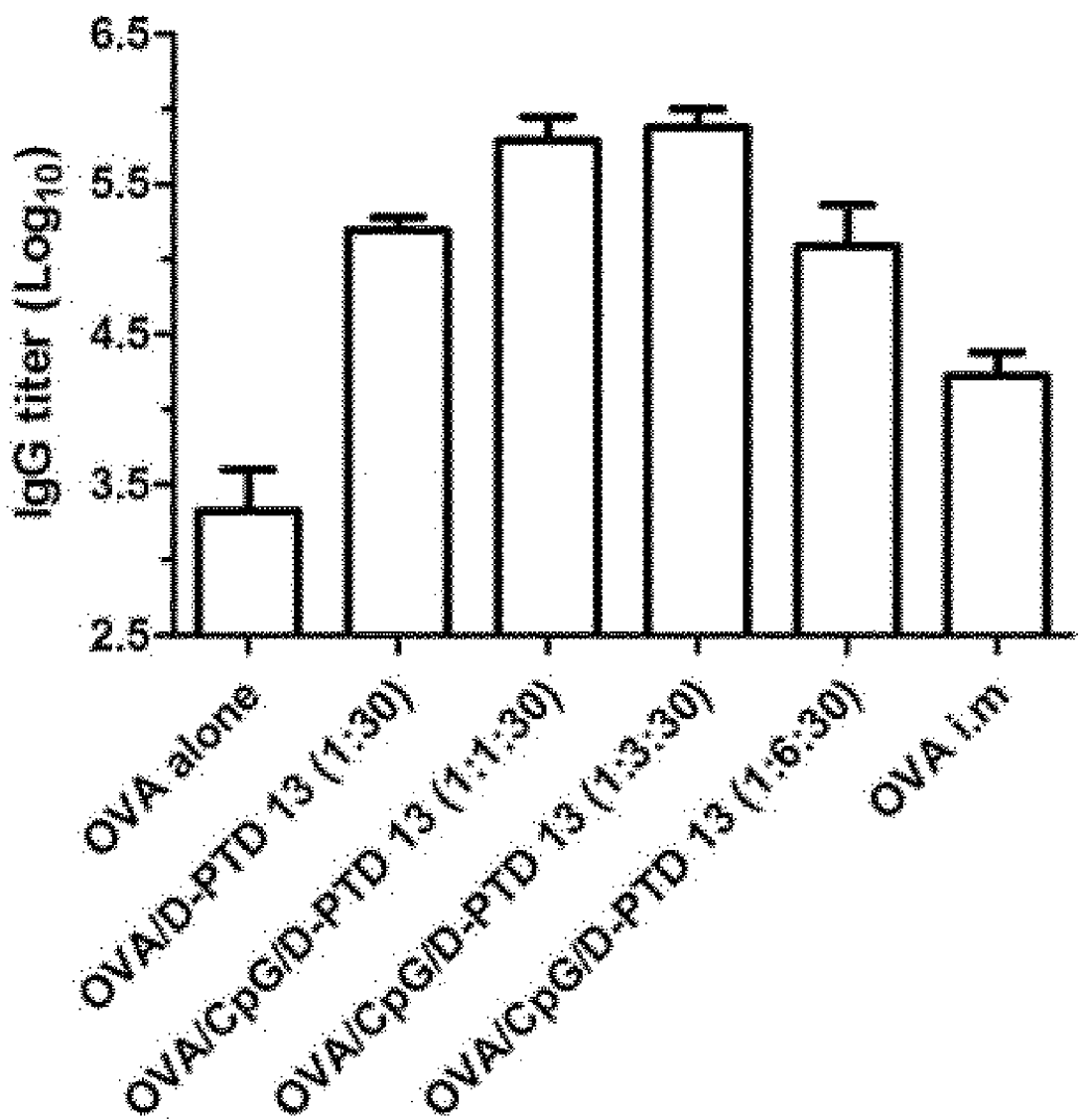

[Fig. 18]
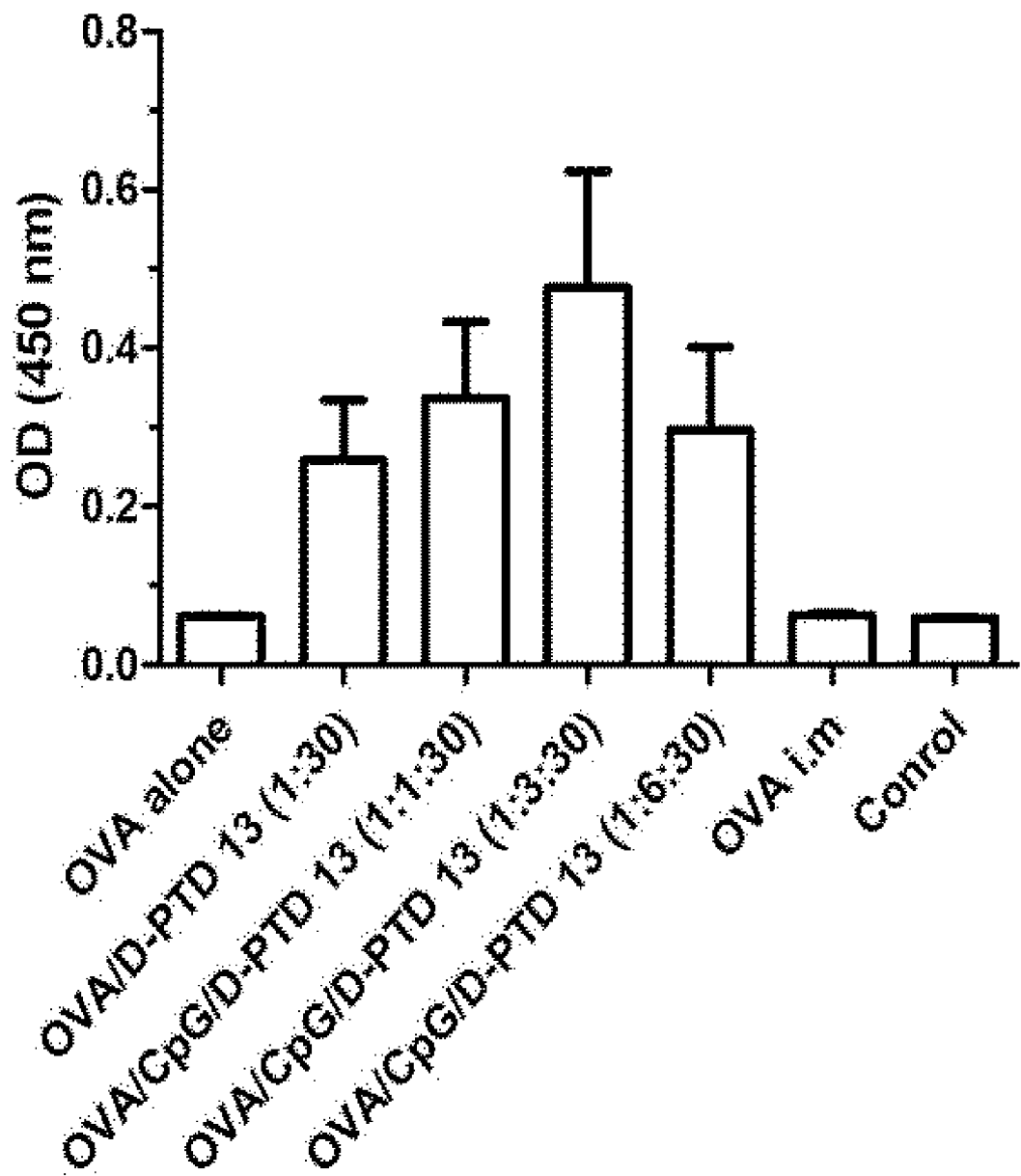

[Fig. 19]
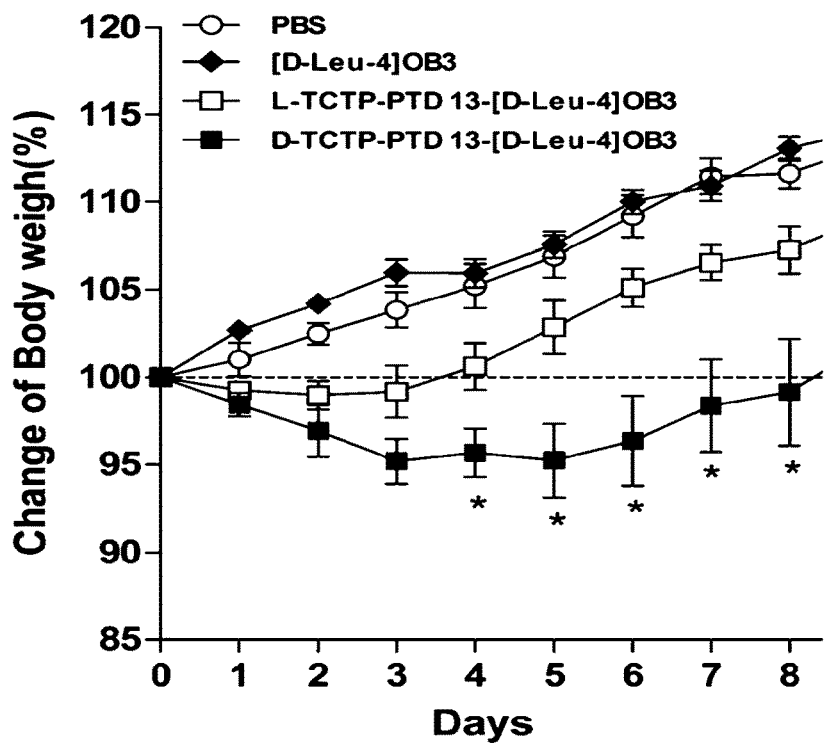
[Fig. 20]
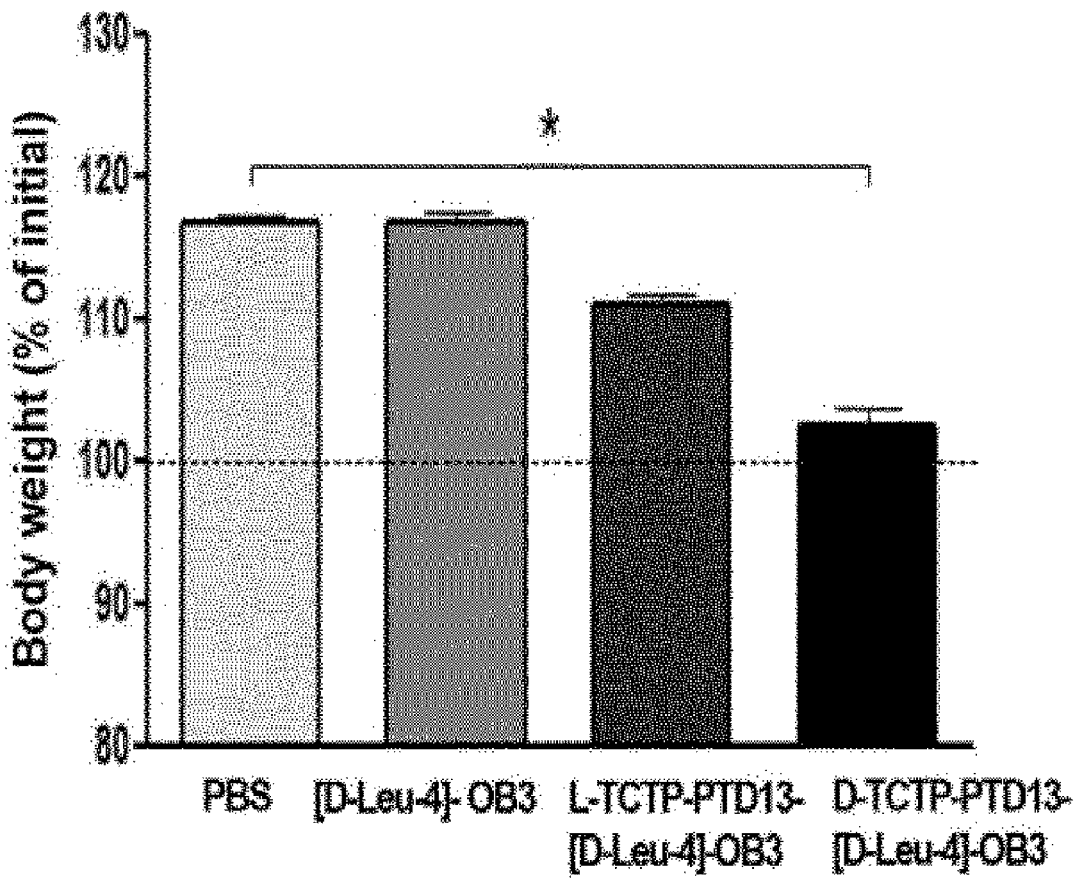

[Fig. 21]
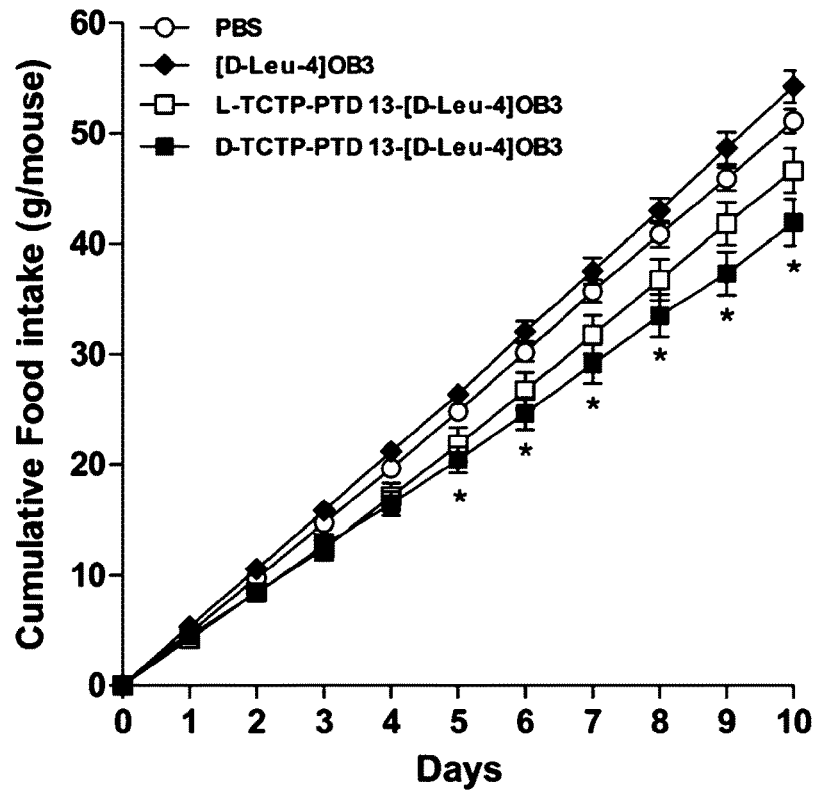
[Fig. 22]
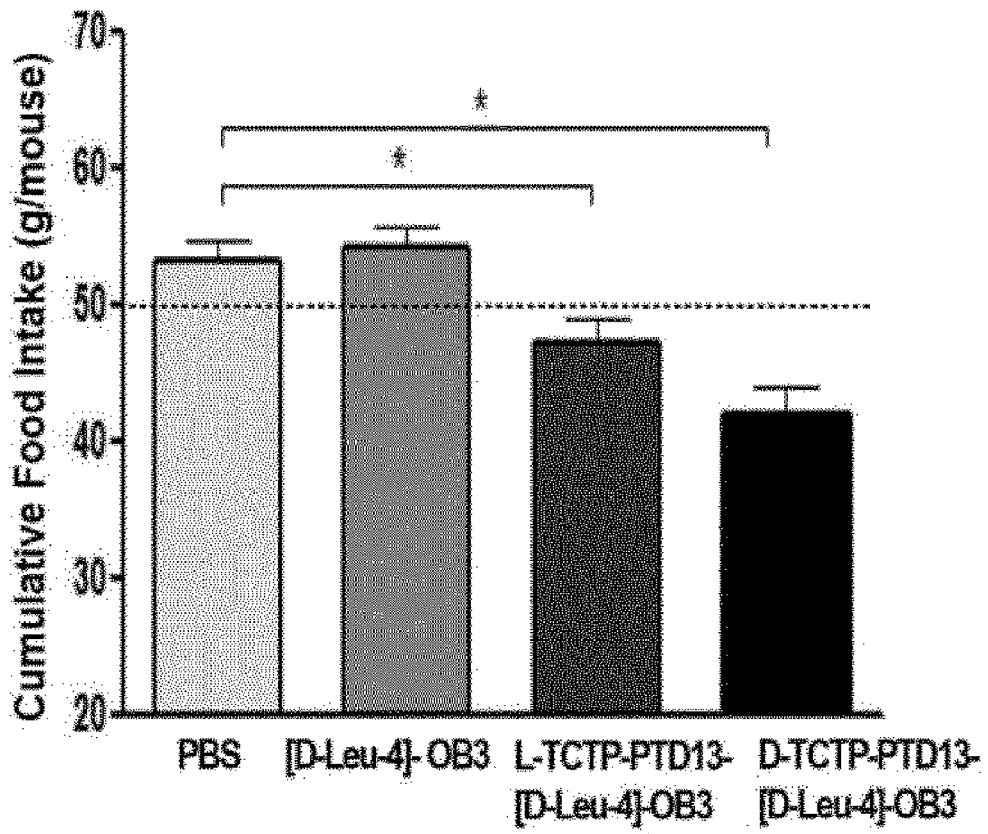

[Fig. 23]
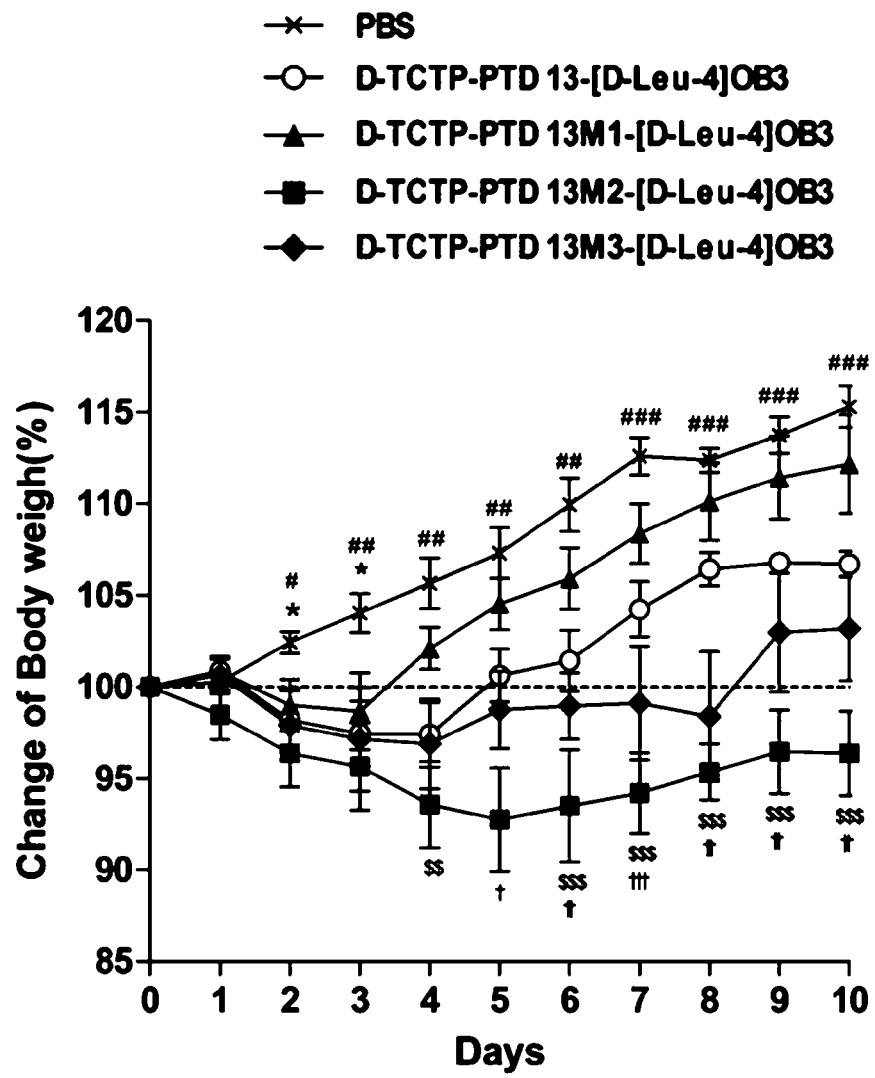

[Fig. 24]
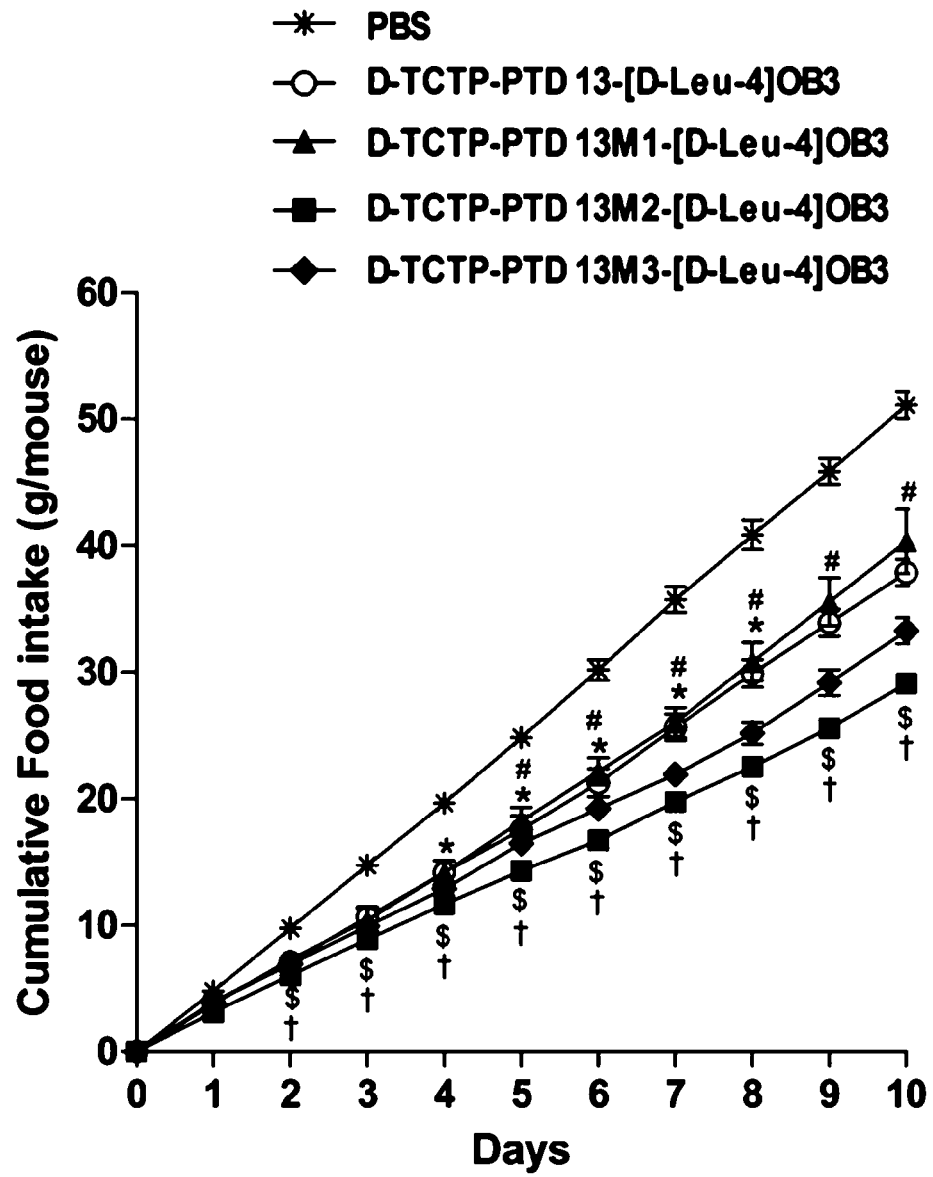

[Fig. 25]
(a)
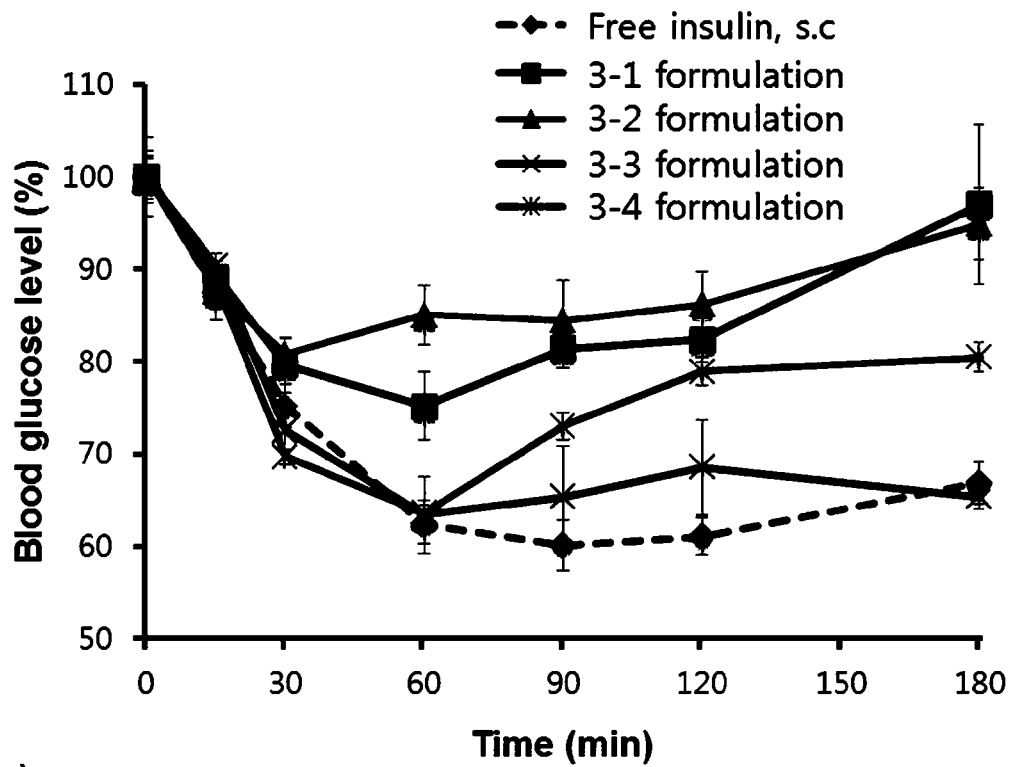
(b)
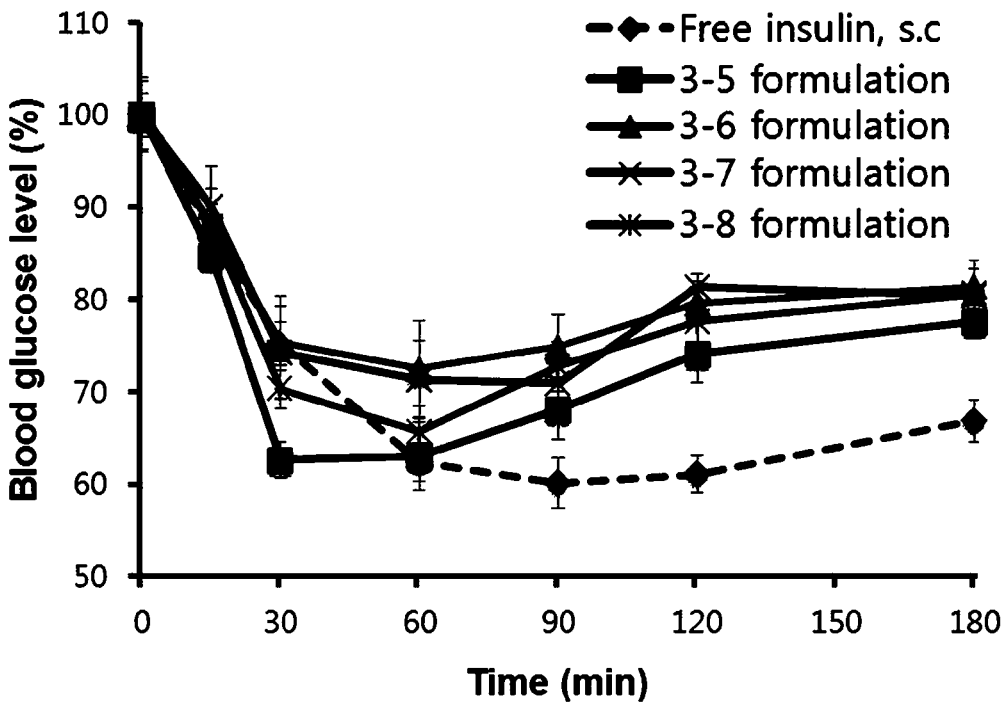

[Fig. 26]
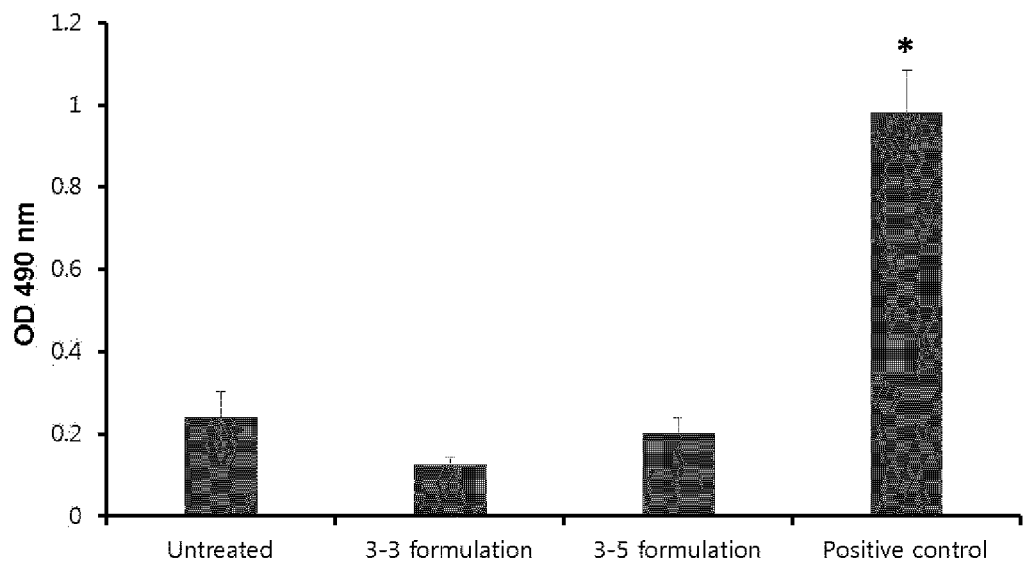
[Fig. 27]
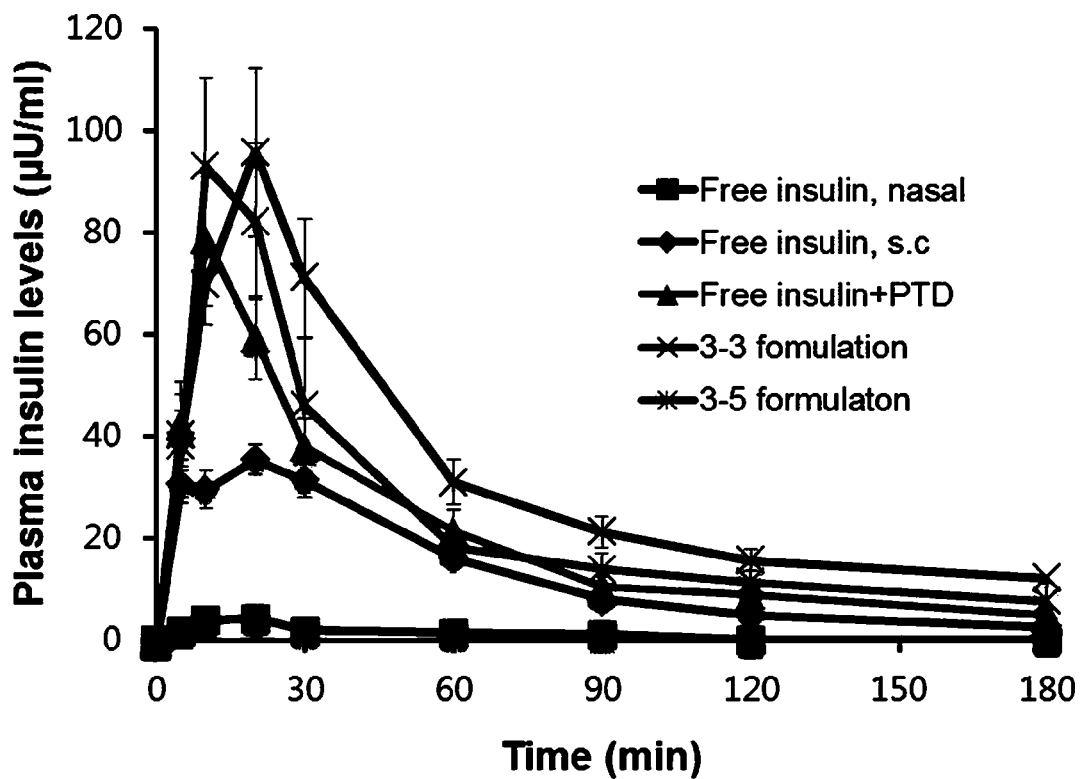

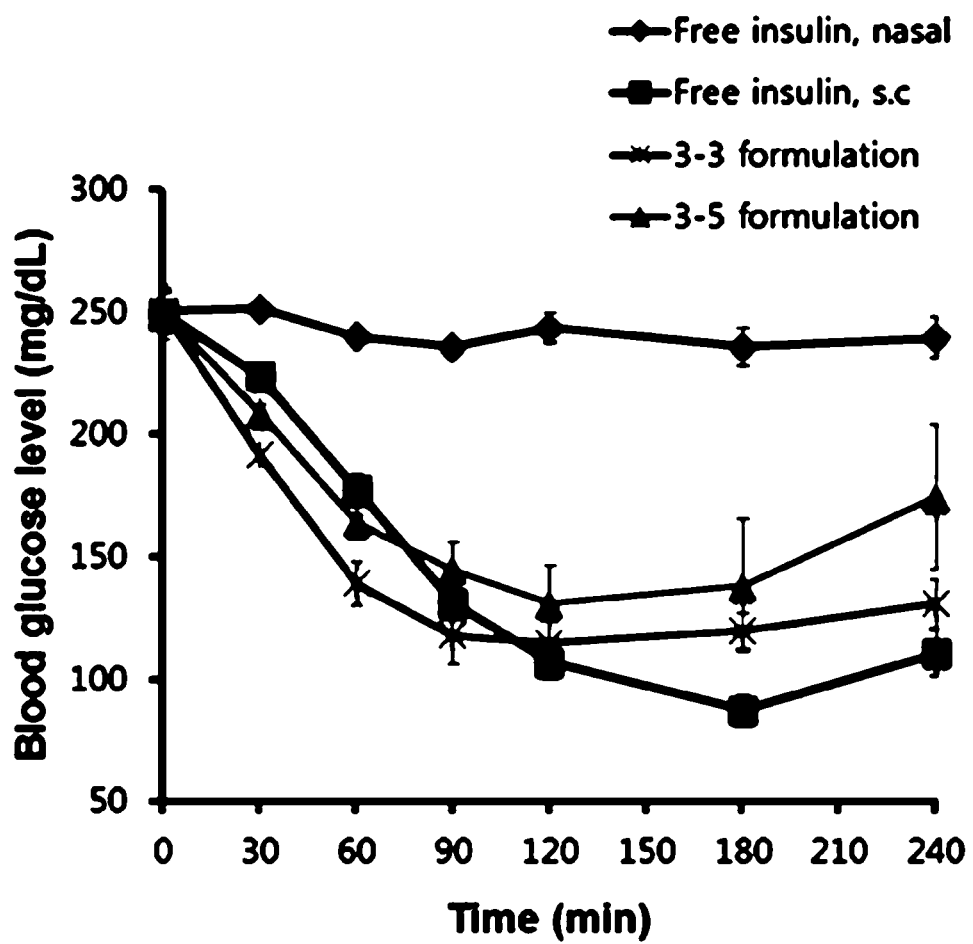
[Fig. 28]

[Fig. 29]
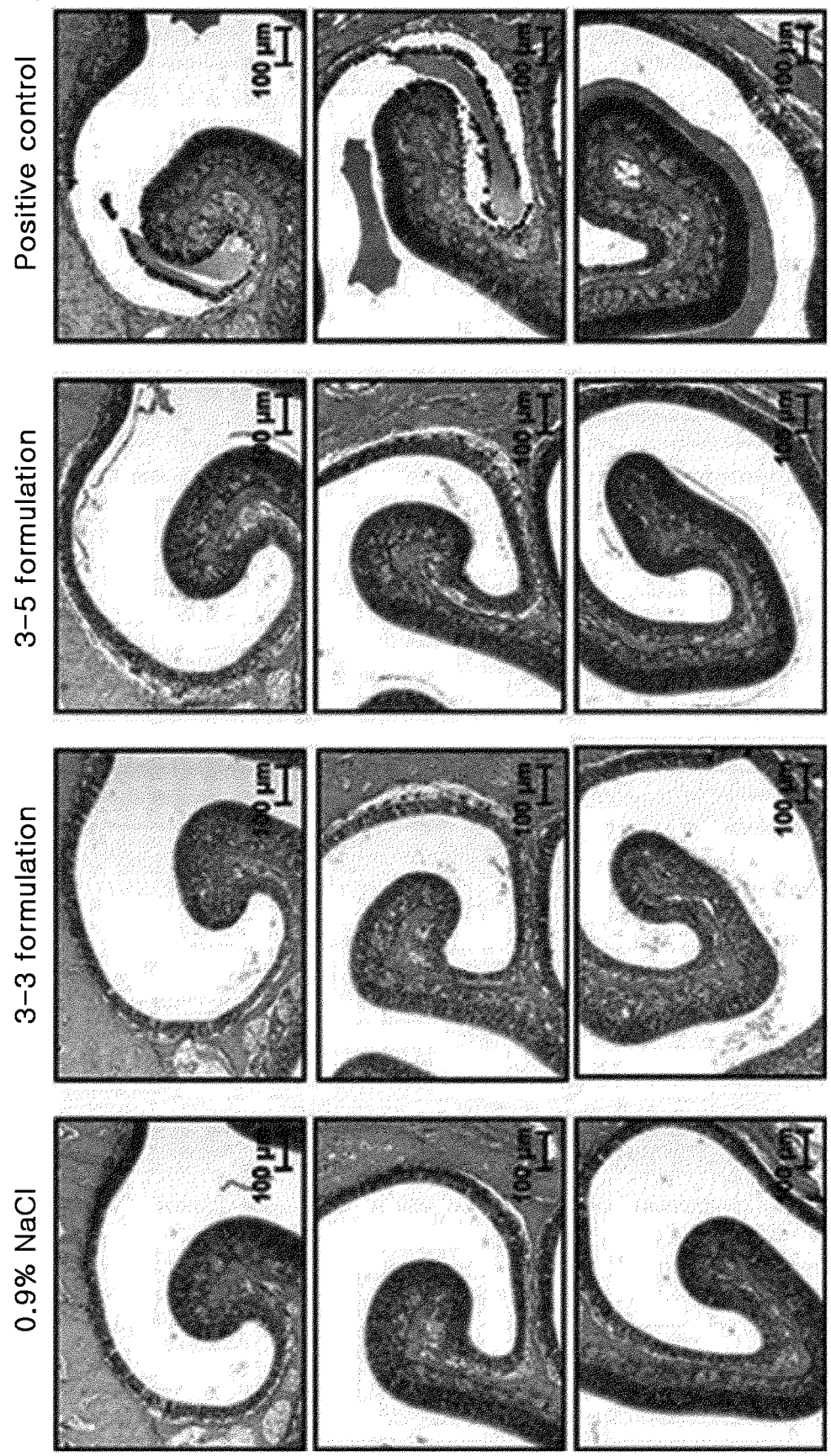

[Fig. 30]
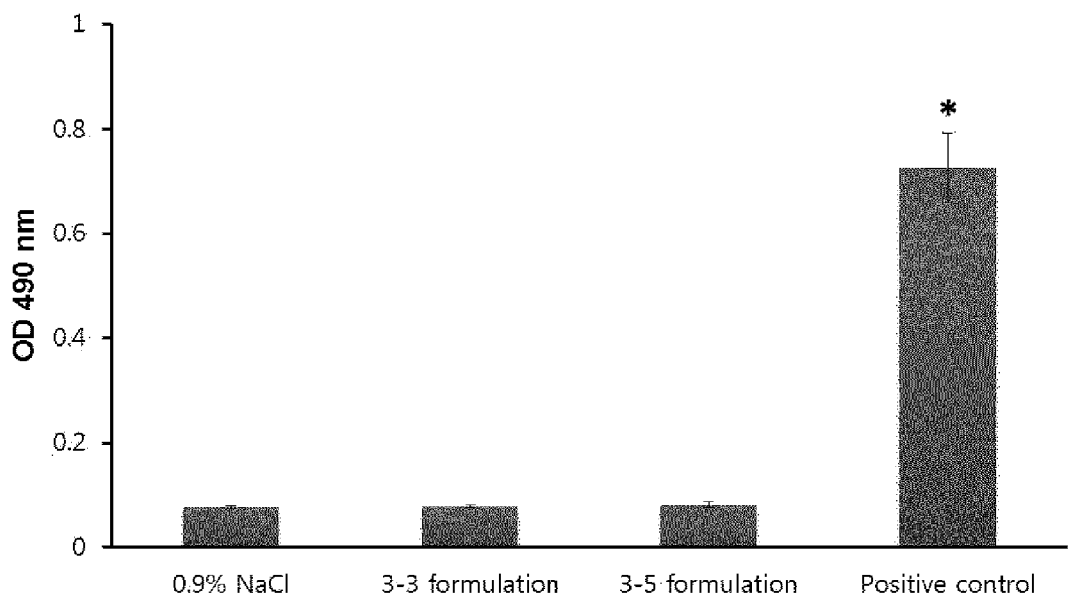
[Fig. 31]
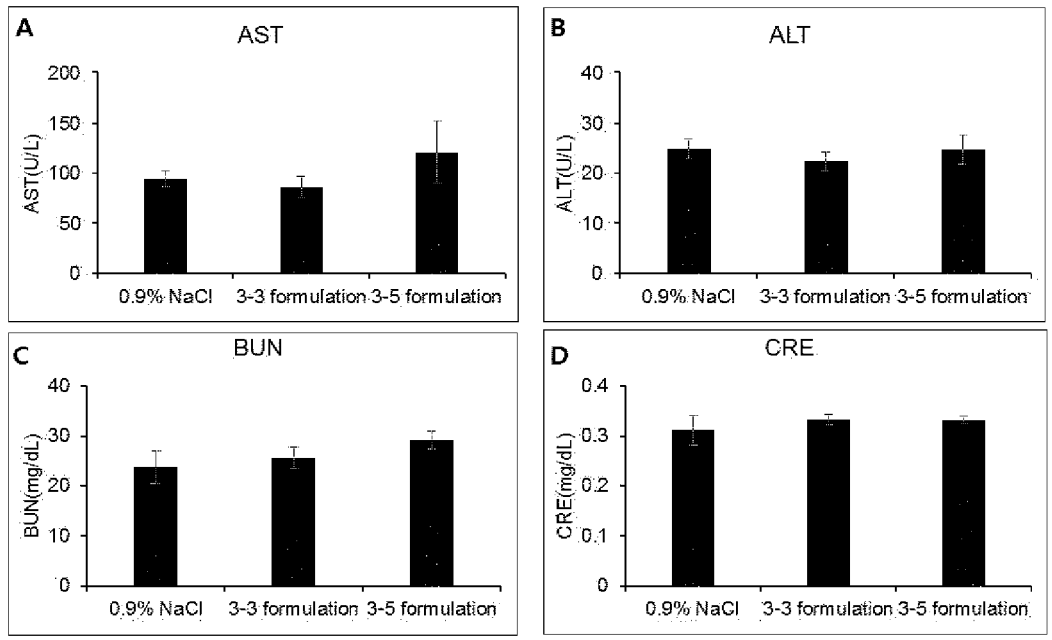

[Fig. 32]
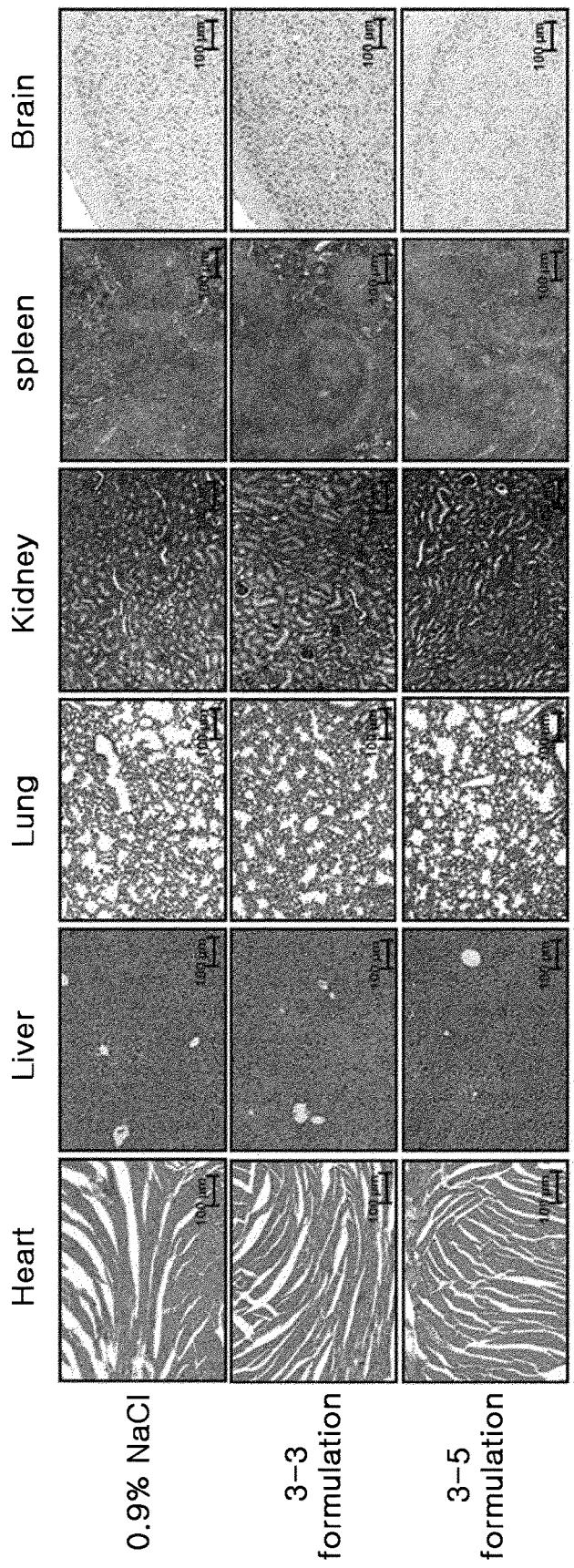

PEPTIDE WITH ABILITY TO PENETRATE CELL MEMBRANE

CROSS REFERENCE TO RELATED APPLICATIONS

This is the U.S. National Stage of International Application No. PCT/KR2017/003790, filed Apr. 6, 2018, which was published in English under PCT Article 21(2), which in turn claims the benefit of Korean Patent Application No. 10-2016-0042530, filed Apr. 6, 2016, Korean Patent Application No. 10-2016-0042531, filed Apr. 6, 2016, Korean Patent Application No. 10-2016-0042533, filed Apr. 6, 2016, and Korean Patent Application No. 10-2017-0044845, filed Apr. 6, 2017.

TECHNICAL FIELD

The present invention relates to a novel, translationally controlled tumor protein-derived protein transduction domain (TCTP-PTD) having the ability to penetrate the cell membrane and to the use of the TCTP-PTD for effectively delivering a target substance into the body through the cell membrane.

BACKGROUND ART

A protein transduction domain (hereinafter referred to as "PTD") functioning as a transmembrane protein domain is a peptide, also known as the cell-penetrating peptide (CPP).

In recent years, the PTD has been frequently used to efficiently deliver various substances (e.g., DNA, siRNA, peptides, proteins, etc.) into cells (Morris et al., Nat. Biotechnol. 19 (2001) 1173-1176; Jarver et al., Drug Discov. Today 9 (2004) 395-402). PTD-based drug delivery has attracted a great deal of attention, because it can increase the in vivo delivery efficiency of macromolecules such as therapeutic peptides, proteins and genes, which have been difficult to use as drugs by non-penetrant drug delivery. The present inventors previously found and reported a human translationally controlled tumor protein (TCTP)-derived PTD (hereinafter referred to as "TCTP-PTD") (Korean Patent No. 10-0859972).

DISCLOSURE OF INVENTION

Technical Problem

The present inventors have made extensive efforts to develop a cell membrane-penetrating peptide capable of effectively delivering a target substance in vivo, and as a result, have obtained many of variants of TCTP-PTD peptide and have found that the TCTP-PTD peptide and its variants have a variety of uses, thereby completing the present invention.

Solution to Problem

It is an object of the present invention to provide a novel TCTP-PTD peptide.

Another object of the present invention is to provide a complex comprising the TCTP-PTD peptide.

Still another object of the present invention is to provide a complex comprising the TCTP-PTD peptide and a target substance.

Still another object of the present invention is to provide a method for preventing or treating a target disease comprising administering the complex of the peptide and the target substance to a subject.

Still another object of the present invention is to provide a transfection kit comprising the TCTP-PTD peptide and a target substance.

Still another object of the present invention is to provide a nucleic acid encoding the TCTP-PTD peptide.

Still another object of the present invention is to provide a composition comprising the TCTP-PTD peptide.

Yet another object of the present invention is to provide a formulation comprising the TCTP-PTD peptide.

Advantageous Effects of Invention

The TCTP-PTD peptide according to the present invention is capable of improving the ability of a target substance to penetrate the cell membrane, thereby effectively delivering the target substance into a living body, including cells, tissue and blood.

BRIEF DESCRIPTION OF DRAWINGS

FIG. 1 shows the results of examining in vitro membrane penetration of TCTP-PTD in cervical cancer HeLa cells treated with FITC-labeled TCTP-PTD peptides (SEQ ID NO: 18, SEQ ID NO: 22, SEQ ID NO: 24, and SEQ ID NO: 27).

FIG. 2 shows the results of examining cell membrane penetration of L-PTD 13 and D-PTD 13 in BEAS-2B cells (human bronchial epithelial cells).

FIG. 3 is a graph showing the change in the blood glucose level of non-diabetic mice after intranasal administration of a mixture of insulin and SEQ ID NO: 1.

FIG. 4 is a graph showing the change in the blood glucose level of non-diabetic mice after intranasal administration of a mixture of insulin and TCTP-PTD (SEQ ID NO: 12, 17 or 22).

FIG. 5 is a graph showing the change in the blood glucose level of non-diabetic mice after intranasal administration of a mixture of insulin and SEQ ID NO: 18.

FIG. 6 is a graph showing changes in the blood glucose levels of type 1 diabetic model mice administered intranasally with insulin alone (Insulin alone), administered intranasally with a mixture of insulin and each TCTP-PTD (Insulin/SEQ ID NO: 27, Insulin/SEQ ID NO: 22, Insulin/SEQ ID NO: 24, Insulin/SEQ ID NO: 18) and administered subcutaneously with insulin (Subcutaneous injection).

FIG. 7 is a graph showing changes in the blood insulin concentrations of rats administered intranasally with insulin alone (Insulin alone), administered intranasally with a mixture of insulin and each variant TCTP-PTD (Insulin/SEQ ID NO: 27, Insulin/SEQ ID NO: 22, Insulin/SEQ ID NO: 24, Insulin/SEQ ID NO: 18) and administered subcutaneously with insulin (Subcutaneous injection).

FIG. 8 is a graph showing the change in the blood glucose level of non-diabetic mice after administration of a mixture of Ex-4 and the variant TCTP-PTD (SEQ ID NO: 27, 1, 42, 46 or 18) of the present invention and after intraperitoneal administration of glucose to the mice.

FIG. 9 is a graph showing the change in the blood glucose level of type 2 diabetic model mice (db/db mice), measured for 4 hours after administration of a mixture of Ex-4 and the variant TCTP-PTD (SEQ ID NO: 27, 18, 22 or 24) of the present invention and after intraperitoneal administration of glucose to the mice.

FIG. 10 is a graph showing the results of calculating the AUC of the blood glucose level shown in FIG. 9. (data are expressed as means±SEM. *p<0.05, **p<0.01 vs. exendin-4 and †p<0.05 vs. exendin-4/PTD 13).

FIG. 11 is a graph showing the results of measuring the blood exendin-4 concentration of each of a rat group administered intranasally with Ex-4 alone (Ex-4), a rat group administered with a mixture of Ex-4 and each variant TCTP-PTD (Ex-4/SEQ ID NO: 27, Ex-4/SEQ ID NO: 22, Ex-4/SEQ ID NO: 24, or Ex-4/SEQ ID NO: 18), and a rat group administered subcutaneously with Ex-4.

FIG. 12 depicts images showing that FITC-labeled TCTP-PTD peptides (SEQ ID NOs: 1, 22, 24, 12, 17 and 18) reached the hair follicle and dermis of the skin.

FIG. 13 depicts images showing that FITC-labeled D-PTD 13 and L-PTD 13 reached the hair follicle and dermis of the skin.

FIG. 14 shows the results of fluorescence microscope observation of nasal cavity tissue collected after administration of a mixture of OVA and TCTP-PTD 13 into the nasal cavity. (a) administration of OVA alone into the nasal cavity. (b) administration of an OVA/L-PTD 13 mixture into the nasal cavity. (c) administration of an OVA/D-PTD 13 mixture into the nasal cavity.

FIG. 15 is a graph showing the results of measuring the antigen (OVA)-specific IgG titer in plasma after administering a mixture of OVA and TCTP-PTD 13 into the nasal cavity.

OVA alone: a group administered intranasally with OVA alone;
OVA/L-PTD 13 (1:15 and 1:30): groups administered with OVA and L-PTD 13, mixed at molar ratios of 1:15 and 1:30, respectively;
OVA/D-PTD 13 (1:15 and 1:30): groups administered with OVA and D-PTD 13, mixed at molar ratios of 1:15 and 1:30, respectively;
OVA i.m: a group injected intramuscularly with OVA.

FIG. 16 is a graph showing the results of measuring the antigen (OVA)-specific secretory IgA secretion (OD value) in nasal washes obtained after a mixture of OVA and TCTP-PTD 13 into the nasal cavity.

OVA alone: a group administered intranasally with OVA alone;
OVA/L-PTD 13 (1:15 and 1:30): groups administered with OVA and L-PTD 13, mixed at molar ratios of 1:15 and 1:30, respectively;
OVA/D-PTD 13 (1:15 and 1:30): groups administered with OVA and D-PTD 13, mixed at molar ratios of 1:15 and 1:30, respectively;
OVA i.m: a group injected intramuscularly with OVA;
Control: untreated group.

FIG. 17 is a graph showing the results of measuring the antigen (OVA)-specific IgG titer in plasma after administering a mixture of OVA and D-PTD 13 or a mixture of OVA, D-PTD 13 and CpG into the nasal cavity.

OVA alone: a group administered with OVA alone;
OVA/D-PTD 13 (1:30): a group administered with OVA and D-PTD 13, mixed at a molar ratio of 1:30;
OVA/CpG/D-PTD 13 (1:1:30, 1:3:30 and 1:6:30): groups administered with OVA, CpG and D-PTD 13, mixed at molar ratios of 1:1:30, 1:3:30, and 1:6:30, respectively;
OVA i.m: a group administered intramuscularly with OVA.

FIG. 18 is a graph showing the results of measuring the antigen (OVA)-specific secretory IgA) secretion (OD value) in nasal washes after administering a mixture of OVA and D-PTD 13 or a mixture of OVA, D-PTD 13 and CpG into the nasal cavity.

OVA alone: a group administered with OVA alone;
OVA/D-PTD 13 (1:30): a group administered with OVA and D-PTD 13, mixed at a molar ratio of 1:30;
OVA/CpG/D-PTD 13 (1:1:30, 1:3:30 and 1:6:30): groups administered with OVA, CpG and D-PTD 13, mixed at molar ratios of 1:1:30, 1:3:30, and 1:6:30, respectively;
OVA i.m: a group administered intramuscularly with OVA;
Control: untreated group.

FIG. 19 is a graph showing the change of body weight as a function of time after intranasal administration of [D-Leu-4]-OB3 alone or in combination with D-PTD 13 or L-PTD 13.

Change of Body weight (%): body weight change relative to the initial body weight taken as 100%.

FIG. 20 is a graph showing the body weight measured 10 days after intranasal administration of [D-Leu-4]-OB3 alone or in combination with D-PTD 13 or L-PTD 13 (*: p<0.05).

Body weight (% of initial): body weight after 10 days, relative to the initial body weight taken as 100%.

FIG. 21 is a graph showing the cumulative food intake as a function of time after intranasal administration of [D-Leu-4]-OB3 alone or in combination with D-PTD 13 or L-PTD 13.

FIG. 22 is a graph showing the total food intake for 10 days after intranasal administration of [D-Leu-4]-OB3 alone or in combination with D-PTD 13 or L-PTD 13 (*: p<0.05).

FIG. 23 shows the change of body weight, measured after intranasally administering 2 mg/kg of [D-Leu-4]-OB3 in combination with D-PTD 13, D-PTD 13M1, D-PTD 13M2 or D-PTD 13M3 to mice for 10 days (6-7 mice per group; *: p<0.05, : p<0.01, *: p<0.001 vs PBS, D-TCTP-PTD 13(#), D-TCTP-PTD 13M1(*), TCTP-PTD 13M2($), TCTP-PTD 13M3(†)).

FIG. 24 shows the food intake, measured after intranasally administering 2 mg/kg of [D-Leu-4]-OB3 in combination with D-PTD 13, D-PTD 13M1, D-PTD 13M2 or D-PTD 13M3 to mice for 10 days (6-7 mice per group; *: p<0.05, : p<0.01, *: p<0.001 vs PBS, D-TCTP-PTD 13(#), D-TCTP-PTD 13M1(*), TCTP-PTD 13M2($), TCTP-PTD 13M3(†)).

FIG. 25 shows the results of evaluating the PD of nasal insulin formulations in normal white rats.

FIG. 26 shows the results of evaluating the single-dose toxicity of nasal insulin formulations.

FIG. 27 shows the results of evaluating the PK of nasal insulin formulations.

FIG. 28 shows the results of evaluating the PD of nasal insulin formulations in type 1 diabetic rats.

FIG. 29 shows the results of evaluating the repeated-dose toxicity of nasal insulin formulations (histological evaluation of the nasal mucous membrane).

FIG. 30 shows the results of measuring LDH levels in nasal washes after repeated administration of nasal insulin formulations.

FIG. 31 shows the results of evaluating the repeated-dose toxicity of nasal insulin formulations (serum biochemical examination).

FIG. 32 shows the results of evaluating the repeated-dose toxicity of nasal insulin formulations (histopathological examination).

SEQUENCE LISTING

The Sequence Listing is submitted as an ASCII text file [7037-101392-01_Replacement_Sequence_Listing.txt, created Mar. 30, 2020, 27.1 KB], which is incorporated by reference herein.

BEST MODE FOR CARRYING OUT THE INVENTION

Hereinafter, the present invention will be described in detail. Meanwhile, the features and embodiments disclosed in the present invention may also be applied to other features and embodiments. Namely, all combinations of various elements disclosed in the present invention fall within the scope of the present invention. Furthermore, it is not considered that the scope of the present invention is limited by the following detailed description.

One aspect of the present invention for achieving the above-described objects is a novel TCTP-PTD peptide. The peptide sequence of the present invention consists of amino acids determined by identifying the effects of the amino acid at each position of the peptide sequence on the characteristics, penetration ability, efficacy and solubility of a complex comprising the peptide to optimize these characteristics. Specifically, the novel TCTP-PTD peptide of the present invention appears as a combination of sequences determined based on the information between the property and function of the amino acid at each position by demonstrating the important characteristic of the amino acid at each position. For example, a specific amino acid sequence is a very important region in transmucosal delivery of a target substance, and each amino acid substituent can increase the ability to deliver a target substance (e.g., insulin, exendin-4, vaccines, etc.).

Accordingly, one aspect of the present invention is a TCTP-PTD peptide consisting of the following amino acid sequence:

R1-R2-R3-R4-R5-R6-R7-R8-R9-R10 wherein

R1 is any one amino acid selected from M, L or P,
R2 is any one amino acid selected from I, A, L, P or H,
R3 is any one amino acid selected from I, L, A, P or H,
R4 is any one amino acid selected from F, E, A, L, P or H,
R5 is any one amino acid selected from R or K,
R6 is any one amino acid selected from A, M, I, P, H or L,
R7 is any one amino acid selected from L, A, P or H,
R8 is any one amino acid selected from I, L, A, P or H,
R9 is any one amino acid selected from S, E or Y, and
R10 is any one amino acid selected from H, K, R, P or L,
and any one amino acid selected from KK, KKK, and KKKK may be added to R10, provided that the sequence is not MIIFRIAASHKK, MIIFRALISHKK, MIIFRAAASHKK, LIIFRIAASHKK, MIIFRIAAYHKK, MIIFKIAASHKK, LIIFRILISHKK, or MIIFRILISHKK.

In one embodiment of the present invention, the peptide may be a peptide consisting of any one amino acid sequence selected from the group consisting of SEQ ID NOs: 1 to 26.

In one embodiment of the present invention, the peptide may be a peptide consisting of any one amino acid sequence selected from the group consisting of SEQ ID NOs: 1, 12, 17, 18, 22 and 24.

Particularly, the peptide of the present invention comprises variants of the peptide consisting of the amino acid sequence of SEQ ID NO: 27, in which the variants are peptides which commonly comprise a 'MIIFR' sequence and in which one or more of the amino acids at positions 6 to 10 of the amino acid sequence of SEQ ID NO: 27 are substituted. Specifically, the variants may be those in which A at position 6 of the amino acid sequence of SEQ ID NO: 27 is substituted with L or I, L at position 7 of the amino acid sequence is substituted with A, I at position 8 of the amino acid sequence is A, S at position 9 of the amino acid sequence is substituted with Y, or H at position 10 of the amino acid sequence is substituted with P. More specifically, the peptide may be a peptide consisting of an amino acid sequence of SEQ ID NO: 12, 17, 18, 22 or 24, but is not limited thereto.

The peptide of the present invention is a novel TCTP-PTD peptide having the ability to penetrate the cell membrane. The TCTP-PTD peptide of the present invention has an excellent ability to penetrate the cell membrane, and has an excellent effect of delivering a target substance into living tissue.

As used herein, the term "cell membrane" refers to a membrane that forms the boundary between the interior of a cell and its outside environment. In one embodiment of the present invention, the cell membrane may be the cell membrane of any organism, for example, a unicellular or multicellular organism belonging to Bacteria, Archaea or Eukarya. The Eukarya may be any organisms belonging to Protista, Fungus, Plantae or Animalia. The animals may be any animals, including humans.

In the present invention, the "cell membrane" may be the membrane of any type of cell. For example, the "cell" may be one or more cells selected from the group consisting of epithelial cells, muscle cells, immune cells and endothelial cells. The cell may be a cell in a cell layer that lines the wall of an organ coming in direct contact with the exterior of the body, such as endothelium, epithelium, mucous membrane or the like, or that covers the surface of any organ or blood vessel in the body. In one embodiment of the present invention, the cells include skin epithelial cells, follicular epithelial cells, mucosal epithelial cells, corneal epithelial cells, scalp epithelial cells, corneal endothelial cells, and vascular endothelial cells. For example, the mucosal epithelial cells may be the epithelial cells of one or more mucous membranes selected from the group consisting of nasal, pulmonary, vaginal, rectal, anal, urethral, sublingual, ocular, conjunctival and oral mucous membranes. For example, the vascular endothelial cells may be the endothelial cells of various arteries, veins and capillaries, including brain blood vessels that form the blood brain barrier, the endothelial cells of lymphatic vessels, the endothelial cells of the inner heart wall, etc. Furthermore, the cells may be cells of various cancers, including cervical cancer, breast cancer, liver cancer, lung cancer, etc. In addition, the cells may be cells having receptors for various substances, including hormones, neurotransmitters, drugs, etc. For example, the cells may be cells having insulin receptor or glucagon-like-protein 1 (GLP1) receptors. However, the cells are not limited to the above-described examples.

The peptide of the present invention may be prepared by a conventional peptide synthesis method or preparation method known to those skilled in the art so as to have a peptide purity of 90% or higher. For example, the peptide of the present invention may be synthesized directly or produced by a peptide manufacturing company. The peptide may be prepared as a D-form or L-form peptide, or a peptide, only a portion of the sequence of which consists of a D-form or L-form peptide, or a racemic form thereof, by a conventional peptide synthesis method or preparation method known to those skilled in the art. Furthermore, other conventional modifications known to those skilled in the art may be performed in order to increase the stability of the peptide.

Another aspect of the present invention is a complex comprising the peptide.

Still another aspect of the present invention is a complex of the peptide and a target substance.

Still another aspect of the present invention is a method for preventing or treating a target disease comprising administering the complex of the peptide and the target substance to a subject. The target disease may vary depending on the target substance included in the complex.

As used herein, the term "complex" means a material comprising one or more peptides and one or more target substances. In the present invention, the "complex" may comprise the peptide and the target substance at a ratio of 1:1, 1: greater than 1, greater than 1:1, or greater than 1: greater than 1. For example, the complex may comprise the peptide and the target substance at a molar ratio of 1:1 to 1:100, or 100:1 to 1:1. However, the molar ratio is only an example, and is not limited thereto. In the present invention, the complex is a complex formed by simple mixing of the peptide and the target substance, a complex formed by mixing of the peptide and the target substance, or a complex formed by chemical linking or conjugation of the peptide and the target substance. Furthermore, the peptide and target substance of the complex may be linked to each other by a physical bond, a chemical bond, a covalent bond or a noncovalent bond, or may be combined or fused with each other by a mediator. Where the target substance is a protein, the sequence encoding the peptide may be added to the sequence encoding the protein, and the sequences may be linked to each other via a linker to form a fusion protein which can penetrate cells or which can be delivered into living tissue or blood. However, the method for forming the complex is not limited.

In one embodiment of the present invention, the "complex" may be a simple mixture of the peptide and the target substance.

In another embodiment of the present invention, the "complex" may be a complex formed by mixing of the peptide and the target substance. For example, the peptide and the target substance may be dissolved in buffer and mixed with each other at a certain molar ratio. After mixing, for stabilization, the mixture may be allowed to stand at a certain temperature, for example, room temperature or cold temperature (4° C.), for a certain time, for example, 1 second to 1 hour. The above temperature and time are illustrative only and are not limited thereto.

In still another embodiment of the present invention, the "complex" may be a complex in which the peptide and the target substance are linked to each other by a chemical bond. For example, the chemical bond may be a covalent bond or a non-covalent bond. For example, a specific functional group or linker may be attached to each of the TCTP-PTD peptide and the target substance, and then a chemical bond may be formed between the peptide and the target substance by the functional group or the linker. The chemical bond may be formed by any one reaction selected from among amine reactions, thiol reactions, carboxylate reactions, hydroxyl reactions, aldehyde reactions, ketone reactions, acrylate reactions, azide reactions, alkyne reactions, catechol reactions and pyrogallol reactions, but is not limited thereto.

If the chemical bond is formed by an amine reaction, an amine group may be linked to any one of the TCTP-PTD peptide and the target substance, and isothiocyanate, isocyanate, acryl azide, NHS (N-hydroxysuccinimide) ester, acyl chloride, sulfonyl chloride, aldehyde, epoxide, fluorobenzene or succinic anhydride may be linked to the other. The reaction between an amine group and isothiocyanate may form an isothiourea bond; the reaction between an amine group and isocyanate may form an isourea bond; the reaction between an amine group and acryl azide, NHS ester, acyl chloride or succinic anhydride may form an amide bond; the reaction between an amine group and sulfonyl chloride may form a sulfonamide bond; the reaction between an amine group and aldehyde or epoxide may form an amine bond; and the reaction between an amine group and fluorobenzene may form an arylamine bond; however, the scope of the present invention is not limited to these examples.

If the chemical bond is formed by a thiol reaction, a thiol group may be linked to any one of the TCTP-PTD peptide and the target substance, and iodoacetyl, maleimide, aziridine, acryloyl, fluorobenzene or vinylsulfone may be linked to the other. The reaction between a thiol group and iodoacetyl, maleimide, aziridine, acryloyl or vinylsulfone may form a thioether bond, and the reaction between a thiol group and fluorobenzene may form an aryl thioether; however, the scope of the present invention is not limited to these examples.

If the chemical bond is formed by a carboxylate reaction, a carboxylate group may be linked to any one of the TCTP-PTD peptide and the target substance, and diazoacetate may be linked to the other. In this case, the bond may be an ester bond, but is not limited to this example.

If the chemical bond is formed by a hydroxyl reaction, a hydroxyl group may be linked to any one of the TCTP-PTD peptide and the target substance, and isocyanate may be linked to the other. In this case, the bond may be a carbamate bond, but is not limited this example.

If the chemical bond is formed by an aldehyde reaction, an aldehyde group may be linked to any one of the TCTP-PTD peptide and the target substance, and hydrazide or amine may be linked to the other. The reaction between an aldehyde group and hydrazide may form a hydrazone bond, and the reaction between an aldehyde group and amine may form a Schiff base; but the scope of the present invention is not limited to these examples.

If the chemical bond is formed by a ketone reaction, a ketone group may be linked to any one of the TCTP-PTD peptide and the target substance, and hydrazide or amine may be linked to the other, but the scope of the present invention is not limited to this example.

If the chemical bond is formed by an acrylate reaction, acrylate may be linked to any one of the TCTP-PTD peptide and the target substance, and diazoacetic acid or alkene may be linked to the other, but the scope of the present invention is not limited to this example.

If the chemical bond is formed by an azide reaction, an azide group may be linked to any one of the TCTP-PTD peptide and the target substance, and alkene may be linked to the other. In this case, triazoline may be formed, but the scope of the present invention is not limited to this example.

If the chemical reaction is formed by an alkyne reaction, alkyne may be linked to any one of the TCTP-PTD peptide and the target substance, and an azide group may be linked to the other. In this case, triazole may be formed, but the scope of the present invention is not limited to this example.

If the chemical bond is formed by a catechol reaction or a pyrogallol reaction, a catechol reaction may be linked to any one of the TCTP-PTD peptide and the target substance, and an amine or thiol group may be linked to the other, but the scope of the present invention is not limited to this example.

In one embodiment of the present invention, where the bond between the TCTP-PTD peptide and the target substance is a covalent bond, the bond may be a peptide bond, a maleimide linker bond, a disulfide bond, or a sulfanyl (bi-functional) bond). In another embodiment of the present invention, where the bond between the TCTP-PTD peptide and the target substance is a non-covalent bond, the bond may be a charge-dependent bond. However, the bond is not limited to these examples.

In one embodiment of the present invention, the peptide and target substance in the "complex" may be linked to each other by a linker. The linker may be any linker known in the art.

However, the kind of chemical bond and the kind of linker or functional group used are not limited to the above-described examples.

In another embodiment of the present invention, the "complex" may be a complex formed by expression of a fusion of the peptide and the target substance. For example, when genes expressing the peptide and the target substance are inserted into a single vector and then an organism is transformed with the vector so that the genes inserted in the vector will be expressed, the peptide and the target substance can be expressed as a fusion protein. When the peptide and the target substance are expressed as a fusion protein, any linker may be included between the peptide and the target substance. For example, the linker may be a peptide linker consisting of one or more amino acids. The peptide linker may be, for example, a polypeptide consisting of 1 to 100 or 2 to 50 any amino acids. The peptide linker may comprise, for example, Gly, Asn and Ser residues, and may also comprise neutral amino acids such as Thr and Ala. An amino acid sequence suitable for the peptide linker is known in the art. Meanwhile, the linker may have a length determined so as not to affect the function of the complex. Specifically, the linker may comprise a total of 1 to 100 or 2 to 50 residues of one or more selected from the group consisting of Gly, Asn, Ser, Thr and Ala, but is not limited thereto.

The complex of the present invention may comprise, in addition to the peptide and the target substance, various specific portions, including a portion capable of targeting a specific cell or a specific intracellular organelle, a portion enabling the peptide portion to be activated in specific environments such as a pH change, level of a specific enzyme, temperature, etc., a portion enabling the peptide and the target substance to be separated from each other under specific environmental conditions, a linker portion or chemical moiety used when the peptide and the target substance form a complex, etc. For example, the PTD does not exhibit its function before microwaves, ultrasounds, radiofrequencies or the like are applied to a local site having a local disease environment (e.g., infarction, cancer, inflammation, etc.), and then the PTD exhibits its function in a specific changed environment to promote delivery of the target substance so that the target substance having cell- or environment-specific multiple functions can be delivered. Various portions may be added to the complex in order to increase the in vivo stability of the complex and to improve the pharmacokinetics of the complex to thereby maximize efficacy or reduce side effects. Furthermore, in order to increase the efficiency with which the target substance is delivered to the cytoplasm by the PTD, the complex may comprise a factor that promotes the release of the target substance to the cytoplasm. The positions of the peptide and the target substance in the complex are not limited, and the complex may comprise an additional portion capable of exhibiting a special function, or a portion capable of controlling the function of the complex or digesting the complex in a special environment. Such portions are not limited to the-above described examples.

The complex may be formed as various nanocarriers. As the nanocarriers, membrane lipid-based nanocarriers such as liposomes or micelles may be modified either with a ligand capable of targeting a specific cell or molecule or with a functional group for molecular imaging so that they can be used for the diagnosis and treatment of disease. When liposomes or micelles are modified using the peptide of the present invention as a ligand, intracellular delivery of the drugs or nanoparticles surrounded by the liposomes or micelles can be increased.

In one embodiment of the present invention, the target substance means either a substance which may be involved in regulation of physiological activity or exhibit pharmacological effects after delivery into a cell (the cytoplasm or the nucleus) or a substance having biological activity in various biological portions, including cells, tissues, intracellular substances or blood, to which it is to be delivered. For example, the target substance in the present invention may be one or more selected from the groups consisting of chemical compounds, proteins, glycoproteins, peptides, nucleotides, nucleic acids, carbohydrates, lipids, glycolipids, natural products, semi-synthetic substances, nanoparticles, liposomes, lipid-based formulations, viruses, quantum dots, fluorochromes and drugs.

In another embodiment of the present invention, the drug may be one or more selected from the group consisting of chemical drugs, biodrugs, nucleic acid drugs, peptide drugs, protein drugs, natural product drugs, semi-synthetic drugs, lipid drugs, enzymes, regulatory factors, growth factors, hormones, contrast agents and antibodies.

In another embodiment of the present invention, the term "biodrugs" means various biodrugs, including (original) biologics and biogenerics, biobetters, biosuperiors and the like. The biodrug refers to any drug prepared, secreted or semi-synthesized from a biological source, and examples thereof include, but are not limited to, vaccines, blood preparations, antigens, cell preparations, gene therapeutic agents, tissues, recombinant therapeutic proteins, stem cells, etc.

In another embodiment of the present invention, the "nucleic acids" include, but are not limited to, DNA, decoy DNA, plasmid, siRNA, shRNA, oligo nucleic acids, aptamers, antisense oligonuleotides, antisense RNA, microRNA, oligoribonucleotides, and transfer RNA, and also include locked nucleic acids (LNAs), peptide nucleic acids (PNAs), phosphorodiamidate morpholino oligomers (PMOs), and hexitol nucleic acids (HNAs), obtained by biochemically modifying antisense oligonucleotides to maximize the in vivo structural stability.

In an embodiment of the present invention, the target substance may be insulin. Thus, the scope of the invention may include a method for preventing or treating diabetes comprising administering a complex of the peptide and insulin to a subject. However the target substance that can be delivered to living tissue by the peptide of the present invention is not limited thereto.

Because insulin has a high molecular weight of 5.8 kDa, it cannot penetrate the mucous membrane, and thus has been administered by subcutaneous injection. However, injection causes fear and pain to the patient and also has a risk of infection, and thus a noninvasive administration method needs to be developed. In particular, a drug such as insulin, which should be administered periodically to diabetic patients, needs to be administered in a simple and convenient manner. The variant TCTP-PTD of the present invention enhances the ability of a drug to penetrate mucous membranes to thereby enable the drug to be administered to mucous membranes, including nasal mucous membranes. Furthermore, it is known that conventional nasal absorption promoters (e.g., surfactants, fatty acids, bile acid salts, etc.) may cause damage to mucous membranes, whereas the variant TCTP-PTD of the present invention causes little or no damage to mucous membranes. The TCTP-PTD of the present invention may greatly increase the penetration ability of target substances such as drugs, and thus a composition or formulation containing the TCTP-PTD of the present invention does not contain a conventional nasal absorption promoter or may contain a nasal absorption promoter in an amount that does not cause great damage to the mucous membrane.

Examples of another drug that may be delivered by the TCTP-PTD peptide of the present invention include osteoporosis therapeutic agents. The osteoporosis therapeutic agents may be biphosphonate-based drugs, parathyroid hormone (PTH) formulations, etc. For example, the parathyroid hormone (PTH) formulation may be full parathyroid hormone (PTH) or a formulation containing a portion of parathyroid hormone, and it may be, for example, teriparatide (Forsteo™), an injectable solution developed by Lily Co., Ltd. Teriparatide is a recombinant protein having the same amino acid sequence as that of a portion of parathyroid hormone. However, the kind of osteoporosis therapeutic agent that can be delivered by the present invention is not limited thereto.

The target substance that can be delivered by the TCTP-PTD peptide of the present invention may be an antibody. And the target substance can be any of various therapeutic antibody known in the art, and the kind thereof is not limited. For example, the antibody may be an antibody having anticancer activity, an antibody for treating hyperlipidemia, an antibody for treating autoimmune disease such as rheumatoid arthritis, etc., but the kind of antibody that can be delivered by the present invention is not limited thereto.

Still another aspect of the present invention is a kit comprising the peptide and the target substance. Because the kit comprises the cell-penetrating TCTP-PTD peptide of the present invention and the target substance, it may be any kit that may be used for the purpose of delivering the target substance into a living body or an isolated cell by use of the peptide. The kit may comprise an additional component capable of further enhancing the cell penetration ability of the target substance.

The present invention provides a nucleic acid encoding the peptide.

In one embodiment, the nucleic acid may consist of a nucleotide sequence of any one of SEQ ID NOs: 62 to 87. However, because multiple codons encode the one amino acid, nucleic acid sequences encoding the peptide of the present invention include, in addition to the nucleotide sequences of SEQ ID NOs: 62 to 87, all nucleotide sequences that encode the peptide of the present invention by other codons.

Still another aspect of the present invention is a composition comprising the peptide or a complex of the peptide and the target substance.

In the present invention, the composition may be used to deliver the target substance to living tissue or blood or to promote intracellular penetrate of the target substance. The composition may be delivered to cells forming the living tissue or by intercellular junction, but the method for delivering the composition is not limited.

The living tissue means one or more epithelial tissues, muscle tissues, nerve tissues or connective tissues, and each organ may comprise one or more tissues. Thus, examples of the organ include, but are not limited to, various living organs, including mucous membranes, skin, brain, lung, liver, kidney, spleen, heart, stomach, large intestine, digestive tract, bladder, ureter, urethra, ovary, spermary, reproductive organs, muscle, blood, blood vessels, lymphatic vessels, lymph nodes, thymus, pancreas, adrenal, thyroid gland, parathyroid gland, larynx, tonsil, bronchi, alveoli, etc.

Cells forming the living tissue include, but are not limited to, various cells, including epithelial cells, muscle cells, neurons, glandular cells, glial cells, germ cells, stem cells, mesenchymal cells, mesenchymal stem cells, bone cells, osteoblasts, osteoclasts, blood cells, hematopoietic cells, lung cells, liver cells, fibroblasts, immune cells, endothelial cells, adipocytes, chondrocytes, etc.

The epithelial cells include, but are not limited to, mucosal epithelial cells, follicular epithelial cells, digestive epithelial cells, respiratory epithelial cells, reproductive epithelial cells, urinary epithelial cells, etc. The endothelial cells include, but are not limited to, vascular endothelial cells and lymphatic endothelial cells.

In one embodiment of the present invention, the composition may be for delivering the target substance through the mucous membrane or the skin, but is not limited thereto.

The composition of the present invention may be used in various applications depending on the kind of target substance contained in the composition together with the peptide. For example, the composition of the present invention may be used to treat diseases in humans or animals. The diseases are not limited, and may be diseases against which a drug is delivered to cells, tissue or blood at a high concentration or enhanced delivery of a drug is required. For example, the diseases may be various diseases which can be treated with a gene therapeutic drug or a protein therapeutic drug having a high molecular weight or against which a therapeutic agent is administered by a changed route. Examples of the diseases include, but are not limited to, cancers, including breast cancer, liver cancer, brain cancer, prostate cancer, uterine cancer, ovarian cancer, gastric cancer, esophageal cancer, colorectal cancer, rectal cancer, thyroid cancer, blood cancer, skin cancer, lung cancer, etc., diabetes, obesity, asthma, hair loss, and the like. Furthermore, the composition may be used for research purposes to observe cell penetration ability in vitro or transmembrane intracellular delivery of a drug by use of the peptide, and may also be used for treatment of diseases such as cancer or diabetes, which are treated with gene therapeutic drugs or protein therapeutic drugs having a large molecular weight. The peptide may be applied to various molecules so that it can be used as diagnostic products, including contrast agents, diagnostic reagents and kits. In addition, the peptide may also be applied to functional health foods (functional health food compositions), cosmetic materials (cosmetic compositions), etc., but the scope of the present invention is not limited to the above-described examples.

As used herein, the term "functional health foods" refers to foods prepared (or processed) using the raw materials or components having functionality useful for the human body, and the term "functional" refers to regulating nutrients with respect to the structure and function of the human body or obtaining effects useful for health purposes, such as physiological activity. The functional health food composition of the present invention is prepared according to a conventional method.

As used herein, the term "cosmetic materials" refers to materials that can provide cosmetics or quasi-drugs. The term "cosmetics" refers to articles that are applied to the human body to keep the human body clean and beautiful to increase attractiveness and brighten the features or to maintain or enhance the health of the skin and hair, and that have a slight effect on the human body. The term "functional cosmetics" refers to products that are helpful in skin whitening or skin wrinkle reduction or assist in protecting the skin from UV rays. The term "functional cosmetics" is intended to encompass those defined by the "Ministerial Decree of the Korean Ministry for Health, Welfare and Family Affairs", and collectively refers to all products that improve skin conditions. The term "quasi-drugs" refers to drugs classified according to the classification system provided by the Korean Ministry for Health and Welfare, among articles having slight effects on the human body, rather than medical drugs that are used to treat or prevent diseases. According to the Korean Pharmaceutical Affairs Act, the quasi-drugs exclude articles that are used as medical drugs, and the quasi-drugs include fiber or rubber products that are used for the treatment or prevention of humans and animals, articles that have a slight effect on the human body or do not act directly on the human body and that exclude devices or apparatuses, and bactericides and insecticides for preventing infectious diseases. The cosmetic composition of the present invention may further contain components which are generally used in cosmetic compositions.

In one embodiment of the present invention, the composition may be used as any one or more forms selected from the group consisting of oral formulations, injectable formulations, formulations for mucosal administration, formulations for oral mucosal administration, formulations for nasal administration, ocular formulations, formulation for vaginal administration, inhalation formulations, formulations for external use, formulation for transdermal absorption, formulations for sublingual administration, formulations for implantation, and suppositories, but is not limited thereto.

In one embodiment of the present invention, the composition may further contain a signal peptide that enables the target substance to be delivered to a specific organ or a specific intracellular organelle. The signal sequence is a short peptide having a length of 5-30 amino acids, and it remains in a specific intracellular organelle (ER, Golgi, endosome), is secreted from a cell, or is inserted into the cell membrane. The composition of the present invention may contain any known signal sequence, and the target substance may be moved to a specific intracellular site by the signal sequence, but the scope of the present invention is not limited thereto.

In one embodiment of the present invention, the composition may further contain a substance or portion that enables the target substance to target a specific organ or a specific cell so as to be delivered to the specific organ or the specific cell. For example, the composition may further contain an antibody that binds specifically to a receptor present in a specific cell. For example, if an antibody (Herceptin) that binds specifically to HER-2 receptor in breast cancer cells is additionally linked to the peptide/target substance complex in the composition of the present invention, the peptide/target substance complex can bind specifically to a breast cancer cell through the antibody and can be delivered into the cell. The kind of substance that enables the peptide/target substance complex to be delivered into a specific organ or a specific cell as described above is not limited, and any targeting molecule known in the art may be used in the present invention.

In one embodiment of the present invention, the composition may further contain a portion or substance enabling the PTD to exhibit its cell penetration ability depending on a specific pH, enzymatic activity, light or oxygen environment by use of a pH-sensitive system, an enzyme-sensitive system, a light-sensitive system or an oxygen-sensitive system as a portion of an activable cell penetrating peptide whose cell penetration ability is activated only in the exterior or interior of a cell, but the scope of the present invention is not limited to the above examples.

In one embodiment of the present invention, the above-described composition or formulation may further contain a substance enabling g the peptide and the target substance to be more easily released from intracellular endosomes (endosomal escape). For example, this substance may be a membrane-disruptive peptide, a membrane-disruptive polymer, a lysosomotropic agent or the like, and a strategy that links the tetramerization domain of p53 protein (p53tet) or links PMAPs (pH-dependent membrane active peptide) to the peptide may be used, but the scope of the present invention is not limited to these examples.

In one embodiment of the present invention, the above-described composition or formulation may further contain a substance or portion that can increase the half-life of the peptide or the target substance.

In one embodiment of the present invention, the above-described composition or formulation may be formulated so that the peptide and the target substance are not degraded in vivo before they are delivered to a desired cell. For example, if the target substance is to be absorbed in the epithelium of the small intestine, the composition or formulation may be formulated so that the peptide and the target substance will not be degraded or will not be absorbed into any other cells before they reach the epithelium of the small intestine in digestive tracts. As another example, if the composition of the present invention is to be injected subcutaneously or intramuscularly so that the target substance will enter blood vessels, the composition may be formulated so as to reduce the extent to which the composition is absorbed into skin cells, muscle cells or adipose cells. The above-mentioned example is only illustrative, and the scope of the present invention is not limited thereto.

In one embodiment of the present invention, the composition of the present invention may further contain any substance that inhibits an immune response to the peptide. For example, the composition of the present invention may further contain an immunosuppressive agent.

Still another aspect of the present invention relates to the use of a peptide consisting of the following amino acid sequence, that is, the TCTP-PTD peptide of the present invention:

R1-R2-R3-R4-R5-R6-R7-R8-R9-R10 wherein

R1 is any one amino acid selected from M, L, P, Q, C, F or W,

R2 is any one amino acid selected from I, A, L, P or H,

R3 is any one amino acid selected from I, L, A, P or H,

R4 is any one amino acid selected from F, E, A, L, P, H, Y, S or R,

R5 is any one amino acid selected from A, R or K,

R6 is any one amino acid selected from A, M, I, P, H, L, R or D,

R7 is any one amino acid selected from L, A, P, H, K, R or E,

R8 is any one amino acid selected from I, L, A, P, H or K,

R9 is any one amino acid selected from T, S, E or Y, and

R10 is any one amino acid selected from H, K, R, P, L or E, and no amino acid is added to R10, or any one amino acid selected from R, RR, HH, K, KK, KKK and KKKK may be added to R10.

Specifically, the TCTP-PTD peptide of the present invention has the ability to penetrate the cell membrane, and thus may be used in combination with various target substances. Furthermore, the peptide may be delivered into hair follicles and the brain, and thus can be used in various applications.

One specific aspect of the present invention is a composition for delivery of exendin-4, comprising: a peptide consisting of the following amino acid sequence; and exendin-4:

R1-R2-R3-R4-R5-R6-R7-R8-R9-R10 wherein

R1 is any one amino acid selected from M, L, P, Q, C, F or W,

R2 is any one amino acid selected from I, A, L, P or H,

R3 is any one amino acid selected from I, L, A, P or H,

R4 is any one amino acid selected from F, E, A, L, P, H, Y, S or R,

R5 is any one amino acid selected from A, R or K,

R6 is any one amino acid selected from A, M, I, P, H, L, R or D,

R7 is any one amino acid selected from L, A, P, H, K, R or E,

R8 is any one amino acid selected from I, L, A, P, H or K,

R9 is any one amino acid selected from T, S, E or Y, and

R10 is any one amino acid selected from H, K, R, P, L or E, and no amino acid is added to R10, or any one amino acid selected from among R, RR, HH, K, KK, KKK and KKKK may be added to R10.

In one embodiment of the present invention, the peptide may consist of any one amino acid sequence selected from the group consisting of SEQ ID NOs: 1 to 61. Specifically, the peptide may consist of any one amino acid sequence selected from the group consisting of SEQ ID NOs: 1, 18, 22, 24, 27, 42 and 46. Particularly, the scope of the peptide according to the present invention includes variants of the peptide comprising the amino acid sequence of SEQ ID NO: 27, in which the variants are peptides which commonly comprise a 'MIIFR' sequence and H at position 10 and in which one or more of the amino acids at positions 6 to 9 of the amino acid sequence of SEQ ID NO: 27 are substituted. Specifically, the variants are those in which A at position 6 of the amino acid sequence of SEQ ID NO: 27 is substituted with L or I, L at position 7 of the amino acid sequence is substituted with A, I at position 8 of the amino acid sequence is A, or S at position 9 of the amino acid sequence is substituted with Y. More specifically, the variant may be a peptide consisting of the amino acid sequence of SEQ ID NO: 18, 22, 24, 27 or 46, but is not limited thereto.

The TCTP-PTD peptide of the present invention has an excellent ability to penetrate the cell membrane, and also has an excellent effect of delivering exendin-4 into living tissue or blood through the cell membrane.

In the present invention, "exendin-4" is a GLP-1-based peptide for treating diabetes, and is currently being administered by injection, because it has a low ability to penetrate the mucous membrane, due to its high molecular weight. Exendin-4 is a glucagon-like peptide-1 (GLP-1)-based peptide consisting of 39 amino acids, which is used as an agent for treating diabetes. It is a substance that stimulates insulin secretion, has a half-life longer than that of GLP-1, and is used as an agent for treating diabetes. Exendin-4 has a low ability to penetrate the mucous membrane, and thus is mainly administered by subcutaneous injection. With respect to exendin-4 used in the present invention, exenatide and exenatide LAR (long acting release), which are synthetic forms of exendin-4, and other exenatide-based drugs, have been developed and used as agents for treating diabetes. In the present invention, as exendin-4, a conventional extract product known to those skilled in the art or a synthetic product such as exenatide may be purchased and used. Exendin-4 that is used in the present invention may be a conventional extract product (form separated from nature) or a synthetic form (exenatide or exenatide LAR). The present invention provides a complex comprising the peptide and exendin-4, and a composition for delivery of exendin-4, comprising the complex.

The composition comprising the TCTP-PTD peptide and the target substance is as described above.

The present invention provides a nucleic acid encoding the peptide.

In one embodiment of the present invention, the nucleic acid may consist of any one nucleotide sequence selected from SEQ ID NOs: 62 to 122. However, because multiple codons encode the one amino acid, nucleic acid sequences encoding the peptide of the present invention include, in addition to the nucleotide sequences of SEQ ID NOs: 62 to 122, all nucleotide sequences that encode the peptide of the present invention by other codons.

In one embodiment of the present invention, the composition of the present invention may be used for treatment of any disease that can be treated with exendin-4. For example, the composition of the present invention may be used for treatment of various metabolic diseases, including diabetes and obesity, dementia, osteoporosis, Alzheimer's disease, Parkinson's disease, stroke, central and peripheral nervous diseases, and various complications occurring with the above diseases, for example, peripheral neuropathy, diabetic hypertension, diabetic ketoacidosis, hyperosmolar hyperglycemic syndrome, and various vascular disease complications, such as hypertension, retinopathy, nephropathy, neuropathy, coronary artery disease, peripheral artery disease, cerebral vascular disease or the like. For example, the composition of the present invention may be used for treatment of Alzheimer's disease and Parkinson's disease, but the scope of the present invention is not limited to these examples. Thus, the scope of the present invention may include a method for preventing or treating a disease, including diabetes, obesity, dementia, osteoporosis, Alzheimer's disease, Parkinson's disease, stroke, central and peripheral nervous diseases, peripheral neuropathy, diabetic hypertension, diabetic ketoacidosis, hyperosmolar hyperglycemic syndrome, hypertension, retinopathy, nephropathy, neuropathy, coronary artery disease, peripheral artery disease, cerebral vascular disease, comprising administering a composition comprising the peptide and exendin-4, but is not limited thereto.

In one embodiment of the present invention, the peptide of the present invention may be used for treatment of any brain-related disease which can be treated with exendin-4, because it has an excellent effect of delivering exendin-4 into the brain.

Still another aspect of the present invention is a kit comprising the peptide and exendin-4. The kit comprising the TCTP-PTD peptide and the target substance is as described above.

Still another aspect of the present invention is a composition for delivering a target substance into a hair follicle, comprising: a peptide consisting of the following amino acid; and a target substance:

R1-R2-R3-R4-R5-R6-R7-R8-R9-R10 wherein

R1 is any one amino acid sequence selected from M, L, P, Q, C, F or W,

R2 is any one amino acid sequence selected from I, A, L, P or H,

R3 is any one amino acid sequence selected from I, L, A, P or H,

R4 is any one amino acid sequence selected from F, E, A, L, P, H, Y, S or R,

R5 is any one amino acid sequence selected from A, R or K,

R6 is any one amino acid sequence selected from A, M, I, P, H, L, R or D,

R7 is any one amino acid sequence selected from L, A, P, H, K, R or E,

R8 is any one amino acid sequence selected from I, L, A, P, H or K,

R9 is any one amino acid sequence selected from T, S, E or Y, and

R10 is any one amino acid sequence selected from H, K, R, P, L or E, and no amino acid is added to R10, or any one amino acid selected from R, RR, HH, K, KK, KKK and KKKK may be added to R10.

In one embodiment of the present invention, the peptide may consist of any one amino acid sequence selected from the group consisting of SEQ ID NOs: 1 to 61. Specifically, the peptide may consist of any one amino acid sequence selected from the group consisting of SEQ ID NOs: 1, 12, 17, 18, 22, 24 and 27. Particularly, the scope of the peptide according to the present invention includes variants of the peptide comprising the amino acid sequence of SEQ ID NO: 27, in which the variants are peptides which commonly comprise a 'MIIFR' sequence and in which one or more of the amino acids at positions 6 to 10 of the amino acid sequence of SEQ ID NO: 27 are substituted. Specifically, the variants are those in which A at position 6 of the amino acid sequence of SEQ ID NO: 27 is substituted with L or I, L at position 7 of the amino acid sequence is substituted with A, I at position 8 of the amino acid sequence is A, S at position 9 of the amino acid sequence is substituted with Y, or H at position 10 of the amino acid sequence is substituted with P. More specifically, the peptide may be a peptide consisting of an amino acid sequence of SEQ ID NO: 12, 17, 18, 22, 24 or 27, but is not limited thereto. Synthesis, preparation and modification of the peptide, and a composition comprising the peptide, are as described above.

The target substance in the composition may be any one or more selected from hair growth-promoting drugs, hair growth-inhibiting drugs, antibiotics, and anti-inflammatory drugs, but is not limited thereto.

The "hair growth-promoting drugs" may be any drugs that promote hair growth. The hair growth-promoting drugs may be finasteride, dutasteride, minoxidil, or other various hair growth-promoting drugs known in the art, but are not limited thereto.

The "hair growth-inhibiting drugs" may be any drugs that inhibit hair growth. The hair growth-inhibiting drugs may be antiandrogen drugs, spirolactone, contraceptives, or eflornithine, but are not limited thereto.

The "antibiotics" are any substances that inhibit the growth of bacteria or viruses or kill bacteria or viruses.

The "anti-inflammatory drugs" are any drugs for systemically or topically inhibiting inflammation.

Thus, the scope of the present invention may include a method for promoting or inhibiting hair-growth, comprising administering a complex of the peptide and hair growth-promoting drugs. The scope of the present invention may include a method for inhibiting the growth of bacteria or viruses; or killing bacteria or viruses, comprising a composition comprising the peptide and antibiotics. The scope of the present invention may include a method for inhibiting inflammation, comprising a complex of the peptide and anti-inflammatory drugs.

Still another aspect of the present invention is a composition for vaccine delivery, comprising: a peptide consisting of the following amino acid sequence; and a vaccine:

R1-R2-R3-R4-R5-R6-R7-R8-R9-R10 wherein

R1 is any one amino acid selected from M, L, P, Q, C, F or W,

R2 is any one amino acid selected from I, A, L, P or H,

R3 is any one amino acid selected from I, L, A, P or H,

R4 is any one amino acid selected from F, E, A, L, P, H, Y, S or R,

R5 is any one amino acid selected from A, R or K,

R6 is any one amino acid selected from A, M, I, P, H, L, R or D,

R7 is any one amino acid selected from L, A, P, H, K, R or E,

R8 is any one amino acid selected from I, L, A, P, H or K,

R9 is any one amino acid selected from T, S, E or Y, and

R10 is any one amino acid selected from H, K, R, P, L or E, and no amino acid is added to R10, or any one amino acid sequence selected from R, RR, HH, K, KK, KKK and KKKK may be added to R10.

Still another aspect of the present invention is a composition for preventing or treating a disease comprising administering a composition comprising the peptide and a vaccine.

In one embodiment of the present invention, the peptide may consist of any one amino acid sequence selected from the group consisting of SEQ ID NOs: 1 to 61. Particularly, the scope of the peptide according to the present invention includes variants of the peptide comprising the amino acid sequence of SEQ ID NO: 27, in which the variants are peptides which commonly comprise a 'MIIFR' sequence, L at position 7 and H at position 10 and in which one or more of the amino acids at positions 6, 8 and 9 of the amino acid sequence of SEQ ID NO: 27 are substituted. Specifically, the variants are those in which A at position 6 of the amino acid sequence of SEQ ID NO: 27 is substituted with L, I at position 8 of the amino acid sequence is A, or S at position 9 of the amino acid sequence is substituted with Y. More specifically, the variant may be a peptide consisting of an amino acid sequence of SEQ ID NO: 22, 24, 18 or 27, but is not limited thereto. In the present invention, the peptides consisting of the amino acid sequences of SEQ ID NOs: 22, 24 and 18 were named "TCTP-PTD 13M1", "TCTP-PTD 13M2", and "TCTP-PTD 13M3", respectively. Synthesis, preparation and modification of the peptide, and a composition comprising the peptide, are as described above.

In the present invention, the peptide may be a D-form or L-form peptide, or a peptide, only a portion of the sequence of which consists of a D-form or L-form peptide, or a racemic form thereof.

In the present invention, the term "vaccine" means an antigen that is used to provide immunity to humans or animals. With respect to the vaccine, a part or the whole of an artificially inactivated or attenuated pathogen is injected into a subject to activate the immune system, before the subject is infected with the pathogen. In this case, damage caused by the pathogen can be prevented or minimized, even when the subject is infected with the pathogen. The kind of vaccine that may be the target substance of the peptide of the present invention is not limited. In one embodiment of the present invention, the vaccine may be a vaccine against a respiratory disease that can be prevented by mucosal immune responses. For example, the respiratory disease vaccine may be an influenza virus vaccine, a Pneumococcal vaccine, a tuberculosis vaccine, a MERS vaccine, a SARS vaccine, an adenovirus vaccine, or the like. The vaccine that can be delivered by the present invention is not limited to the respiratory disease vaccine, and examples thereof include, vaccines against cervical cancer, Japanese encephalitis, diphtheria, tetanus, pertussis, typhoid, chickenpox, polio, measles, rubella, mumps, yellow fever, hepatitis A, hepatitis B, hepatitis C, meningococcal disease, herpes zoster, etc., but are not limited to the above examples.

The animal vaccines that can be delivered by the present invention may include, for porcine vaccines, vaccines against Aujeszky's disease, swine erysipelas, hog cholera, Japanese encephalitis, porcine Parvovirus, porcine epidemic diarrhea (PED), (transmissible gastroenteritis (TGE), porcine rotavirus infection, porcine atrophic rhinitis, Pasteurella multocida, pleuropneumonia, Colibacillosis, etc; for bovine vaccines, vaccines against rotavirus, coronavirus, infectious bovine rhinotracheitis (IBR), bovine parainfluenza virus, bovine virus diarrhea (BVD), bovine respiratory syncytial virus (BRSV), Akabane disease, Ibaraki disease, ephemeral fever, bovine pneumonic pasteurellosis, anthrax, blackleg, breast cancer (*Staphylococcus aureus*), etc.; for chick viruses, vaccines against Newcastle disease, Marek's disease, infectious bursal disease, infectious bronchitis (TB), avian encephalomyelitis, avian influenza, avian cholera, etc; for canine vaccines, measles, hepatitis, pavovirus, parainfluenza, coronavirus enteritis, infectious bronchitis (Kennel cough), canine influenza, rabies, etc; and for feline vaccines, feline panleukopenia virus (FPV), feline viral rhinotrachetis (FVR), feline calicivirus (FCV), feline leukemia virus (FeLV), chlamydia (CH), rabies, infectious peritonitis, etc., but are not limited to the above examples.

Examples of vaccines that can be the target substance of the peptide of the present invention include, but are not limited to, antigens or antigenic compositions which are capable of eliciting an immune response against a human pathogen and which are derived from the following: HIV-1, (such as tat, nef, gp120 or gp160, gp40, p24, gag, env, vif, vpr, vpu, rev), human herpes viruses, such as gH, gL gM gB gC gK gE or gD or derivatives thereof or early-expressed protein, such as ICP27, ICP47, ICP4, ICP36 from HSV1 or HSV2, cytomegalovirus, especially human cytomegalovirus, (such as gB or derivatives thereof), Epstein Barr virus (such as gp350 or derivatives thereof), Varicella Zoster virus (such as gpI, II, III and IE63), or from a hepatitis virus such as hepatitis B virus (for example hepatitis B surface antigen or hepatitis core antigen or pol), hepatitis C virus antigen and hepatitis E virus antigen, or from other viral pathogens, such as paramyxovirus: respiratory syncytial virus (such as F and G proteins or derivatives thereof), or antigens from parainfluenza virus, measles virus, mumps virus, human papilloma viruses (for example HPV6, 11, 16, 18, e.g., L1, L2, E1, E2, E3, E4, E5, E6, E7), flaviviruses (e.g. yellow fever virus, Dengue virus, Tick-borne encephalitis virus, Japanese encephalitis virus) or influenza virus cells (such as HA, NP, NA, or M proteins, or combinations thereof), or antigens derived from bacterial pathogens such as *Neisseria* sp., including *N. gonorrhea* and *N. meningitidis* (e.g., transferrin-binding proteins, lactoferrin binding proteins, Pi1C, adhesins); *S. pyogenes* (for example M proteins or fragments thereof, C5A protease), *S. agalactiae, S. mutans; H. ducreyi; Moraxella* sp., including *M catarrhalis*, also known as *Branhamella catarrhalis* (for example high and low molecular weight adhesins and invasions); *Bordetella* sp., including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* sp., including *M. tuberculosis* (for example, ESAT6, Antigen 85A, -B or -C, MPT 44, MPT59, MPT45, HSP10, HSP65, HSP70, HSP 75, HSP90, PPD 19 kDa [Rv3763], PPD 38 kDa [Rv0934]), *M. bovis, M. leprae, M. avium, M. paratuberculosis, M. smegmatis; Legionella* sp., including *L. pneumophila; Escherichia* sp., including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* sp., including *V. cholera* (for example, cholera toxin or derivatives thereof); *Shigella* sp., including *S. sonnei, S. dysenteriae, S. flexnerii; Yersinia* sp., including *Y. enterocolitica* (for example, a Yop protein), *Y. pestis, Y. pseudotuberculosis; Campylobacter* sp., including *C. jejuni* (for example, toxins, adhesins and invasins) and *C. coli; Salmonella* sp., including *S. typhi, S. paratyphi, S. choleraesuis, S. enteritidis; Listeria* sp., including *L monocytogenes; Helicobacter* sp., including *H. pylori* (for example urease, catalase, vacuolating toxin); *Pseudomonas* sp., including *P. aeruginosa; Staphylococcus* sp., including *S. aureus, S. epidermidis; Enterococcus* sp., including *E. faecalis, E. faecium; Clostridium* spp., including *C. tetani* (for example, tetanus toxin and derivative thereof), *C. difficile* (for example, clostridium toxins A or B and derivatives thereof); *Bacillus* spp., including *B. anthracis* (for example botulinum toxin and derivatives thereof); *Corynebacterium* spp., including *C. diphtheriae* (for example, diphtheria toxin and derivatives thereof); *Borrelia* spp., including *B. burgdorferi* (for example, OspA, OspC, DbpA, DbpB), *B. garinii* (for example, OspA, OspC, DbpA, DbpB), *B. afzelii* (for example, OspA, OspC, DbpA, DbpB), *B. andersonii* (for example, OspA, OspC, DbpA, DbpB), *B. hermsii; Ehrlichia* spp., including *E. equi* and the agent of the human granulocytic ehrlichiosis; *Rickettsia* spp, including *R. rickettsii; Chlamydia* spp., including *C. trachomatis* (for example, MOMP, heparin-binding proteins), *C. pneumoniae* (for example, MOMP, heparin-binding proteins), *C. psittaci; Leptospira* spp., including *L. interrogans; Treponema* spp., including *T. pallidum* (for example, the rare outer membrane proteins), *T. denticola, T. hyodysenteriae; Toxoplasma* spp., including *T. gondii* (for example, SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L major; Pneumocystis* spp., including *P. carinii; Trichomonas* spp., including *T. vaginalis; Schisostoma* spp., including *S. mansoni*, or yeast such as *Candida* spp., including *C. albicans; Cryptococcus* spp., including *C. neoformans*.

Other antigens for *M. tuberculosis* include, for example, Rv2557, Rv2558, RPFs: Rv0837c, Rv1884c, Rv2389c, Rv2450, Rv1009, aceA (Rv0467), PstS1, (Rv0932), SodA (Rv3846), Rv2031c 16 kDal., Tb Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include, but are not limited to, Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748).

Preferred antigens for *Chlamydia* include, for example, the high molecular weight protein (HWMP) (WO 99/17741), ORF3 (EP 366 412), and putative membrane proteins (Pmps). Other *Chlamydia* antigens of the vaccine formulation can be selected from the group described in WO 99/28475.

Preferred bacterial vaccines comprise antigens derived from *Streptococcus* spp., including *S. pneumoniae* (PsaA, PspA, streptolysin, choline-binding proteins) and the protein antigen *Pneumolysin* (Biochem Biophys Acta, 1989, 67, 1007; Rubins et al., Microbial Pathogenesis, 25, 337-342), and mutant detoxified derivatives thereof (WO 90/06951; WO 99/03884). Other preferred bacterial vaccines include, but are not limited to, antigens derived from *Haemophilus* spp., including *H. influenzae* type B (for example, PRP and conjugates thereof), non-typeable *H. influenzae*, for example, OMP26, high molecular weight adhesins, P5, P6, protein D and lipoprotein D, and fimbrin and fimbrin derived peptides (U.S. Pat. No. 5,843,464) or multiple copy variants or fusion proteins thereof.

The antigens that may be used in the present invention may further comprise antigens derived from parasites that cause malaria. For example, antigens derived from *Plasmodia falciparum* include RTS, S and TRAP. RTS is a hybrid protein comprising substantially all the C-terminal portion of the circumsporozoite (CS) protein of *P. falciparum* linked via four amino acids of the preS2 portion of hepatitis B surface antigen to the surface (S) antigen of hepatitis B virus. Its full structure is disclosed in International Patent Application No. PCT/EP92/02591 (published under Number WO 93/10152 claiming priority from UK patent application No. 9124390.7). When expressed in yeast, RTS is produced as a lipoprotein particle, and when it is co-expressed with the S antigen from HBV, it produces a mixed particle known as RTS,S. TRAP antigens are described in International Patent Application No. PCT/GB89/00895 (published under WO 90/01496). A preferred embodiment of the present invention is a malaria vaccine wherein the antigenic preparation comprises a combination of the RTS, S and TRAP antigens. Other plasmodia antigens that are likely candidates to be components of a multistage malaria vaccine are *P. falciparum*, MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp., but are not limited thereto.

The present invention contemplates the use of an anti-tumor antigen and be useful for the immunotherapeutic treatment of cancers. For example, there are tumor rejection antigens such as those used in the treatment of prostrate, breast, colorectal, lung, pancreatic, renal or melanoma cancers. Exemplary antigens include MAGE 1, 3 and MAGE 4 or other MAGE antigens such as disclosed in WO99/40188, PRAME, BAGE, Lage (also known as NY Eos 1) SAGE and HAGE (WO 99/53061) or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p293). These antigens are expressed in a wide range of tumor types such as melanoma, lung carcinoma, sarcoma and bladder carcinoma.

MAGE antigens that are used in the present invention may be expressed as a fusion protein with an expression enhancer or an immunological fusion partner. In particular, the Mage protein may be fused to Protein D from Heamophilus influenzae B. In particular, the fusion partner may comprise the first ⅓ of Protein D. Such constructs are disclosed in WO99/40188. Other examples of fusion proteins that may contain cancer specific epitopes include, but are not limited to, bcr/abl fusion proteins.

For example, prostate antigens are used, such as prostate specific antigen (PSA), PAP, PSCA (PNAS 95(4) 1735-1740 1998), PSMA or antigen known as prostase.

Prostase is a prostate-specific serine protease (trypsin-like), 254 amino acid-long, with a conserved serine protease catalytic triad H-D-S and an amino-terminal pre-propeptide sequence, indicating a potential secretory function (P. Nelson, Lu Gan, C. Ferguson, P. Moss, R. Gelinas, L. Hood & K. Wand, "Molecular cloning and characterisation of prostase, an androgen-regulated serine protease with prostate restricted expression, In Proc. Natl. Acad. Sci. USA (1999) 96, 3114-3119). A putative glycosylation site has been described. The predicted structure is very similar to other known serine proteases, showing that the mature polypeptide folds into a single domain. The mature protein is 224 amino acids-long, with one A2 epitope shown to be naturally processed.

The present invention provides antigens comprising prostase protein fusions based on prostase protein and fragments and homologues thereof ("derivatives"). Such derivatives are suitable for use in therapeutic vaccine formulations which are suitable for the treatment of a prostate tumor. Typically, the fragment will contain at least 20, preferably at least 50, more preferably at least 100 contiguous amino acids as disclosed in the above-referenced patent and patent applications.

The present invention is also useful in combination with breast cancer antigens such as Muc-1, Muc-2, EpCAM, her 2/Neu, mammaglobin. Her 2 neu antigens are disclosed inter alia, in U.S. Pat. No. 5,801,005. For example, the Her 2 neu comprises the entire extracellular domain (comprising approximately amino acid 1-645) or fragments thereof and at least an immunogenic portion of or the entire intracellular domain approximately the C terminal 580 amino acids. In particular, the intracellular portion should comprise the phosphorylation domain or fragments thereof, but is not limited thereto.

The Her 2 neu as used herein can be derived from rats, mice or humans.

The vaccine may also contain antigens associated with tumor-support mechanisms (e.g., angiogenesis, tumor invasion), for example, tie 2, VEGF.

Antigens relevant for the prevention or treatment of patients susceptible to or suffering from Alzheimer neuro-degenerative disease are, in particular, the N terminal 39-43 amino acid fragment (ABthe amyloid precursor protein and smaller fragments).

Potential self-antigens that can be included as vaccines for auto-immune disorders or as a contraceptive vaccine include cytokines, hormones, growth factors or extracellular proteins, for example, a 4-helical cytokine, for example, IL13. Cytokines include, for example, IL1, IL2, IL3, IL4, IL5, IL6, IL7, IL8, IL9, IL10, IL11, IL12, IL13, IL14, IL15, IL16, IL17, IL18, IL20, IL21, TNF, TGF, GMCSF, MCSF and OSM. 4-helical cytokines include IL2, IL3, IL4, IL5, IL13, GMCSF and MCSF. Hormones include, for example, luteinising hormone (LH), follicle stimulating hormone (FSH), chorionic gonadotropin (CG), VGF, GHrelin, agouti, agouti related protein and neuropeptide Y. Growth factors include, for example, VEGF.

The vaccines of the present invention are particularly suited for the immunotherapeutic treatment of diseases, such as chronic conditions and cancers, but also for the treatment of persistent infections. Accordingly the vaccines of the present invention are particularly suitable for the immunotherapy of infectious diseases, such as tuberculosis (TB), HIV infections (such as AIDS) and hepatitis B virus infections.

The kind of vaccine that can be the target substance of the peptide of the present invention is not limited to the above-mentioned vaccines.

If the target substance in the composition of the present invention is a vaccine, the composition may further contain an adjuvant or immunostimulant. As used herein, the term "adjuvant" refers to any substance that is added to enhance the immunogenicity of the vaccine. Examples of the adjuvant include, but are not limited to, various oils, aluminum salts, virosomes, liposomes, LPS, bacterial cell wall components, RNA, DNA, etc. Furthermore, examples of the adjuvant include metal salt compounds, bacterial adjuvants, cytokines, lipid particle adjuvants, immunostimulatory complexes (ISCOMs), biodegradable microsphere adjuvants, nucleic acid adjuvants, etc. For example, the adjuvant is selected from the group consisting of alpha-interferon, gamma-interferon, platelet-derived growth factor (PDGF), TNFα, TNFβ, GM-CSF, epidermal growth factor (EGF), cutaneous T-cell attracting chemokine (CTACK), epithelial thymus-expressed chemokine (TECK), mucosa-associated epithelial chemokine (MEC), IL-12, IL-15, MHC, CD80, and CD86 including IL-15 having the signal sequence deleted and optionally including the signal peptide from IgE. Other genes which may be useful adjuvants include, but are not limited to, those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some embodiments, the adjuvant is selected from IL-12, IL-15, CTACK, TECK or MEC. In some embodiments, the adjuvant is a transfection facilitating agent, which can include the following: surface active agents, such as immune-stimulating complexes (ISCOMS), Freunds incomplete adjuvant, LPS analog including monophosphoryl lipid A, muramyl peptides, quinone analogs, vesicles such as squalene, hyaluronic acid, lipids, liposomes, calcium ions, viral proteins, polyanions, polycations, or nanoparticles, or other known transfection facilitating agents. For example, the transfection facilitating agent is a polyanion, polycation including poly-L-glutamate (LGS), or lipid. Preferably, the transfection facilitating agent is poly-L-glutamate, but is not limited thereto.

Adjuvants or immunostimulants, which may be contained in the compositions of the present invention, can be classified as follows, according to substances, but are not limited thereto.

A. Mineral-Containing Composition

Mineral-containing compositions suitable for use as immunostimulants in the present invention include mineral salts, such as aluminum salts and calcium salts. The present invention includes mineral salts such as hydroxides (e.g. oxyhydroxides), phosphates (e.g. hydroxyphosphates, orthophosphates), sulfates, etc., or mixtures of different mineral compounds, with the compounds taking any suitable form (e.g. gel, crystalline, amorphous, etc.), and with adsorption to the salt(s) being preferred. The mineral containing compositions may also be formulated as a particle of metal salt.

"Aluminum hydroxide" immunostimulants used as adjuvants are typically aluminum oxyhydroxide salts, which are usually at least partially crystalline. Aluminum oxyhydroxide, which can be represented by the formula AlO(OH), can be distinguished from other aluminum compounds, such as aluminum hydroxide, by infrared (IR) spectroscopy, in particular by the presence of an adsorption band at 1070 cm$^{-1}$ and a strong shoulder at 3090-3100 cm$^{-1}$.

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt.

The $PO_4/Al^{3+}$ molar ratio of an aluminum phosphate adjuvant will generally be between 0.3 to 1.2, preferably between 0.8 to 1.2, and more preferably 0.95±0.1. The aluminum phosphate will generally be amorphous, particularly for hydroxyphosphate salts.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation.

B. Oil Emulsions

Oil-emulsion compositions suitable for use as adjuvants in the present invention include squalene-water emulsions, such as MF59 (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

The emulsions in the present invention can include oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, for example, obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of the present invention. The procedures for separation, purification, saponification and other means necessary for obtaining pure oils from animal sources are well known in the art. Most fishes contain metabolizable oils which may be readily recovered. For example, cod liver oil, shark liver oils, and whale oil such as spermaceti exemplify several of the fish oils which may be used in the present invention. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene. Other preferred oils are tocopherols.

C. Saponin Formulations

Saponin formulations may also be used as adjuvants in the present invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree has been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as liquid formulations, such as ISCOMs.

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. For example, the ISCOM includes one or more of Quil A, QHA and QHC.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally nonpathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), hepatitis B virus (such as core or capsid proteins), hepatitis E virus, measles virus, Sindbis virus, Rotavirus, foot-and-mouth disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

E. Bacterial or Microbial Derivatives

Adjuvants suitable for use in the present invention include bacterial or microbial derivatives, such as non-toxic derivatives of enterobacterial lipopolysaccharide (LPS), lipid A derivatives, immunostimulatory oligonucleotides, and ADP-ribosylating toxins and detoxified derivatives thereof.

The non-toxic derivatives of LPS include monophosphoryl lipid A (MPL) and 3-O-deacylated MPL (3 dMPL). 3 dMPL is a mixture of 3 de-O-acylated monophosphoryl lipid A with 4, 5 or 6 acylated chains.

The lipid A derivatives include derivatives of lipid A from *Escherichia coli* such as OM-174.

Immunostimulatory oligonucleotides suitable for use as adjuvants in the present invention include nucleotide sequences containing a CpG motif (a dinucleotide sequence containing an unmethylated cytosine followed by guanosine and linked by a phosphate bond). Double stranded RNA and oligonucleotides containing palindromic or poly(dG) sequences have also been shown to be immunostimulatory.

The CpG's can include nucleotide modifications/analogs such as phosphorothioate modifications and can be double-stranded or single-stranded.

The CpG sequence may be directed to TLR9, such as the motif GTCGTT or TTCGTT. The CpG sequence may be specific for inducing a ThI immune response, such as a CpG-A ODN, or it may be more specific for inducing a B cell response, such a CpG-B ODN.

The CpG oligonucleotide is constructed so that the 5' end is accessible for receptor recognition. Optionally, two CpG oligonucleotide sequences may be attached at their 3' ends to form "immunomers".

A particularly useful adjuvant based around immunostimulatory oligonucleotides is known as IC-31™. Thus an adjuvant used with the present invention may comprise a mixture of (i) an oligonucleotide (e.g. between 15-40 nucleotides) including at least one (or multiple) CpI motifs (i.e. a cytosine linked to an inosine to form a dinucleotide), and (ii) a polycationic polymer, such as an oligopeptide (e.g. between 5-20 amino acids) including at least one (or multiple) Lys-Arg-Lys tripeptide sequence(s).

Bacterial ADP-ribosylating toxins and detoxified derivatives thereof may be used as adjuvants in the present invention. For example, the protein is derived from *E. coli* (i.e., *E. coli* heat labile enterotoxin "LT"), cholera ("CT"), or pertussis ("PT"). The toxin or toxoid is, for example, in the form of a holotoxin, comprising both A and B subunits. For example, the A subunit contains a detoxifying mutation, and the B subunit is not mutated. For example, the adjuvant is a detoxified LT mutant such as LT-K63, LT-R72, and LT-G192.

F. Human Immunomodulators

Human immunomodulators suitable for use as adjuvants in the present invention include cytokines, such as interleukins (e.g., IL-1, IL-2, IL-4, IL-5, IL-6, IL-7, IL-12, etc.) interferons (e.g., interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the present invention. Suitable bioadhesives include esterified hyaluronic acid microspheres or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the present invention.

H. Microparticles

Microparticles may also be used as adjuvants in the present invention. Microparticles (i.e., a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g., with SDS) or a positively-charged surface (e.g., with a cationic detergent, such as CTAB).

I. Liposomes

Liposomes may also be used as adjuvants in the present invention.

J. Polyoxyethylene Ether and Polyoxyethylene Ester Formulations

Adjuvants suitable for use in the invention include polyoxyethylene ethers and polyoxyethylene esters. Such formulations further include polyoxyethylene sorbitan ester surfactants in combination with an octoxynol as well as polyoxyethylene alkyl ethers or ester surfactants in combination with at least one additional non-ionic surfactant such as an octoxynol. For example, polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations may also be used as adjuvants in the present invention.

L. Muramyl Peptides

Examples of muramyl peptides suitable for use as adjuvants in the present invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2"-dipalmitoyl-sn-glycero-3-hydroxyphosphoryloxy)-ethylamine MTP-PE).

M. Imidazoquinolone Compounds

Examples of imidazoquinolone compounds suitable for use adjuvants in the present invention include Imiquamod and its homologues (e.g. "Resiquimod 3M").

The compositions of the present invention may elicit both a cell-mediated immune response as well as a humoral immune response.

In one embodiment of the present invention, the adjuvant may be a DNA adjuvant, for example, CpG (unmethylated CpG dinuceotide).

The kind of adjuvant or immunostimulant that may be used in the present invention is not limited to the above-described examples.

Still another aspect of the present invention is a composition for delivering a target substance into the brain, the composition comprising: a peptide consisting of the following amino acid sequence; and a target substance:

R1-R2-R3-R4-R5-R6-R7-R8-R9-R10 wherein

R1 is any one amino acid selected from M, L, P, Q, C, F or W,

R2 is any one amino acid selected from I, A, L, P or H,

R3 is any one amino acid selected from I, L, A, P or H,

R4 is any one amino acid selected from F, E, A, L, P, H, Y, S or R,

R5 is any one amino acid selected from A, R or K,

R6 is any one amino acid selected from A, M, I, P, H, L, R or D,

R7 is any one amino acid selected from L, A, P, H, K, R or E,

R8 is any one amino acid selected from I, L, A, P, H or K,

R9 is any one amino acid selected from T, S, E or Y, and

R10 is any one amino acid selected from H, K, R, P, L or E, and no amino acid is added to R10, or any one amino acid sequence selected from R, RR, HH, K, KK, KKK and KKKK may be added to R10.

In one embodiment of the present invention, the peptide may consist of any one amino acid sequence selected from the group consisting of SEQ ID NOs: 1 to 61. Particularly, the scope of the peptide according to the present invention includes variants of the peptide comprising the amino acid sequence of SEQ ID NO: 27, in which the variants are peptides which commonly comprise a 'MIIFR' sequence, L at position 7 and H at position 10 of the amino acid sequence and in which one or more of the amino acids at positions 6, 8 and 9 of the amino acid sequence of SEQ ID NO: 27 are substituted. Specifically, the variants are those in which A at position 6 of the amino acid sequence of SEQ ID NO: 27 is substituted with L, I at position 8 of the amino acid sequence is A, or S at position 9 of the amino acid sequence is substituted with Y. More specifically, the variant may be a peptide consisting of an amino acid sequence of SEQ ID NO: 22, 24, 18 or 27, but is not limited thereto. Synthesis, preparation and modification of the peptide and a composition comprising the peptide are as described above.

In the present invention, the peptide may be a D-form or L-form peptide, or a peptide, only a portion of the sequence of which consists of a D-form or L-form peptide, or a racemic form thereof. Furthermore, the complex may be a fusion protein of the peptide and the target substance, and in this case, the peptide and the target substance are linked to each other by a linker, but the scope of the present invention is not limited.

In one embodiment of the present invention, the target substance may be leptin or [D-Leu-4]-OB3.

The "leptin" is a 16-kDa protein hormone that plays a key role in regulating energy intake and expenditure, including appetite and hunger, metabolism, and behavior, and is secreted from adipose tissue. When leptin reaches the brain, it results in decreases in percent body fat, food intake and blood glucose levels, and results in an increase in metabolic efficiency or activity, leading to a slow decrease in body weight. A decrease in leptin secretion leads to the development of obesity and diabetes.

[D-Leu-4]-OB3 is a synthetic peptide amide with leptin-like activity. [D-Leu-4]-OB3 is known to exhibit the effects of reducing body weight, food intake and blood glucose levels. Furthermore, [D-Leu-4]-OB3 was reported to augment the effects of exenatide and pramlintide acetate on energy balance and glycemic control (Leinung Matthew C, Grasso Patricia, [d-Leu-4]-OB3, a synthetic peptide amide with leptin-like activity, augments the effects of orally delivered exenatide and pramlintide acetate on energy balance and glycemic control in insulin-resistant male C57BLK/6-m db/db mice, Regulatory Peptides Vol. 179 No. 1-3 33 p~38 p 0167-0115 SCI(E)).

Moreover, the target substance may be a therapeutic agent for one or more selected from the group consisting of diabetes, obesity, metabolic disease, dementia, osteoporosis, Alzheimer's disease, Parkinson's disease, stroke, central nervous disease, and peripheral nervous disease, but is not limited thereto. Thus, the scope of the present invention may include a method for preventing or treating diabetes, obesity, metabolic disease, dementia, osteoporosis, Alzheimer's disease, Parkinson's disease, stroke, central nervous disease, or peripheral nervous disease, comprising administering a composition comprising: the peptide; and leptin or [D-Leu-4]-OB3.

Still another aspect of the present invention is a formulation, comprising: a peptide represented by the amino acid sequence of any one of SEQ ID NOs: 1 to 61; and a target substance. Namely, the present invention provides a formulation, comprising a complex of the above-described TCTP-PTD peptide or a variant thereof and a target substance. The target substance may be, for example, insulin, but is not limited thereto.

The formulation may be any one or more selected from the group consisting of oral formulations, injectable formulations, formulations for oral mucosal administration, formulations for nasal administration, ocular formulations, formulation for vaginal administration, inhalation formulations, formulations for external use, formulation for transdermal absorption, formulations for sublingual administration, formulations for implantation, and suppositories. Specifically, it may be formulations for nasal administration, but is not limited thereto.

In addition, the formulation of the present invention may further contain, in addition to the peptide and the target substance, a drug showing a different effect, and may further contain a pharmaceutically acceptable carrier. For oral administration, the pharmaceutically acceptable carrier may be one or more selected from binders, lubricants, disintegrants, excipients, solubilizing agents, dispersing agents, stabilizers, suspending agents, pigments, fragrances, and the like. For injection, the pharmaceutically acceptable carrier may be one or more selected from buffers, preservatives, soothing agents, solubilizing agents, isotonic agents, stabilizers, and the like. For topical administration, the pharmaceutically acceptable carrier may be one or more selected from bases, excipients, lubricants, preservatives, antioxidants, stabilizers, buffers, thickeners, isotonic agents, solubilizing agents, anti-coagulating agents, surfactants, and the like. The carrier for use in the present invention is not limited to the above-described examples. Specifically, the formulation may contain one or more selected from the group consisting of protein stabilizers, surfactants and anti-oxidants. In addition, the formulation may contain or not contain a protein aggregation inhibitor. For example, the formulation may contain sucrose, poloxamer and methionine, but is not limited thereto. For example, the formulation may contain the TCTP-PTD peptide or its variant at a concentration of 0.23-0.27 mM, the composition and contents of the peptide or complex, carriers and excipients in the formulation are not limited.

In one embodiment of the present invention, the formulation may further contain buffer. In addition, the formulation of the present invention may further contain a pharmaceutically acceptable carrier suitable for cell membrane penetration of the target substance. In addition, the formulation may further contain components capable of enhancing stability, such as a preservative and an antioxidant, a component capable of improving the solubility or aggregation of the target substance, a component of controlling the monomer/multimer ratio of a drug, a component capable of controlling the duration or absorption rate of a drug, an isotonic agent, a thickener, a buffer, a stabilizer, etc., but the scope of the present invention is not limited to these examples.

The pH of the composition or formulation of the present invention is not limited, and may vary depending on the kind of target substance, the route of administration, a subject to be administered with the composition or formulation of the present invention, etc. For example, the pH of the composition or formulation of the present invention may be 10 or less, for example, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0. Particularly the pH may range from 6.0 to 7.5, but is not limited thereto.

The method for administering the composition or formulation of the present invention is not particularly limited. For example, the composition or formulation of the present invention in a dry state or a solution state may be administered, or the composition or formulation in a dry state may be administered after dissolution or dispersion in water.

The composition or formulation of the present invention may further contain one or more selected from conventional fillers, extenders, binders, disintegrants, surfactants, anti-aggregation agents, lubricants, wetting agents, fragrances, isotonic agents, thickeners, buffers, stabilizers, preservatives, antioxidants, release-controlling agents, emulsifiers, and preservatives, but is not limited thereto.

The composition or formulation of the present invention may be administered orally or parenterally. Solid formulations for oral administration include, but are not limited to, tablets, pills, powders, granules and capsules.

Liquid formulations for oral administration include, but are not limited to, suspensions, solutions, emulsions and syrups.

Formulations for parenteral administration include, but are not limited to, sterile aqueous solutions, non-aqueous solutions, suspensions, emulsions, freeze-dried formulations, and suppositories. When the composition or formulation of the present invention is administered parenterally, it may be administered by subcutaneous injection, intravenous injection or intramuscular injection, but the route of administration is not limited thereto.

The dose or number of administrations of the composition or formulation of the present invention may be suitably selected depending on various factors, including the mode of administration, the patient's age and body weight, and the severity of the disease. Preferably, it may be administered at a dose ranging from 0.01 μg to 10 g, for example, from 0.01 mg to 50 mg, for an adult weighing 70 kg. However, the dose is illustrative only and is not limited thereto.

The present invention also provides a method for preparing a formulation, comprising a step of preparing a complex of a peptide consisting of an amino acid sequence of any one of SEQ ID NOs: 1 to 61 and a target substance.

The present invention also provides a method for increasing the ability of a target substance to penetrate the cell membrane or tissue, the method comprising administered to a subject the target substance together with a peptide represented by an amino acid sequence selected from the group consisting of SEQ ID NOs: 1 to 61.

The present invention also provides the use of a peptide, represented by an amino acid sequence selected from the group consisting of SEQ ID NOs: 1 to 61, for improving the ability of a target substance to penetrate the cell membrane.

MODE FOR THE INVENTION

Hereinafter, the present invention will be described in detail with reference to examples. It is to be understood, however, that these examples are for illustrative purposes only and are not intended to limit the scope of the present invention.

Example 1

Preparation of Variant TCTP-PTD Peptides

Based on the TCTP-PTD peptide of SEQ ID NO: 27 (hereinafter referred to as TCTP-PTD 13; Korean Patent No. 10-0859972), 60 different variant TCTP-PTD peptides were prepared. The sequences of the TCTP-PTD peptides and the nucleic acid sequences thereof are shown in Table 1 below.

TABLE 1

| Peptide SEQ ID NO | Nucleic acid sequence No |
|---|---|
| 1 | 62 |
| 2 | 63 |
| 3 | 64 |
| 4 | 65 |
| 5 | 66 |
| 6 | 67 |

TABLE 1-continued

| Peptide SEQ ID NO | Nucleic acid sequence No |
|---|---|
| 7 | 68 |
| 8 | 69 |
| 9 | 70 |
| 10 | 71 |
| 11 | 72 |
| 12 | 73 |
| 13 | 74 |
| 14 | 75 |
| 15 | 76 |
| 16 | 77 |
| 17 | 78 |
| 18 | 78 |
| 19 | 80 |
| 20 | 81 |
| 21 | 82 |
| 22 | 83 |
| 23 | 84 |
| 24 | 85 |
| 25 | 86 |
| 26 | 87 |
| 27 | 88 |
| 28 | 89 |
| 29 | 90 |
| 30 | 91 |
| 31 | 92 |
| 32 | 93 |
| 33 | 94 |
| 34 | 95 |
| 35 | 96 |
| 36 | 97 |
| 37 | 98 |
| 38 | 99 |
| 39 | 100 |
| 40 | 101 |
| 41 | 102 |
| 42 | 103 |
| 43 | 104 |
| 44 | 105 |
| 45 | 106 |
| 46 | 107 |
| 47 | 108 |
| 48 | 109 |
| 49 | 110 |
| 50 | 111 |
| 51 | 112 |
| 52 | 113 |
| 53 | 114 |
| 54 | 115 |
| 55 | 116 |
| 56 | 117 |
| 57 | 118 |
| 58 | 119 |
| 59 | 120 |
| 60 | 121 |
| 61 | 122 |

Each of the peptides was prepared with a purity of 95% or higher, and synthesis of the peptides was performed by PEPTRON Inc. In addition, in the case of SEQ ID Nos. 22, 24, 18 and 27, L-form and D-form peptides were prepared separately.

Example 2

Evaluation of the Ability of TCTP-PTD to Penetrate Cell Membrane 2-1: Evaluation of the Ability of TCTP-PTD Peptides to Penetrate Cell Membrane The cervical cancer cell line HeLa was prepared. To detect TCTP-PTD accumulated in cells after passage through the cell membrane, the N-terminus of the synthesized peptide was labeled with FITC (fluorescein isothicyanate). Then, the cervical cancer cell line Hela was treated with 10 μM of the FITC-labeled TCTP-PTD of SEQ ID NO: 18, SEQ ID NO: 22, SEQ ID NO: 24 or SEQ ID NO: 27 for 15 minutes. After completion of the incubation, the cells were washed three times with PBS to remove FITC-TCTP-PTD remaining on the cell membrane of the HeLa cells. 500 μl of PBS was added, and then the fluorescence intensity of the FITC was measured with a fluorescence reader at 495 nm and 517 nm.

As a result, a high level of fluorescence was observed in all the treated groups, suggesting that all the TCTP-PTD peptides of SEQ ID NOs: 18, 22, 24 and 27 easily penetrated the cell membrane of the cervical cancer cells (FIG. 1).

2-2: Evaluation of Cell Membrane Penetration Ability According to Amino Acid Type The human bronchial epithelial cell line BEAS-2B was prepared, and the cell membrane penetration ability of the TCTP-PTD peptide according to the amino acid type was analyzed by flow cytometry. Specifically, BEAS-2B cells were seeded on a 6-well plate at a density of $8 \times 10^5$ cells/well, and then cultured in cell culture medium (BEGM) for 24 hours. After 24 hours of cell culture, each well was washed twice with PBS, and then each well was treated with FITC-labeled L-form TCTP-PTD 13 (hereinafter referred to as L-PTD 13; SEQ ID NO: 27) or FITC-labeled D-form TCTP-PTD 13 (hereinafter referred to as D-PTD 13; SEQ ID NO: 27) diluted in cell culture medium such that the concentration of each TCTP-PTD would be 2.5 μM. 30 minutes after the cells were treated with the two kinds of TCTP-PTD 13, the cells were isolated from each well by use of 0.25% trypsin, and then washed 6 times with cold PBS to remove TCTP-PTD from the cell surface. TCTP-PTD that accumulated in the cells was analyzed using FACSCalibur (BD, USA), and as a result, it was shown that both D-PTD 13 and L-PTD 13 had an excellent ability to penetrate the cell membrane (FIG. 2).

Example 3

Effect of TCTP-PTD on Improvement in Cell Membrane Penetration of Insulin 3-1: Blood Glucose-Lowering Effect of TCTP-PTD/Insulin Mixture in Non-Diabetic Mice Male BALB/c mice (non-diabetic mice) weighing 20-23 g were used as experimental animals. The mice were fasted overnight, and then the blood glucose levels in the mice were measured using a blood glucose meter. The blood glucose level of the mice in the fasted state was about 100 mg/dL, and this blood glucose level was used as an initial blood glucose value (100%). The mice were anesthetized by intraperitoneal injection of sodium pentobarbital (60 mg/kg).

In 5 mM phosphate buffer (pH 7.8), insulin was mixed with each of the TCTP-PTD peptides of SEQ ID NOs: 1, 12, 17, 18 and 22 at a molar ratio of 1:2 to prepare mixtures. At 60 mM and 90 mM after intranasal administration of each of the insulin/variant TCTP-PTD mixtures to the mice (insulin dose: 1 IU/kg), the blood glucose levels were measured.

The mean values of the blood glucose levels at 60 min and 90 mM after administration are graphically shown in FIG. 3 (SEQ ID NO: 1), FIG. 4 (SEQ ID NOIs: 12, 17 and 22) and FIG. 5 (SEQ ID NO: 18). As can be seen in FIGS. 3 to 5, the blood glucose lowering effect was better in the groups treated with the insulin/TCTP-PTD mixtures than in the group treated with insulin alone. These results suggest that the TCTP-PTD of the present invention increases the ability of insulin to penetrate nasal mucosal epithelial cells to thereby increase the blood glucose lowering effect of insulin upon intranasal administration.

3-2: Evaluation of Blood Glucose-Lowering Effect of TCTP-PTD/Insulin Mixture in Type 1 Diabetic Model Mice Streptozotocin (STZ) was injected intraperitoneally into male ICR mice (body weight: 33-34.5 g) four times (doses: 100, 50, 50 and 50 mg/kg) at 2-day intervals to induce type 1 diabetes. At 7 days after last administration of STZ, mice having a blood glucose level of 300-350 mg/dL were selected as experimental animals.

In 5 mM phosphate buffer (pH 5), insulin and each of the TCTP-PTD peptides of SEQ ID NOs: 18, 22, 24 and 27, synthesized in Example 1, were mixed at a molar ratio of 1:2 and dissolved to final concentrations of 50 μM and 100 μM, respectively, to thereby prepare mixtures. Each of the insulin/TCTP-PTD mixtures was administered intranasally to the mice (insulin dose: 2 IU/kg). A control group was injected subcutaneously with 1 IU/kg of insulin. For 240 minutes after administration, the blood glucose levels were monitored.

The results are shown in FIG. 6. As can be seen in FIG. 6, when the mixture of insulin and each TCTP-PTD (insulin/SEQ ID NO: 22, insulin/SEQ ID NO: 24, or insulin/SEQ ID NO: 18) was administered, the blood glucose level was reduced, and the blood glucose level decreased to the lowest level at 90-120 minutes after administration, in the same manner as when insulin was injected subcutaneously. Furthermore, the ability of SEQ ID NOs: 18, 22 and 24 to deliver insulin was better than that of SEQ ID NO: 27. However, when insulin alone was administered intranasally, there was no significant change in the blood glucose level.

3-3: Measurement of Plasma Insulin Concentration after Intranasal Administration of Insulin Male Wistar rats weighing 180-190 g were used as experimental animals and anesthetized in the same manner as described above.

In 5 mM phosphate buffer (pH 5), insulin and each of the TCTP-PTD peptides of SEQ ID NOs: 18, 22, 24 and 27, synthesized in Example 1, were mixed at final concentrations of 50 μM and 100 μM, respectively, thereby preparing mixtures. Each of the insulin/TCTP-PTD mixtures was administered intranasally to the anesthetized mice (insulin dose: 0.5 IU/kg). A control group was injected subcutaneously with 0.25 IU/kg of insulin. At 5, 10, 20, 30, 60, 90, 120 and 180 min after administration, the blood was collected, and then plasma was separated from the collected blood, and the concentration of insulin in the plasma was measured using a commercial ELISA kit.

The results of the measurement are shown in FIG. 7. As shown in FIG. 7, the TCTP-PTD peptides of SEQ ID NOs: 18, 22 and 24 all increased insulin uptake compared to the TCTP-PTD of SEQ ID NO: 27. However, in the case in which insulin was intranasally administered alone, there was little or no change in the blood insulin concentration, suggesting that little or no insulin was delivered into the body. When the bioavailability upon subcutaneous administration of insulin was taken as 100%, the relative bioavailability in the groups administered intranasally with the insulin/TCTP-PTD was 25.9% in the group treated with insulin/SEQ ID NO: 27, 28.2% in the group treated with insulin/SEQ ID NO: 22, 70.9% in the group treated with insulin/SEQ ID NO: 24, and 43% in the group treated with insulin/SEQ ID NO: 18.

Example 4

The Effect of TCTP-PTD on Improvement in Cell Membrane Penetration of Exendin-4

4-1: Evaluation of Blood Glucose-Lowering Effect of TCTP-PTD/Ex-4 Mixture in Non-Diabetic Mice Male ICR mice (non-diabetic mice) weighing 33-35 g were used as experimental animals and anesthetized by intraperitoneal injection of the anesthetic sodium pentobarbital (60 mg/kg).

Exendin-4 (exenatide, Ex-4) and each of the TCTP-PTD peptides of SEQ ID NOs: 1, 18, 27, 42 and 46, synthesized in Example 1, were dissolved in PBS buffer at a molar ratio of 1:2 to final concentrations of 14.3 μM and 28.6 μM, respectively, thereby preparing mixtures.

Each of the prepared Ex-4/TCTP-PTD mixtures was administered intranasally to the mice (Ex-4 dose: 20 μg/kg), and a control group was administered intranasally with the same amount of Ex-4, and a negative control group was administered intranasally with the same amount of PBS. After 15 minutes, glucose (2 g/kg) was injected intraperitoneally, and after 60 minutes (at which the peak blood glucose level was reached), the blood glucose-lowering effect of Ex-4 in each treated group was evaluated.

The results are shown in FIG. 8. As can be seen in FIG. 8, the blood glucose-lowering effect was better in the groups treated with the Ex-4/TCTP-PTD mixture than in the group administered with Ex-4 alone. These results suggest that the TCTP-PTD of the present invention enhances the uptake of Ex-4 into nasal mucosal epithelial cells to thereby increase the blood glucose-lowering effect of Ex-4.

4-2: Blood Glucose-Lowering Effect of TCTP-PTD/Ex-4 Mixture in Type 2 Diabetic Model Mice Male db/db mice weighing 31-34 g were used as experimental animals. The mice were fasted overnight, and then the blood glucose level in the mice were measured using a blood glucose meter. As a result, the blood glucose level in the mice in the fasted state was shown to be 200-230 mg/dL. Next, the mice were anesthetized in the same manner as described in Example 4-1.

Each of the TCTP-PTD peptides of SEQ ID NOs: 18, 22, 24 and 27, synthesized in Example 1, and EX-4 were dissolved in PBS to prepare mixtures (the final concentration of TCTP-PTD and EX-4 were 20 μM and 10 μM, respectively). 20 minutes after anesthesia, each of the prepared Ex-4/TCTP-PTD mixtures was administered intranasally to the mice (Ex-4 dose: 10 μg/kg), and a control group was administered intranasally with the same amount of Ex-4, and a negative control group was administered intranasally with the same amount of PBS. After 15 minutes, glucose (2.5 g/kg) was injected intraperitoneally to the mice, and the blood glucose level in the mice was monitored for 240 minutes.

The results are shown in FIG. 9. As can be seen in FIG. 9, the PBS-treated negative control group and the group treated with Ex-4 alone showed a great increase in the blood glucose level. However, in the case in which the Ex-4/TCTP-PTD mixture was administered, a great change in the blood glucose level did not appear, even when glucose was administered intraperitoneally. Particularly, the TCTP-PTD peptides of SEQ ID NOs: 18, 22 and 24 showed an excellent effect of lowering the blood glucose level.

Using the results shown in FIG. 9, the Area Under the Curve (AUC) of the blood glucose level was calculated, and the mean value of each treated group was calculated. The AUC was calculated using the trapezoidal rule (Shen et al., 1999).

As the blood glucose level decreases, the AUC decreases, indicating that the uptake rate of Ex-4 in the nasal mucosal membrane increases. As can be seen in FIG. 10, the AUC was lower in the group treated with the Ex-4/TCTP-PTD than in the group treated with Ex-4, and particularly, the AUC was lower in the case of the TCTP-PTD peptides of SEQ ID NOs: 18, 22 and 24.

From the results in FIGS. 9 and 10, the TCTP-PTD peptides of SEQ ID NOs: 18, 22, 24 and 27 enhances the ability of Ex-4 to penetrate the nasal mucosal membrane to thereby increase the blood glucose-lowering effect of Ex-4 upon nasal administration.

4-3: Evaluation of Pharmacokinetic Profile of Ex-4/TCTP-PTD Mixture

Male Wistar rats weighing 180-200 g were used as experimental animals. In buffer (pH 6.4), Ex-4 and 200 μM of each of the TCTP-PTD peptides of SEQ ID NOs: 18, 22, 24 and 27 were mixed at a molecular ratio of 1:2. The intranasal dose of Ex-4 was 30 μg per body weight of each rat, and BA % was compared with that of the group injected subcutaneously with Ex-4 (10 μg/kg). All the values were expressed as mean±SEM, and statistical analysis was performed using one-way ANOVA by Tukey's multiple-comparison test (significance: p<0.05). The results are shown in Table 2 below.

TABLE 2

| Formulation | $T_{max}$ (min) | $C_{max}$ (% baseline) | AUC (μU h/mL) | BA (%) |
|---|---|---|---|---|
| Exendin-4 | 14 ± 2.4 | 0.7 ± 0.0 | 30.0 ± 5.5 | 1.6 ± 0.3 |
| Exendin-4/SEQ ID NO: 27 | 16 ± 2.4 | 3.0 ± 0.5 [a] | 221.2 ± 36.9 [a] | 11.4 ± 1.9 [a] |
| Exendin-4/SEQ ID NO: 22 | 20 ± 0.0 | 6.4 ± 1.1 [a] | 403.2 ± 66.6 [a] | 20.7 ± 3.7 [a] |
| Exendin-4/SEQ ID NO: 24 | 16.7 ± 2.0 | 13.6 ± 1.8 [a, b] | 614.0 ± 77.0 [a, b] | 31.5 ± 4.0 [a, b] |
| Exendin-4/SEQ ID NO: 18 | 16 ± 2.4 | 11.9 ± 1.0 [a, b] | 570.8 ± 93.0 [a, b] | 29.3 ± 4.8 [a, b] |

Data: mean ± SEM (n = 5-6)
$T_{max}$: time to reach maximum concentration $C_{max}$;
$C_{max}$: maximum concentration;
AUC: area under the curve;
BA: relative bioavailability compared with s.c.;
s.c.: subcutaneous?
[a] significantly different from nasal administration of exendin-4 at p < 0.05
[b] significantly different from nasal administration of exendin-4/SEQ ID NO: 27 at p < 0.05

As a result, the group treated with Ex-4/SEQ ID NO: 22, Ex-4/SEQ ID NO: 24 or Ex-4/SEQ ID NO: 18 showed improved results compared to the group treated with Ex-4/SEQ ID NO: 27. BA % was 1.6% in the group treated with Ex-4 alone, 11.4% in the group treated with Ex-4/SEQ ID NO: 27, 20.7% in the group treated with Ex-4/SEQ ID NO: 22, 31.5% in the group treated with Ex-4/SEQ ID NO: 24, and 29.3% in the group treated with Ex-4/SEQ ID NO: 18. BA % in the group treated with Ex-4/SEQ ID NO: 24, which showed the best effect, was 2.7-fold higher than that in the group treated with Ex-4/SEQ ID NO: 27 (p<0.05) (FIG. 11).

From the above results, it could be seen that the Ex-4/TCTP-PTD mixture have the effect of improving the bioavailability and efficacy of Ex-4 upon intranasal administration.

Example 5

Evaluation of the Ability of TCTP-PTD to Penetrate Hair Follicle 5-1: Evaluation of the Ability of TCTP-PTD Variant to Penetrate Hair Follicle Hair follicle is a skin organ that makes hair, and functions to surround the root of hair in the dermis and supply nutrients. If the TCTP-PTD of the present invention can penetrate the hair follicle, drug delivery into the hair follicle will also be possible. Thus, in this Example, whether the TCTP-PTD penetrates the skin's hair follicle was examined in the following manner.

The amino-terminus of each of the TCTP-PTD peptides of SEQ ID NOs: 1, 12, 17, 18, 22 and 24 was labeled with FITC (green fluorescence), and then each TCTP-PTD was dissolved in PBS (phosphate buffered saline, pH 7.4) to a final concentration of 100 μM.

Male BALB/c mice (7-8-week-old) were prepared, and the abdominal region of the mice was shaved. Next, the mice were anesthetized by intraperitoneal injection of urethane (1.2-1.5 g/kg), and then 100 μl of each TCTP-PTD peptide solution was applied to the abdominal region of each mouse so as to be administered transdermally. Each of the peptide solutions was applied to an area of 1 cm².

2 hours after transdermal administration, the skin tissue was collected, fixed with 10% formalin for about 24 hours, and then treated with 30% sucrose solution for 4 hours. The pretreated skin tissue was immersed in OCT-compound, and then treated with liquid nitrogen to prepare a frozen block. The skin tissue was sectioned to a thickness of 20 μm by use of a cryotome and attached to a slide. The slide having the skin tissue attached thereto was washed five times with PBS, and then the nucleus was stained with DAPI (blue fluorescence). The PTD that penetrated the skin was observed with a fluorescence microscope.

As a result, it could be seen that the TCTP-PTD peptides all reached the hair follicle and dermis of the skin (FIG. 12).

5-2: Evaluation of Hair Follicle Penetration of TCTP-PTD according to Amino Acid Type The amino terminus of L-PTD 13 or D-PTD 13 was labeled with FITC (green fluorescence), and then each PTD peptide was dissolved in PBS (phosphate buffered saline, pH 7.4) to a final concentration of 100 μM.

Male BALB/c mice (7-8-week-old) were prepared, and the abdominal region of the mice was shaved. Next, the mice were anesthetized by intraperitoneal injection of urethane (1.2-1.5 g/kg), and then 100 μl of each of the FITC-labeled L-PTD 13 or D-PTD 13 solution was applied to the abdominal region of each mouse so as to be administered transdermally. Each of the peptide solutions was applied to an area of 1 cm².

2 hours after transdermal administration, the skin tissue was collected, fixed with 10% formalin for about 24 hours, and then treated with 30% sucrose solution for 4 hours. The pretreated skin tissue was immersed in OCT-compound, and then treated with liquid nitrogen to prepare a frozen block. The skin tissue was sectioned to a thickness of 20 μm by use of a cryotome and attached to a slide. The slide having the skin tissue attached thereto was washed five times with PBS, and then the nucleus was stained with DAPI (blue fluorescence). The PTD that penetrated the skin was observed with a fluorescence microscope.

As a result, it could be seen that L-PTD 13 and D-PTD 13 all reached the hair follicle and dermis of the skin (FIG. 13).

Example 6

Delivery of Vaccine by TCTP-PTD

OVA (ovalbumin) having a molecular weight of 45 kDa was selected as a model antigen for vaccination, and the ability of OVA to penetrate the nasal mucosal membrane would be increased by TCTP-PTD 13 was examined.

6-1: Preparation of OVA/TCTP-PTD 13 Mixture

First, OVA and L-PTD 13 or D-PTD 13 were dissolved in PBS (phosphate buffered saline, pH 7.4) such that the concentrations of OVA and TCTP-PTD would be 10 μM and 300 μM, respectively, thereby preparing mixtures. Herein, OVA and TCTP-PTD were mixed at a molar ratio of 1:30.

6-2: Examination of the Ability to Penetrate Nasal Mucosal Epithelial Cells

Female BALB/c mice (6-8-week-old) were anesthetized by intraperitoneal injection of 50 mg/kg of zoletil and 10 mg/kg of xylazine.

10 μl of OVA, the OVA/D-PTD 13 mixture or the OVA/L-PTD 13 mixture was administered intranasally to each of the anesthetized mice. A control group was administered with 4.5 μg of OVA alone.

15 minutes after intranasal administration, the nasal tissue was collected. The collected nasal tissue was fixed with 10% formalin for about 24 hours, and then decalcified using 4 M formic acid at 4° C. for 30 hours. After decalcification, the nasal tissue was embedded in paraffin according to a conventional method, sectioned to a thickness of 5 μm, and attached to a slide. The slide having the nasal tissue attached thereto was deparaffinized and dehydrated with xylene and ethanol, and then immersed in 10% formic acid for 15 minutes to retrieve the antigenicity. The slide was washed with PBS, and then incubated in 2.5% normal horse serum for 30 minutes in order to block non-specific reactions, after which it was incubated overnight with a 1:200 dilution of primary antibody (OVA-specific rabbit antiserum, Sigma-Aldrich) at 4° C. After incubation with the primary antibody, the slide was washed with PBS, and then incubated with a 1:100 dilution of secondary antibody (green fluorescence; Alexa 488-conjugated secondary antibodies, Invitrogen) at room temperature for 1 hour. The slide was washed with PBS, and then the nucleus was stained with DAPI (blue fluorescence), followed by observation with a fluorescence microscope.

The results are shown in FIG. 14 (the top of FIG. 14: a cross-sectional view of the nasal sinus; the bottom of FIG. 14: an enlarged view of the top view). FIG. 14a shows a control group administered with OVA alone. In FIG. 14a, fluorescence was observed only in the nasal cavity, and was not substantially observed inside the nasal mucosal membrane. FIG. 14b shows the group administered with the OVA/L-PTD 13 mixture. In FIG. 14b, fluorescence was observed inside the nasal mucosal membrane. FIG. 14c shows the group administered with the OVA/D-PTD 13 mixture, and in FIG. 14c, fluorescence was observed inside the nasal mucosal membrane. From the above results, it could be seen that the L-PTD 13 and D-PTD 13 of the present invention have the effect of penetrating and delivering the antigen (OVA) into the nasal mucosal membrane.

6-3: Evaluation of Antigen-Specific Mucosal Immune Response and Systemic Immune Response OVA and TCTP-PTD 13 were mixed at various molar ratios to prepare mixtures. Each of the mixtures was administered to mice, and an OVA-specific mucosal immune response and systemic immune response appeared in the mice was examined.

(1) Preparation of OVA/TCTP-PTD 13 Mixtures

First, OVA and L-PTD 13, or D-PTD 13 and OVA, were mixed in PBS at molar ratios of 1:15 and 1:30 (OVA: L-PTD 13 or D-PTD 13) in a state in which the concentration of OVA was set at 10 μM, thereby preparing mixtures.

(2) Evaluation of Mucosal Immune Response and Systemic Immune Response

Female BALB/c mice (6-8-week-old) were divided into several groups, each consisting of 5 mice. The mice were anesthetized in the same manner as described in Example 6-2, and the OVA/L-PTD 13 mixture or OVA/D-PTD 13 mixture (1:15 or 1:30 molar ratio) prepared in Example 6-3(1) was administered intranasally to the mice. A control group was administered intranasally with 4.5 μg of OVA alone. Meanwhile, a positive control group was injected intramuscularly with 4.5 μg of OVA.

3 weeks after administration, the same amount of OVA or the OVA/TCTP-PTD mixture was re-inoculated intranasally into the mice. 3 weeks after re-inoculation, the plasma of each mouse and a nasal wash obtained by washing the mouse nasal cavity with 250 μl of PBS were collected in order to confirm systemic immune responses and mucosal immune responses.

According to a conventional ELISA method, IgG in the plasma and antigen-specific secretory IgA in the nasal wash were measured. Specifically, each well of an ELISA plate (96-well) was coated overnight with 100 μl (OVA, 10 μg/ml) of 50 mM sodium carbonate (pH 9.6) at 4° C. The plate was washed three times with washing buffer (0.05% (v/v) Tween 20, 0.14 M NaCl, 50 mM Tris-HCl, pH 7.4). After washing the plate, each well of the plate was blocked with 200 μl of blocking buffer (0.14 M NaCl, 50 mM Tris-HCl at pH 7.4 with 1% (v/v) bovine serum albumin) for 30 minutes in order to block nonspecific binding. After removal of the blocking buffer, in order to measure antigen-specific IgG titer in the plasma, a plasma sample obtained by ½-fold serial dilution was added to each well and incubated for 1 hour, and in order to measure antigen-specific secretory IgA in the nasal wash, 100 μl of the nasal wash was added to each well and incubated for 1 hour. Next, the plate was washed three times with washing buffer, and then 100 μl of a 1:20,000 dilution of secondary antibody (HRP-conjugated goat anti-mouse IgG, Bethyl) was added to each well and incubated for 1 hour to detect antigen-specific IgG in the plasma. To detect antigen-specific secretory IgA in the nasal wash, 100 μl of a 1:10,000 dilution of secondary antibody (HRP-conjugated goat anti-mouse IgA, Sigma) was added to each well and incubated for 1 hour. Next, the plate was washed five times with washing buffer, and then 100 μl of TMB solution, a substrate for HRP, was added to each well and incubated, after which 100 μl of 0.2 M H$_2$SO$_4$ was added to each well to stop the reaction. Next, the absorbance at 450 nm was measured with an ELISA reader.

As a result, it was shown that the mean value of antigen-specific IgG titers in the plasma of all the groups treated with the OVA/TCTP-PTD mixture was higher than that of the control group administered intranasally with OVA alone (FIG. 15). Particularly, antigen-specific IgG was more detected in the plasma of the group administered with the OVA/D-PTD mixture (1:15 or 1:30 molar ratio) than in the positive control group administered intramuscularly with OVA.

The secretory IgG in the nasal wash was more detected in the group administered with the OVA/D-PTD or OVA/L-PTD mixture than in the positive control group administered intramuscularly with OVA (FIG. 16). Particularly, in the group treated with the OVA/D-PTD mixture (1:15 or 1:30 molar ratio), antigen-specific secretory IgA was significantly more detected.

From the results in FIGS. 15 and 16, it can be seen that the TCTP-PTD 13 of the present invention has an excellent effect of delivering the antigen into the nasal cavity to induce a systemic immune response and a mucosal immune response.

6-4: Induction and Evaluation of Antigen-Specific Mucosal and Systemic Immune Responses after Intranasal Administration of OVA/CpG/PTD Mixture A mixture obtained by adding the DNA adjuvant CpG to the OVA/TCTP-PTD 13 mixture was administered intranasally to mice, and then the effect of inducing antigen-specific mucosal immune responses and systemic immune responses was examined.

(1) Preparation of OVA/CpG/PTD Mixture

CpG (SEQ ID NO: 123; 5'-tcgtcgttttgtcgttttgtcgtt-3') was purchased from InvivoGen (ODN 2006).

The concentration of OVA was set at 10 μM, and OVA, CpG and D-PTD 13 were mixed in PBS at molar ratios of 1:1:30, 1:3:30 and 1:6:30, thereby preparing OVA/CpG/PTD mixtures.

(2) Evaluation of Mucosal Immune Response and Systemic Immune Response

Female BALB/c mice (6-8-week-old) were divided into several groups, each consisting of 5-6 mice. The mice were anesthetized in the same manner as described in 6-2, and 4.5 μg of OVA, the OVA/D-PTD 13 mixture or 10 μg of the OVA/CpG/PTD was administered intranasally to each mouse. In addition, a positive control group was injected intramuscularly with 4.5 μg of OVA.

3 weeks after administration, the same amount of OVA, the OVA/D-PTD 13 mixture or the OVA/CpG/PTD mixture was re-inoculated intranasally to each mouse. 3 weeks after re-inoculation, the plasma of each mouse and a nasal wash obtained by washing the mouse nasal cavity with PBS were collected in order to confirm systemic immune responses and mucosal immune responses.

According to the same ELISA method as described in Example 6-2, IgG in the plasma and antigen-specific secretory IgA in the nasal wash were measured.

As a result, it was shown that the mean value of antigen-specific IgG titers in the plasma of the group treated with the OVA/CpG/D-PTD 13 mixture (obtained by mixing at a molar ratio of 1:1:30 or 1:3:30) was higher than that in the group treated with the OVA/D-PTD 13 mixture (obtained by mixing at a molar ratio of 1:30) (FIG. 17).

In addition, it was shown that the secretion of antigen-specific secretory IgG in the nasal wash was higher in the group treated with the OVA/CpG/D-PTD 13 mixture (a molar ratio of 1:1:30, 1:3:30 or 1:6:30) than in the group treated with the OVA/D-PTD 13 mixture (a molar ratio of 1:30) (FIG. 18).

Example 7

Delivery of Target Substance into Brain by TCTP-PTD 13 and its Variants

The endothelial cells of brain capillaries have a tight junction therebetween, and thus have high selective permeability, and the tight junction is known as the blood-brain barrier. The blood-brain barrier serves to protect the brain, but makes it difficult to deliver a drug or other target substances into the brain.

In this Example, an experiment was performed to confirm that the TCTP-PTD peptide of the present invention delivers a drug into the brain.

In the experiment, the peptide [D-Leu-4-OB3] (Ser-Cys-Ser-D-Leu-Pro-Gln-Thr) synthesized based on the effective domain of leptin was used. Leptin is a peptide hormone that acts on hypothalamus and is involved in a variety of human body functions, including food intake, appetite regulation, body weight and fat regulation, energy balance regulation, glucose homeostasis, neuroendocrine function, immunity, metabolic function, etc. Leptin is produced by obesity gene (ob) and synthesized mainly in adipocytes and secreted. It is known that, when leptin is administered to obese animal models, it effectively reduces food intake and increases energy expenditure to thereby treat obesity. Using the body weight reduction and appetite inhibition functions of leptin, an attempt has been made to develop agents for treating diseases such as obesity, metabolic abnormalities or neuroendocrine abnormalities. Leptin has been administered mainly by injection. The effective domain exhibiting the major activity of leptin is known, and based on the effective domain, the synthetic peptide sequence OB3 (Ser-Cys-Ser-Leu-Pro-Gln-Thr) and the [D-Leu-4]-OB3 peptide obtained by substituting Leu at position 4 of the OB3 sequence with D-Leu to enhance the effect were developed (OZHAVS-KAYA-ARENA et al, 2000).

7-1: Preparation of TCTP-PTD 13-[D-Leu-4]-OB3

A peptide (SEQ ID NO: 124) comprising [D-Leu-4]-OB3 linked to L-PTD 13 or D-PTD 13 by a GG linker was designed. Furthermore, peptides (SEQ ID NO: 125, SEQ ID NO: 126 and SEQ ID NO: 127, respectively) comprising [D-Leu-4]-OB3 linked to each of D-TCTP-PTD 13M1, D-TCTP-PTD 13M2 or D-TCTP-PTD 13M3 by a GG linker were designed. The peptides were synthesized with a purity of 90% or higher by Peptron Inc.

7-2: Examination of Body Weight-Reducing Effect 4-week-old male ICR mice were used as experimental animals and divided into the following groups, each consisting of 7 animals: PBS, [D-Leu-4]-OB3, L-PTD 134D-Leu-41-OB3, and D-PTD 134D-Leu-41-OB3 groups. Each of [D-Leu-4]-OB3, L-PTD 134D-Leu-41-OB3 and D-PTD 13-[D-Leu-4]-OB3 was administered intranasally to each mouse at a dose of 2 mg/kg once each day for 10 days at a uniform time point, while a change in the body weight of each of the experimental animals was measured.

FIG. 19 shows the change of body weight, calculated relative to the initial body weight taken as 100%, and FIG. 20 shows the results of comparing the body weight after 10 days of administration. The rate of increase in body weight for 10 days was lower in the group administered with L-PTD 134D-Leu-41-OB3 or D-PTD 134D-Leu-41-OB3 than in the group administered with PBS or OB3 (FIG. 19). In addition, after 10 days, it was shown that the body weight of the group administered with L-PTD 13-[D-Leu-4]-OB3 or D-PTD 134D-Leu-41-OB3 decreased compared to that of the group administered with PBS or OB3 (FIG. 20). This suggests that, when [D-Leu-4]-OB3 is delivered into the brain through intranasal administration by TCTP-PTD, it exhibits a body weight-reducing effect.

7-3: Examination of Appetite-Inhibiting Effect

In order to examine whether or not the body weight-reducing effect confirmed in Example 7-2 has a connection with a decrease in food intake, PBS, [D-Leu-4]-OB3, L-PTD 13-[D-Leu-4]-OB3 or D-PTD 13-[D-Leu-4]-OB3 was administered intranasally at a dose of 2 mg/kg, and the food intake was measured everyday for 10 days.

As a result, it was shown that the cumulative food intake (g/mouse) decreased continuously in the group administered with L-PTD 134D-Leu-41-OB3 or D-PTD 134D-Leu-41-OB3 compared to the group administered with PBS (FIG. 21), and the total food intake after 10 days of administration also decreased in the group administered with L-PTD 13-[D-Leu-4]-OB3 or D-PTD 134D-Leu-41-OB3 (FIG. 22). This suggests that the TCTP-PTD administered intranasally delivered [D-Leu-4]-OB3 into the brain to thereby exhibit an appetite inhibiting effect to thereby the food intake.

Taking the results of Examples 7-2 and 7-3 together, it could be seen that the L-form and D-form of TCTP-PTD 13 all delivered [D-Leu-4]-OB3 into the brain through intranasal administration to exhibit body weight-reducing and appetite-inhibiting effects, and particularly, D-PTD 13 showed better effects than L-PTD 13.

7-4: Examination of the Ability of TCTP-PTD Variants to Deliver Target Substance into Brain Next, the ability to deliver the target substance into the brain was examined for the D-form peptides of SEQ ID NOs: 22, 24 and 18, which are the TCTP-PTD 13 variants confirmed to have the effect of delivering the target substance into the brain. According to the same method as described in Examples 7-2 and 7-3, [D-Leu-4]OB3 was linked to each of D-PTD 13 and its three variants and administered intranasally to the mice, and then changes in the body weight and the food intake were measured.

Each substance was administered intranasally to the mice at a dose of 2 mg/kg for 10 days, and changes in the body weight and the food intake were measured. As a result, it was shown that the all complex of [D-Leu-4]OB3 and TCTP-PTD had a significantly better effect than [D-Leu-4]OB3 alone on the reduction in body weight and food intake (FIGS. 23 and 24). In addition, the effects of the TCTP-PTD peptides of SEQ ID NO: 24 and SEQ ID NO: 18 were better than that of D-PTD 13, and the group treated with the TCTP-PTD of SEQ ID NO: 24 showed the greatest reductions in body weight and food intake.

Example 8

Preparation of Nasal Insulin Formulations Based on TCTP-PTD 8-1: Design of Nasal Insulin Formulation In order to develop a formulation containing TCTP-PTD as a nasal insulin carrier, the TCTP-PTD of SEQ ID NO: 24 was prepared with high purity (>95%) by A & PEP Co., Ltd., and the N-terminus and C-terminus of the synthesized peptide were modified by acetylation and amidation, respectively.

The isoelectric point of insulin is about pH 5.3, and the solubility thereof decreases at a pH near the isoelectric point. In view of the solubility of insulin and the average pH 6.3 in the nasal mucosal membrane, the pH of basic buffer (10 mM phosphate buffer (PB)) was set at 6.4-7. In order to inhibit aggregate formation in an insulin/PTD mixture and enhance storage stability, nasal insulin formulations were designed based on protein stabilizer (sucrose)+protein aggregation suppressor (arginine)+surfactant (Poloxamer 188)+antioxidant (methionine) (Table 3).

TABLE 3

| Formulation | Insulin (mM) | TCTP-PTD (mM) | Diluent | Aggregation Suppressor | Surfactant | Antioxidant | Buffer |
|---|---|---|---|---|---|---|---|
| 3-1 | 0.1 | 0.2 | 1% sucrose | 100 mM Arginine | Poloxamer 188 (0.5 mg/ml) | 1 mM methionine | 10 mM PB, pH 6.4 |
| 3-2 | 0.1 | 0.2 | 1% sucrose | — | Poloxamer 188 (0.5 mg/ml) | 1 mM methionine | 10 mM PB, pH 6.4 |
| 3-3 | 0.1 | 0.25 | 1% sucrose | — | Poloxamer 188 (0.1 mg/ml) | 1 mM methionine | 10 mM PB, pH 6.4 |
| 3-4 | 0.1 | 0.3 | 1% sucrose | — | Poloxamer 188 (0.1 mg/ml) | 1 mM methionine | 10 mM PB, pH 6.4 |
| 3-5 | 0.1 | 0.25 | 1% sucrose | — | Poloxamer 188 (0.1 mg/ml) | 1 mM methionine | 10 mM PB, pH 7.0 |
| 3-6 | 0.1 | 0.2 | 0.5% sucrose | — | Poloxamer 188 (0.5 mg/ml) | 1 mM methionine | 10 mM PB, pH 6.4 |
| 3-7 | 0.1 | 0.2 | 0.25% sucrose | — | Poloxamer 188 (0.5 mg/ml) | 1 mM methionine | 10 mM PB, pH 6.4 |
| 3-8 | 0.1 | 0.2 | 0.5% sucrose | — | Poloxamer 188 (0.5 mg/ml) | 1 mM methionine | 10 mM PB, pH 7.0 |

PB: phosphate buffer 8-2: Evaluation of Pharmacodynamic Profile of Nasal Insulin Formulation After design of the nasal insulin formulations, evaluation of the pharmacodynamic profile of each nasal insulin formulation was performed in normal white rats. Specifically, male white Wistar rats weighing 165-200 g were used as experimental animals. For accuracy of evaluation, the mice were fasted overnight, and then white rats having a blood glucose level of 90-120 mg/dL in the fasted state were used in the experiment. To calculate PA (pharmacological availability), the initial blood glucose level was taken as 100%. To administer the nasal insulation formulations, the mice were anesthetized by intraperitoneal administration of the anesthetic sodium pentobarbital (dose: 65 mg/kg). Each of the insulin formulation (insulin dose: 1 IU/kg) was administered intranasally to the anesthetized rats, and then a change in the blood glucose level was examined for 3 hours. The AAC of each nasal insulation formulation was calculated, and a superior insulin formulation was selected. The PA of the nasal insulin formulation relative to subcutaneous insulin injection (100%) was calculated, and as a result, the relative PA of the group administered with each of formulation 3-3 and formulation 3-5 was about 40% or higher, which was higher than those of other insulin formulations (FIG. 25 and Table 4).

TABLE 4

| Formulation | Route of Administration | Insulin dose (IU/kg) | AAC 0-180 min | PA % |
|---|---|---|---|---|
| Control (Free insulin, s.c) | Subcutaneous (s.c) | 0.5 | 2560 | 100 |
| 3-1 | Nasal | 1 | 2804.69 ± 492.69 | 24.10 ± 4.23 |
| 3-2 | Nasal | 1 | 2303.26 ± 418.53 | 19.79 ± 3.60 |
| 3-3 | Nasal | 1 | 5357.90 ± 545.68 | 46.05 ± 4.69 |
| 3-4 | Nasal | 1 | 4293.23 ± 223.27 | 36.90 ± 1.92 |
| 3-5 | Nasal | 1 | 4975.66 ± 405.06 | 42.76 ± 3.48 |
| 3-6 | Nasal | 1 | 3788.50 ± 542.64 | 32.56 ± 4.66 |
| 3-7 | Nasal | 1 | 3892.14 ± 427.50 | 33.45 ± 3.67 |
| 3-8 | Nasal | 1 | 4288.10 ± 390.21 | 36.85 ± 3.35 |

AAC: the area above the blood glucose level-time curve from 0 to 180 min
PA (pharmacological availability) was calculated using the following equation: PA % = $(AAC_{nasal} \times Dose_{s.c})/(AUC_{s.c} \times Dose_{nasal}) \times 100\%$

8-3: Evaluation of Single-Dose Toxicity of Nasal Insulin Formulation

In order to examine whether or not formulation 3-3 and formulation 3-5, which showed an excellent ability to deliver insulin, would cause damage to the nasal mucosal membrane upon intranasal administration, the nasal cavity was washed with 1 ml of PBS at 15 minutes after insulin administration. Then, in the basal wash, LDH (lactate dehydrogenase), which is released when cells are destroyed, was measured, thereby evaluating whether or not the nasal mucosal membrane was damaged. As a positive control, 5% sodium taurodeoxycholate was administered intranasally to the white rats.

As a result, the LDH level in the positive control group significantly increased compared to that in the untreated group (P>0.05; FIG. 26). However, all the groups administered with the nasal insulin formulations of the present invention showed low LDL levels similar to that of the untreated group (negative control group). This suggests that the single dose of the nasal insulation formulation has insignificant toxicity.

8-4: Evaluation of Pharmacokinetic Profiles of Insulin Formulations

In this Example, the BA (bioavailability) values of the two nasal insulin formulations (formulations 3-3 and 3-5), which showed excellent PA in the pharmacodynamic evaluation, were measured. Evaluation of the pharmacokinetic profiles was performed in the same white rats as described above, and each of the nasal insulin formulations was administered intranasally to the anesthetized white rats. Then, blood was collected from the mice at varying time points, and the concentration of insulin in the plasma was measured.

Insulin was administered to the white rats at a dose of 1 IU/kg, and BA was compared with that of the group injected subcutaneously with insulin (0.25 IU/kg). When the BA of the group injected subcutaneously with insulin was taken as 100%, the relative BA values of the free insulin group (insulin dose: 5 IU/kg) administered intranasally with insulin alone and the free insulin+PTD group administered with a simple mixture of insulin solution and PTD were calculated to be 3.3% and 38.7%, respectively. However, the relative BA values of the group administered with nasal insulin formulation 3-3 and the group administration with formulation 3-5 were calculated to be 60.7% and 45.9%, respectively (FIG. 27 and Table 5).

TABLE 5

| Foundation | Insulin dose (IU/kg) | Route of administration | AUC 0-180 min | BA % |
|---|---|---|---|---|
| Free insulin, nasal | 5 IU/kg | Nasal | 1574.62 ± 177.06 | 3.34 ± 0.38 |
| Free insulin, s.c | 0.25 IU/kg | Subcutaneous (s.c) | 2356.41 ± 106.19 | 100 |
| Free insulin + PTD | 1 IU/kg | Nasal | 3643.49 ± 425.36 | 38.66 ± 4.51 |
| 3-3 | 1 IU/kg | Nasal | 5722.18 ± 705.14 | 60.71 ± 7.48 |
| 3-5 | 1 IU/kg | Nasal | 4322.47 ± 576.51 | 45.86 ± 6.12 |

AUC: the area under the plasma insulin concentration-time curve from time 0 to 180 min.
BA (bioavailability) was calculated using the following equation: BA % = $(AUC_{nasal} \times Dose_{s.c})/(AUC_{s.c} \times Dose_{nasal}) \times 100\%$
Thus, the relative BA values obtained by nasal insulin formulations 3-3 and 3-5 increased 1.6-fold and 1,3-fold, respectively.

8-5: Evaluation of Pharmacodynamic Profiles of Nasal Insulin Formulations in Type 1 Diabetic Models Alloxan was injected intraperitoneally to experimental white rats to induce type 1 diabetes. One week after alloxan administration, white rats having a blood glucose level of 230-300 mg/dL were used as experimental animals. Each of the nasal insulin formulations was administered to the anesthetized diabetic rats, and then the blood glucose level was monitored for 4 hours. Each formulation was administered such that the insulin dose was 2 IU/kg of diabetic rat. The PA value was compared with that of the group injected subcutaneously with insulin (1 IU/kg).

The PA of the nasal insulin formulation relative to that of the subcutaneous insulin injection (100%) was calculated, and as a result, the relative PA of the free insulin group administered intranasally with insulin alone was as low as 4%, whereas the relative PA of the group administered with formulation 3-3 based on PTD was 49.3%, and the relative PA of the group administered with formulation 3-5 was 37.5% (FIG. 28 and Table 6).

TABLE 6

| Formulation | Route of administration | Insulin dose (IU/kg) | AAC 0-240 min | PA % |
|---|---|---|---|---|
| Free insulin, nasal | Nasal | 2 | 2156.65 ± 1070.68 | 4.01 ± 1.99 |
| Free insulin, s.c | Subcutaneous (s.c) | 1 | 26897.33 ± 772.31 | 100 |
| 3-3 | Nasal | 2 | 26537.27 ± 1455.91 | 49.33 ± 2.71 |
| 3-5 | Nasal | 2 | 20181.39 ± 3035.38 | 37.52 ± 5.64 |

AAC: the area above the blood glucose level-time curve from time 0 to 240 min.
PA (pharmacological availability) was calculated using the following equation: PA % = (AAC$_{nasal}$ × Dose$_{s.c}$)/(AAC$_{s.c}$ × Dose$_{nasal}$) × 100%

8-6: Evaluation of Repeated-Dose Toxicity of Nasal Insulin Formulations

Each of nasal insulin formulations 3-3 and 3-5, which showed an excellent ability to deliver insulin upon intranasal administration, was administered intranasally to male ICR mice once a day for 10 days (insulin dose: 2 IU/kg). Then, the nasal mucosal membrane and the blood were collected, and whether the nasal mucosal membrane was damaged and hematologic Indices were analyzed.

The nasal mucosal tissue was observed and evaluated, and as a result, it was observed that the nasal mucosal tissue in the positive control group (5% sodium taurodeoxycholate) was destroyed, but there was no significant histopathological change in the case of the two nasal insulin formulations (FIG. 29). In addition, the mice were sacrificed at 10 days after repeated intranasal administration, and evaluated in the same manner as the single-dose toxicity evaluation (LDH measurement), and as a result, the control group (0.9% NaCl) and the group administered intranasally with the insulin formulation showed no clear toxicity even after repeated administration (FIG. 30).

Next, for serum biological examination, blood was collected from the experimental animals on 10 days after repeated intranasal administration. The collected blood was centrifuged to isolate serum, and the isolated serum was analyzed using an automatic serum analyzer. ALT (alanine transaminase) and AST (aspartate transaminase) levels, which are liver damage indices, did not significantly differ between the control group (0.9% NaCl) and all the groups administered with the nasal insulin formulations. Furthermore, BUN (blood urea nitrogen) and CRE (creatinine) levels, which are renal damage indices, did not significantly differ between the control group (0.9% NaCl) and all the groups administered with the nasal insulin formulations (FIG. 31). This suggests that no toxicity is observed when the nasal insulin formulation is administered for a short period.

In addition, from the experimental animals that received administration of the nasal insulin formulations for 10 days, the brain, heart, lung, kidney, liver and spleen extracted. Each of the extracted organs was fixed in 10% formalin solution. From the organ tissue, paraffin sections were prepared, and then stained with H&E (Hematoxylin and Eosin). Histopathological examination of the stained tissues was performed using an optical microscope. As a result, there was no significant pathological difference between the control group (0.9% NaCl) and the groups administered with the nasal insulin formulations (FIG. 32). Taking the above results together, it can be seen that, when the two nasal insulin formulations are delivered into the nasal cavity under the experimental conditions, they do not induce toxicological changes in the nasal tissue and major tissues.

The invention claimed is:

1. A composition comprising a peptide consisting of the following amino acid sequence and a target substance, wherein the peptide is an active ingredient for delivering the target substance into living tissue or blood:
R1-R2-R3-R4-R5-R6-R7-R8-R9-R10
wherein
R1 is M,
R2 is I,
R3 is I,
R4 is F,
R5 is R,
R6 is L,
R7 is L, P, H or A,
R8 is I, L, P, H or A,
R9 is S, E or Y, and
R10 is H, K, R, L or P; wherein optionally a peptide selected from the group consisting of a dipeptide, tripeptide or tetrapeptide of K is attached to R10.

2. A composition comprising a peptide, wherein the peptide consists of one of the amino acid sequences of SEQ ID NOs: 1, 12, 18, 22, 24, 25, 26, 128, 129, 130, 131, 132, 133 or 134; and
a target substance,
wherein the peptide is an active ingredient for delivering a target substance into living tissue or blood.

3. The composition of claim 1, wherein the peptide consists of one of the amino acid sequences of SEQ ID NOs: 12, 18, 22, or 24.

4. The composition of claim 1 or claim 2, wherein the peptide is a D-form, or racemic peptide.

5. The composition of claim 1 or claim 2, wherein the target substance is one or more of a chemical compound, a protein, a glycoprotein, a peptide, a nucleotide, a nucleic acid molecule, a carbohydrate, a lipid, a glycolipid, a natural product, a semi-synthetic drug, a nanoparticle, a liposome, a drug, a lipid-based formulation, a virus, a vaccine, a quantum dot, or a fluorochrome.

6. The composition of claim 5, wherein the drug is one or more of a chemical drug, biodrug, a nucleic acid drug, a peptide drug, a protein drug, a natural product, a semi-synthetic drug, a lipid drug, an enzyme, a regulatory factor, a hormone, a growth factor, a contrast agent, an antibody.

7. The composition of claim 1 or claim 2, wherein the target substance is insulin.

8. The composition of claim 1 or claim 2, wherein the peptide delivers the target substance through a mucous membrane or the skin.

9. The composition of claim 1 or claim 2, wherein the target substance is exendin-4.

10. The composition of claim 1 or claim 2, wherein the peptide delivers the target substance into a hair follicle.

11. The composition of claim 10, wherein the target substance is one or more of a hair growth-promoting drug, a hair growth-inhibiting drug, an antibiotic, and an anti-inflammatory drug.

12. The composition of claim 1 or claim 2, wherein the target substance is a vaccine.

13. The composition of claim 1 or claim 2, wherein the target substance is a drug that is delivered to a brain.

14. The composition of claim 13, wherein the drug is insulin, exendin-4, leptin or [D-Leu-4]-OB3.

15. The composition of claim 13, wherein the target substance is the drug, and wherein the drug is for prevention or treatment of one or more of diabetes, obesity, metabolic disease, dementia, osteoporosis, Alzheimer's disease, Parkinson's disease, stroke, central nervous disease, and peripheral nervous disease.

16. The composition of claim 1, wherein the peptide consists of the amino acid sequence of SEQ ID NO: 24.

17. A complex, comprising:
a peptide consisting of any one amino acid sequence selected from the group consisting of SEQ ID NOs: 1, 12, 18, 22, 24, 25, 26, 128, 129, 130, 131, 132, 133 and 134; and
a target substance.

18. The complex of claim 17, wherein the complex is obtained by mixing the peptide and the target substance, or conjugating the peptide and the target substance with a linker or a disulfide bond.

19. A formulation comprising:
a peptide consisting of any one of the amino acid sequences of SEQ ID NOs: 1, 12, 18, 22, 24, 25, 26, 128, 129, 130, 131, 132, 133 and 134; and
insulin.

20. The formulation of claim 19, further comprising sucrose, a poloxamer, or methionine.

21. A kit comprising:
a peptide consisting of one the amino acid sequences set forth as SEQ ID NOs: 1, 12, 18, 22, 24, 25, 26, 128, 129, 130, 131, 132, 133 and 134 and
b) a target substance.

22. A method for delivering a target substance into living tissue or blood, comprising
administering a pharmaceutically effective amount of a complex, wherein the complex comprises a) a peptide consisting of the amino acid sequence of one of SEQ ID NOs: 18, 22, and 24, 27; and b) a target substance, wherein the complex is administered to a subject in need thereof, thereby delivering the target substance into living tissue or blood in the subject.

23. The method of claim 22, wherein the complex is obtained by mixing the peptide and the target substance, or the peptide and the target substance are linked and conjugated by a linker or a disulfide bond.

24. The method of claim 22, wherein the target substance is vaccine.

25. The method of claim 22, wherein the target substance is delivered to a brain.

* * * * *

SEQUENCE LISTING

```
<160> NUMBER OF SEQ ID NOS: 134

<210> SEQ ID NO 1
<211> LENGTH: 12
<212> TYPE: PRT
<213> ORGANISM: Artificial Sequence
<220> FEATURE:
<223> OTHER INFORMATION: PTD #1

<400> SEQUENCE: 1

Leu Ile Ile Phe Arg Ala Leu Ile Ser His Lys Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: PTD #2

<400> SEQUENCE: 2

Met Ala Leu Glu Lys Met Ala Leu Glu Lys Lys Lys
1               5                   10

<210> SEQ ID NO 3
<211> LENGTH: 12
```

<212> TYPE: PRT
<213> ORGANISM: Artificial Sequence
<220> FEATURE:
<223> OTHER INFORMATION: PTD #3

<400> SEQUENCE: 3

Pro Ile Ile Phe Arg Ile Ala Ala Tyr His Lys Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: PTD #4

<400> SEQUENCE: 4

Met Ala Ala Phe Arg Ala Ala Ala Tyr His Lys Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: PTD #5

<400> SEQUENCE: 5

Met Ala Ala Phe Arg Ile Ala Ala Tyr His Lys Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: PTD #6

<400> SEQUENCE: 6

Met Ile Ala Ala Arg Ile Ala Ala Tyr His Lys Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: PTD #7

<400> SEQUENCE: 7

Met Ala Ala Phe Arg Pro Pro Pro Tyr His Lys Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: PTD #8

<400> SEQUENCE: 8

Met Ala Ala Phe Arg His His His Tyr His Lys Lys
1               5                   10

<210> SEQ ID NO 9
<211> LENGTH: 12
<212> TYPE: PRT

```
<213> ORGANISM: Artificial Sequence
<220> FEATURE:
<223> OTHER INFORMATION: PTD #9

<400> SEQUENCE: 9

Met Leu Leu Phe Arg Leu Ala Ala Tyr Lys Lys Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: PTD #10

<400> SEQUENCE: 10

Met Leu Leu Phe Arg Ile Ala Ala Tyr His Lys Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: PTD #11

<400> SEQUENCE: 11

Met Ile Leu Leu Arg Ile Ala Ala Tyr His Lys Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: PTD #12

<400> SEQUENCE: 12

Met Ile Ile Phe Arg Leu Ala Ala Tyr His Lys Lys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: PTD #13

<400> SEQUENCE: 13

Met Pro Pro Phe Arg Leu Ala Ala Tyr Arg Lys Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: PTD #14

<400> SEQUENCE: 14

Met Ile Pro Pro Arg Leu Ala Ala Tyr His Lys Lys
1               5                   10

<210> SEQ ID NO 15
<211> LENGTH: 12
<212> TYPE: PRT
<213> ORGANISM: Artificial Sequence
```

<220> FEATURE:
<223> OTHER INFORMATION: PTD #15

<400> SEQUENCE: 15

Met Ile Ile Phe Arg Pro Pro Ala Tyr His Lys Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: PTD #16

<400> SEQUENCE: 16

Met Ile Ile Phe Arg Ile Pro Pro Tyr His Lys Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: PTD #17

<400> SEQUENCE: 17

Met Ile Ile Phe Arg Ile Ala Ala Tyr Pro Lys Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: PTD #18

<400> SEQUENCE: 18

Met Ile Ile Phe Arg Leu Leu Ala Tyr His Lys Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: PTD #19

<400> SEQUENCE: 19

Met Ile Ile Phe Arg Ile Ala Leu Tyr Leu Lys Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: PTD #20

<400> SEQUENCE: 20

Met Pro Pro Pro Arg Leu Ala Ala Tyr His Lys Lys
1               5                   10

<210> SEQ ID NO 21
<211> LENGTH: 12
<212> TYPE: PRT
<213> ORGANISM: Artificial Sequence
<220> FEATURE:

<223> OTHER INFORMATION: PTD #21

<400> SEQUENCE: 21

Met His His His Arg Leu Ala Ala Tyr His Lys Lys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: PTD #22

<400> SEQUENCE: 22

Met Ile Ile Phe Arg Leu Leu Ile Ser His Lys Lys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: PTD #23

<400> SEQUENCE: 23

Leu Ile Ile Phe Arg Leu Leu Ile Ser His Lys Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: PTD #24

<400> SEQUENCE: 24

Met Ile Ile Phe Arg Leu Leu Ala Ser His Lys Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: PTD #25

<400> SEQUENCE: 25

Met Ile Ile Phe Arg Leu Leu Ala Tyr His Lys Lys Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: PTD #26

<400> SEQUENCE: 26

Met Ile Ile Phe Arg Leu Leu Ala Tyr His Lys Lys Lys Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: PTD #27

```
<400> SEQUENCE: 27

Met Ile Ile Phe Arg Ala Leu Ile Ser His Lys Lys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: PTD #28

<400> SEQUENCE: 28

Met Ile Ile Tyr Arg Asp Leu Ile Ser Lys Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: PTD #29

<400> SEQUENCE: 29

Met Ile Ile Tyr Arg Asp Lys Lys Ser His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: PTD #30

<400> SEQUENCE: 30

Met Ile Ile Phe Arg Asp Leu Ile Ser His
1               5                   10

<210> SEQ ID NO 31
<211> LENGTH: 10
<212> TYPE: PRT
<213> ORGANISM: Artificial Sequence
<220> FEATURE:
<223> OTHER INFORMATION: PTD #31

<400> SEQUENCE: 31

Met Ile Ile Ser Arg Asp Leu Ile Ser His
1               5                   10

<210> SEQ ID NO 32
<211> LENGTH: 10
<212> TYPE: PRT
<213> ORGANISM: Artificial Sequence
<220> FEATURE:
<223> OTHER INFORMATION: PTD #32

<400> SEQUENCE: 32

Gln Ile Ile Ser Arg Asp Leu Ile Ser His
1               5                   10

<210> SEQ ID NO 33
<211> LENGTH: 10
<212> TYPE: PRT
<213> ORGANISM: Artificial Sequence
<220> FEATURE:
<223> OTHER INFORMATION: PTD #33
```

<400> SEQUENCE: 33

Cys Ile Ile Ser Arg Asp Leu Ile Ser His
1               5                   10

<210> SEQ ID NO 34
<211> LENGTH: 10
<212> TYPE: PRT
<213> ORGANISM: Artificial Sequence
<220> FEATURE:
<223> OTHER INFORMATION: PTD #34

<400> SEQUENCE: 34

Cys Ile Ile Ser Arg Asp Leu Ile Ser His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: PTD #35

<400> SEQUENCE: 35

Met Ile Ile Tyr Arg Ile Ala Ala Ser His Lys Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: PTD #36

<400> SEQUENCE: 36

Met Ile Ile Arg Arg Asp Leu Ile Ser Glu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: PTD #37

<400> SEQUENCE: 37

Met Ile Ile Tyr Arg Ala Glu Ile Ser His
1               5                   10

<210> SEQ ID NO 38
<211> LENGTH: 10
<212> TYPE: PRT
<213> ORGANISM: Artificial Sequence
<220> FEATURE:
<223> OTHER INFORMATION: PTD #38

<400> SEQUENCE: 38

Met Ile Ile Tyr Ala Arg Arg Ala Glu Glu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: PTD #39

<400> SEQUENCE: 39

Met Ile Ile Phe Arg Ile Ala Ala Ser His Lys Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: PTD #40

<400> SEQUENCE: 40

Met Ile Ile Phe Arg Ala Ala Ala Ser His Lys Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: PTD #41

<400> SEQUENCE: 41

Phe Ile Ile Phe Arg Ile Ala Ala Ser His Lys Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: PTD #42

<400> SEQUENCE: 42

Leu Ile Ile Phe Arg Ile Ala Ala Ser His Lys Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: PTD #43

<400> SEQUENCE: 43

Trp Ile Ile Phe Arg Ile Ala Ala Ser His Lys Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: PTD #44

<400> SEQUENCE: 44

Trp Ile Ile Phe Arg Ala Ala Ala Ser His Lys Lys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: PTD #45

<400> SEQUENCE: 45

Trp Ile Ile Phe Arg Ala Leu Ile Ser His Lys Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: PTD #46

<400> SEQUENCE: 46

Met Ile Ile Phe Arg Ile Ala Ala Tyr His Lys Lys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: PTD #47

<400> SEQUENCE: 47

Trp Ile Ile Phe Arg Ile Ala Ala Tyr His Lys Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: PTD #48

<400> SEQUENCE: 48

Met Ile Ile Phe Arg Ile Ala Ala Thr His Lys Lys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: PTD #49

<400> SEQUENCE: 49

Trp Ile Ile Phe Arg Ile Ala Ala Thr His Lys Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: PTD #50

<400> SEQUENCE: 50

Met Ile Ile Phe Lys Ile Ala Ala Ser His Lys Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: PTD #51

<400> SEQUENCE: 51

Trp Ile Ile Phe Lys Ile Ala Ala Ser His Lys Lys

```
1               5                   10
```

<210> SEQ ID NO 52
<211> LENGTH: 12
<212> TYPE: PRT
<213> ORGANISM: Artificial Sequence
<220> FEATURE:
<223> OTHER INFORMATION: PTD #52

<400> SEQUENCE: 52

```
Met Ile Ile Phe Ala Ile Ala Ala Ser His Lys Lys
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: PTD #53

<400> SEQUENCE: 53

```
Leu Ile Ile Phe Arg Ile Leu Ile Ser His Lys Lys
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: PTD #54

<400> SEQUENCE: 54

```
Met Ile Ile Phe Arg Ile Leu Ile Ser His Lys Lys
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: PTD #55

<400> SEQUENCE: 55

```
Leu Ile Ile Phe Arg Ile Leu Ile Ser His Arg Arg
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: PTD #56

<400> SEQUENCE: 56

```
Leu Ile Ile Phe Arg Ile Leu Ile Ser His His His
1               5                   10
```

<210> SEQ ID NO 57
<211> LENGTH: 11
<212> TYPE: PRT
<213> ORGANISM: Artificial Sequence
<220> FEATURE:
<223> OTHER INFORMATION: PTD #57

<400> SEQUENCE: 57

```
Leu Ile Ile Phe Arg Ile Leu Ile Ser His Lys
1               5                   10
```

<210> SEQ ID NO 58
<211> LENGTH: 11
<212> TYPE: PRT
<213> ORGANISM: Artificial Sequence
<220> FEATURE:
<223> OTHER INFORMATION: PTD #58

<400> SEQUENCE: 58

Leu Ile Ile Phe Arg Ile Leu Ile Ser His Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: PTD #59

<400> SEQUENCE: 59

Leu Ile Ile Phe Arg Ile Leu Ile Ser His
1               5                   10

<210> SEQ ID NO 60
<211> LENGTH: 12
<212> TYPE: PRT
<213> ORGANISM: Artificial Sequence
<220> FEATURE:
<223> OTHER INFORMATION: PTD #60

<400> SEQUENCE: 60

Leu Ile Ile Phe Ala Ile Ala Ala Ser His Lys Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: PTD #61

<400> SEQUENCE: 61

Leu Ile Ile Phe Ala Ile Leu Ile Ser His Lys Lys
1               5                   10

<210> SEQ ID NO 62
<211> LENGTH: 36
<212> TYPE: DNA
<213> ORGANISM: Artificial Sequence
<220> FEATURE:
<223> OTHER INFORMATION: DNA coding PTD #1

<400> SEQUENCE: 62
ctgattattt ttcgcgcgct gattagccat aaaaaa                             36

<210> SEQ ID NO 63
<211> LENGTH: 36
<212> TYPE: DNA
<213> ORGANISM: Artificial Sequence
<220> FEATURE:
<223> OTHER INFORMATION: DNA coding PTD #2

<400> SEQUENCE: 63
atggcgctgg agaaaatggc gctggagaaa aaaaaa                             36

<210> SEQ ID NO 64

<210> SEQ ID NO 64
<211> LENGTH: 36
<212> TYPE: DNA
<213> ORGANISM: Artificial Sequence
<220> FEATURE:
<223> OTHER INFORMATION: DNA coding PTD #3

<400> SEQUENCE: 64
cccattattt ttcgcattgc ggcgtatcat aaaaaa                    36

<210> SEQ ID NO 65
<211> LENGTH: 36
<212> TYPE: DNA
<213> ORGANISM: Artificial Sequence
<220> FEATURE:
<223> OTHER INFORMATION: DNA coding PTD #4

<400> SEQUENCE: 65
atggcggcgt ttcgcgcggc ggcgtatcat aaaaaa                    36

<210> SEQ ID NO 66
<211> LENGTH: 36
<212> TYPE: DNA
<213> ORGANISM: Artificial Sequence
<220> FEATURE:
<223> OTHER INFORMATION: DNA coding PTD #5

<400> SEQUENCE: 66
atggcggcgt ttcgcattgc ggcgtatcat aaaaaa                    36

<210> SEQ ID NO 67
<211> LENGTH: 36
<212> TYPE: DNA
<213> ORGANISM: Artificial Sequence
<220> FEATURE:
<223> OTHER INFORMATION: DNA coding PTD #6

<400> SEQUENCE: 67
atgattgcgg cgcgcattgc ggcgtatcat aaaaaa                    36

<210> SEQ ID NO 68
<211> LENGTH: 36
<212> TYPE: DNA
<213> ORGANISM: Artificial Sequence
<220> FEATURE:
<223> OTHER INFORMATION: DNA coding PTD #7

<400> SEQUENCE: 68
atggcggcgt ttcgcccccc ccctatcat aaaaaa                     36

<210> SEQ ID NO 69
<211> LENGTH: 36
<212> TYPE: DNA
<213> ORGANISM: Artificial Sequence
<220> FEATURE:
<223> OTHER INFORMATION: DNA coding PTD #8

<400> SEQUENCE: 69
atggcggcgt ttcgccatca tcattatcat aaaaaa                    36

<210> SEQ ID NO 70
<211> LENGTH: 36
<212> TYPE: DNA
<213> ORGANISM: Artificial Sequence
<220> FEATURE:
<223> OTHER INFORMATION: DNA coding PTD #9

<400> SEQUENCE: 70
atgctgctgt tcgcctggc ggcgtataaa aaaaaa            36

<210> SEQ ID NO 71
<211> LENGTH: 36
<212> TYPE: DNA
<213> ORGANISM: Artificial Sequence
<220> FEATURE:
<223> OTHER INFORMATION: DNA coding PTD #10

<400> SEQUENCE: 71
atgctgctgt tcgcattgc ggcgtatcat aaaaaa            36

<210> SEQ ID NO 72
<211> LENGTH: 36
<212> TYPE: DNA
<213> ORGANISM: Artificial Sequence
<220> FEATURE:
<223> OTHER INFORMATION: DNA coding PTD #11

<400> SEQUENCE: 72
atgattctgc tgcgcattgc ggcgtatcat aaaaaa            36

<210> SEQ ID NO 73
<211> LENGTH: 36
<212> TYPE: DNA
<213> ORGANISM: Artificial Sequence
<220> FEATURE:
<223> OTHER INFORMATION: DNA coding PTD #12

<400> SEQUENCE: 73
atgattattt tcgcctggc ggcgtatcat aaaaaa            36

<210> SEQ ID NO 74
<211> LENGTH: 36
<212> TYPE: DNA
<213> ORGANISM: Artificial Sequence
<220> FEATURE:
<223> OTHER INFORMATION: DNA coding PTD #13

<400> SEQUENCE: 74
atgcccccct tcgcctggc ggcgtatcgc aaaaaa            36

<210> SEQ ID NO 75
<211> LENGTH: 36
<212> TYPE: DNA
<213> ORGANISM: Artificial Sequence
<220> FEATURE:
<223> OTHER INFORMATION: DNA coding PTD #14

<400> SEQUENCE: 75
atgattcccc ccgcctggc ggcgtatcat aaaaaa            36

<210> SEQ ID NO 76
<211> LENGTH: 36
<212> TYPE: DNA
<213> ORGANISM: Artificial Sequence
<220> FEATURE:
<223> OTHER INFORMATION: DNA coding PTD #15

<400> SEQUENCE: 76
atgattattt tcgccccccc cgcgtatcat aaaaaa            36

<210> SEQ ID NO 77
<211> LENGTH: 36
<212> TYPE: DNA

<213> ORGANISM: Artificial Sequence
<220> FEATURE:
<223> OTHER INFORMATION: DNA coding PTD #16

<400> SEQUENCE: 77
atgattattt ttcgcattcc cccctatcat aaaaaa                      36

<210> SEQ ID NO 78
<211> LENGTH: 36
<212> TYPE: DNA
<213> ORGANISM: Artificial Sequence
<220> FEATURE:
<223> OTHER INFORMATION: DNA coding PTD #17

<400> SEQUENCE: 78
atgattattt ttcgcattgc ggcgtatccc aaaaaa                      36

<210> SEQ ID NO 79
<211> LENGTH: 36
<212> TYPE: DNA
<213> ORGANISM: Artificial Sequence
<220> FEATURE:
<223> OTHER INFORMATION: DNA coding PTD #18

<400> SEQUENCE: 79
atgattattt ttcgcctgct ggcgtatcat aaaaaa                      36

<210> SEQ ID NO 80
<211> LENGTH: 36
<212> TYPE: DNA
<213> ORGANISM: Artificial Sequence
<220> FEATURE:
<223> OTHER INFORMATION: DNA coding PTD #19

<400> SEQUENCE: 80
atgattattt ttcgcattgc gctgtatctg aaaaaa                      36

<210> SEQ ID NO 81
<211> LENGTH: 36
<212> TYPE: DNA
<213> ORGANISM: Artificial Sequence
<220> FEATURE:
<223> OTHER INFORMATION: DNA coding PTD #20

<400> SEQUENCE: 81
atgccccccc cccgcctggc ggcgtatcat aaaaaa                      36

<210> SEQ ID NO 82
<211> LENGTH: 36
<212> TYPE: DNA
<213> ORGANISM: Artificial Sequence
<220> FEATURE:
<223> OTHER INFORMATION: DNA coding PTD #21

<400> SEQUENCE: 82
atgcatcatc atcgcctggc ggcgtatcat aaaaaa                      36

<210> SEQ ID NO 83
<211> LENGTH: 36
<212> TYPE: DNA
<213> ORGANISM: Artificial Sequence
<220> FEATURE:
<223> OTHER INFORMATION: DNA coding PTD #22

<400> SEQUENCE: 83
atgattattt ttcgcctgct gattagccat aaaaaa                      36

<210> SEQ ID NO 84
<211> LENGTH: 36
<212> TYPE: DNA
<213> ORGANISM: Artificial Sequence
<220> FEATURE:
<223> OTHER INFORMATION: DNA coding PTD #23

<400> SEQUENCE: 84
ctgattattt ttcgcctgct gattagccat aaaaaa                                36

<210> SEQ ID NO 85
<211> LENGTH: 36
<212> TYPE: DNA
<213> ORGANISM: Artificial Sequence
<220> FEATURE:
<223> OTHER INFORMATION: DNA coding PTD #24

<400> SEQUENCE: 85
atgattattt ttcgcctgct ggcgagccat aaaaaa                                36

<210> SEQ ID NO 86
<211> LENGTH: 39
<212> TYPE: DNA
<213> ORGANISM: Artificial Sequence
<220> FEATURE:
<223> OTHER INFORMATION: DNA coding PTD #25

<400> SEQUENCE: 86
atgattattt ttcgcctgct ggcgtatcat aaaaaaaaa                             39

<210> SEQ ID NO 87
<211> LENGTH: 42
<212> TYPE: DNA
<213> ORGANISM: Artificial Sequence
<220> FEATURE:
<223> OTHER INFORMATION: DNA coding PTD #26

<400> SEQUENCE: 87
atgattattt ttcgcctgct ggcgtatcat aaaaaaaaaa aa                         42

<210> SEQ ID NO 88
<211> LENGTH: 36
<212> TYPE: DNA
<213> ORGANISM: Artificial Sequence
<220> FEATURE:
<223> OTHER INFORMATION: DNA coding PTD #27

<400> SEQUENCE: 88
atgattattt ttcgcgcgct gattagccat aaaaaa                                36

<210> SEQ ID NO 89
<211> LENGTH: 33
<212> TYPE: DNA
<213> ORGANISM: Artificial Sequence
<220> FEATURE:
<223> OTHER INFORMATION: DNA coding PTD #28

<400> SEQUENCE: 89
atgattattt accgcgatct gattagcaaa aaa                                   33

<210> SEQ ID NO 90
<211> LENGTH: 30
<212> TYPE: DNA
<213> ORGANISM: Artificial Sequence
<220> FEATURE:

<223> OTHER INFORMATION: DNA coding PTD #29

<400> SEQUENCE: 90
atgattattt accgcgataa aaaaagccat                                    30

<210> SEQ ID NO 91
<211> LENGTH: 30
<212> TYPE: DNA
<213> ORGANISM: Artificial Sequence
<220> FEATURE:
<223> OTHER INFORMATION: DNA sequence coding PTD #30

<400> SEQUENCE: 91
atgattattt ttcgcgatct gattagccat                                    30

<210> SEQ ID NO 92
<211> LENGTH: 30
<212> TYPE: DNA
<213> ORGANISM: Artificial Sequence
<220> FEATURE:
<223> OTHER INFORMATION: DNA sequence coding PTD #31

<400> SEQUENCE: 92
atgattatta gccgcgatct gattagccat                                    30

<210> SEQ ID NO 93
<211> LENGTH: 30
<212> TYPE: DNA
<213> ORGANISM: Artificial Sequence
<220> FEATURE:
<223> OTHER INFORMATION: DNA sequence coding PTD #32

<400> SEQUENCE: 93
caaattatta gccgcgatct gattagccat                                    30

<210> SEQ ID NO 94
<211> LENGTH: 30
<212> TYPE: DNA
<213> ORGANISM: Artificial Sequence
<220> FEATURE:
<223> OTHER INFORMATION: DNA sequence coding PTD #33

<400> SEQUENCE: 94
tgtattatta gccgcgatct gattagccat                                    30

<210> SEQ ID NO 95
<211> LENGTH: 36
<212> TYPE: DNA
<213> ORGANISM: Artificial Sequence
<220> FEATURE:
<223> OTHER INFORMATION: DNA sequence coding PTD #34

<400> SEQUENCE: 95
atgattattt atcgcgcgct gattagccat aaaaaa                             36

<210> SEQ ID NO 96
<211> LENGTH: 36
<212> TYPE: DNA
<213> ORGANISM: Artificial Sequence
<220> FEATURE:
<223> OTHER INFORMATION: DNA sequence coding PTD #35

<400> SEQUENCE: 96
atgattattt atcgcattgc ggcgagccat aaaaaa                             36

<210> SEQ ID NO 97
<211> LENGTH: 30
<212> TYPE: DNA
<213> ORGANISM: Artificial Sequence
<220> FEATURE:
<223> OTHER INFORMATION: DNA sequence coding PTD #36

<400> SEQUENCE: 97
atgattattc gccgcgatct gattagcgag                                    30

<210> SEQ ID NO 98
<211> LENGTH: 30
<212> TYPE: DNA
<213> ORGANISM: Artificial Sequence
<220> FEATURE:
<223> OTHER INFORMATION: DNA sequence coding PTD #37

<400> SEQUENCE: 98
atgattattt accgcgcgga gattagccat                                    30

<210> SEQ ID NO 99
<211> LENGTH: 30
<212> TYPE: DNA
<213> ORGANISM: Artificial Sequence
<220> FEATURE:
<223> OTHER INFORMATION: DNA sequence coding PTD #38

<400> SEQUENCE: 99
atgattattt acgcgcgccg cgcggaggag                                    30

<210> SEQ ID NO 100
<211> LENGTH: 36
<212> TYPE: DNA
<213> ORGANISM: Artificial Sequence
<220> FEATURE:
<223> OTHER INFORMATION: DNA sequence coding PTD #39

<400> SEQUENCE: 100
atgattattt ttcgcattgc ggcgagccat aaaaaa                             36

<210> SEQ ID NO 101
<211> LENGTH: 36
<212> TYPE: DNA
<213> ORGANISM: Artificial Sequence
<220> FEATURE:
<223> OTHER INFORMATION: DNA sequence coding PTD #40

<400> SEQUENCE: 101
atgattattt ttcgcgcggc ggcgagccat aaaaaa                             36

<210> SEQ ID NO 102
<211> LENGTH: 36
<212> TYPE: DNA
<213> ORGANISM: Artificial Sequence
<220> FEATURE:
<223> OTHER INFORMATION: DNA sequence coding PTD #41

<400> SEQUENCE: 102
tttattattt ttcgcattgc ggcgagccat aaaaaa                             36

<210> SEQ ID NO 103
<211> LENGTH: 36
<212> TYPE: DNA
<213> ORGANISM: Artificial Sequence
<220> FEATURE:
<223> OTHER INFORMATION: DNA sequence coding PTD #42

```
<400> SEQUENCE: 103
ctgattattt ttcgcattgc ggcgagccat aaaaaa                                    36

<210> SEQ ID NO 104
<211> LENGTH: 36
<212> TYPE: DNA
<213> ORGANISM: Artificial Sequence
<220> FEATURE:
<223> OTHER INFORMATION: DNA sequence coding PTD #43

<400> SEQUENCE: 104
tggattattt ttcgcattgc ggcgagccat aaaaaa                                    36

<210> SEQ ID NO 105
<211> LENGTH: 36
<212> TYPE: DNA
<213> ORGANISM: Artificial Sequence
<220> FEATURE:
<223> OTHER INFORMATION: DNA sequence coding PTD #44

<400> SEQUENCE: 105
tggattattt ttcgcgcggc ggcgagccat aaaaaa                                    36

<210> SEQ ID NO 106
<211> LENGTH: 36
<212> TYPE: DNA
<213> ORGANISM: Artificial Sequence
<220> FEATURE:
<223> OTHER INFORMATION: DNA sequence coding PTD #45

<400> SEQUENCE: 106
tggattattt ttcgcgcgct gattagccat aaaaaa                                    36

<210> SEQ ID NO 107
<211> LENGTH: 36
<212> TYPE: DNA
<213> ORGANISM: Artificial Sequence
<220> FEATURE:
<223> OTHER INFORMATION: DNA sequence coding PTD #46

<400> SEQUENCE: 107
atgattattt ttcgcattgc ggcgtatcat aaaaaa                                    36

<210> SEQ ID NO 108
<211> LENGTH: 36
<212> TYPE: DNA
<213> ORGANISM: Artificial Sequence
<220> FEATURE:
<223> OTHER INFORMATION: DNA sequence coding PTD #47

<400> SEQUENCE: 108
tggattattt ttcgcattgc ggcgtatcat aaaaaa                                    36

<210> SEQ ID NO 109
<211> LENGTH: 36
<212> TYPE: DNA
<213> ORGANISM: Artificial Sequence
<220> FEATURE:
<223> OTHER INFORMATION: DNA sequence coding PTD #48

<400> SEQUENCE: 109
atgattattt ttcgcattgc ggcgacccat aaaaaa                                    36

<210> SEQ ID NO 110
<211> LENGTH: 36
```

-continued

<212> TYPE: DNA
<213> ORGANISM: Artificial Sequence
<220> FEATURE:
<223> OTHER INFORMATION: DNA sequence coding PTD #49

<400> SEQUENCE: 110
tggattattt ttcgcattgc ggcgacccat aaaaaa                              36

<210> SEQ ID NO 111
<211> LENGTH: 36
<212> TYPE: DNA
<213> ORGANISM: Artificial Sequence
<220> FEATURE:
<223> OTHER INFORMATION: DNA sequence coding PTD #50

<400> SEQUENCE: 111
atgattattt ttaaaattgc ggcgagccat aaaaaa                              36

<210> SEQ ID NO 112
<211> LENGTH: 36
<212> TYPE: DNA
<213> ORGANISM: Artificial Sequence
<220> FEATURE:
<223> OTHER INFORMATION: DNA sequence coding PTD #51

<400> SEQUENCE: 112
tggattattt ttaaaattgc ggcgagccat aaaaaa                              36

<210> SEQ ID NO 113
<211> LENGTH: 36
<212> TYPE: DNA
<213> ORGANISM: Artificial Sequence
<220> FEATURE:
<223> OTHER INFORMATION: DNA sequence coding PTD #52

<400> SEQUENCE: 113
atgattattt ttgcgattgc ggcgagccat aaaaaa                              36

<210> SEQ ID NO 114
<211> LENGTH: 36
<212> TYPE: DNA
<213> ORGANISM: Artificial Sequence
<220> FEATURE:
<223> OTHER INFORMATION: DNA sequence coding PTD #53

<400> SEQUENCE: 114
ctgattattt ttcgcattct gattagccat aaaaaa                              36

<210> SEQ ID NO 115
<211> LENGTH: 36
<212> TYPE: DNA
<213> ORGANISM: Artificial Sequence
<220> FEATURE:
<223> OTHER INFORMATION: DNA sequence coding PTD #54

<400> SEQUENCE: 115
atgattattt ttcgcattct gattagccat aaaaaa                              36

<210> SEQ ID NO 116
<211> LENGTH: 36
<212> TYPE: DNA
<213> ORGANISM: Artificial Sequence
<220> FEATURE:
<223> OTHER INFORMATION: DNA sequence coding PTD #55

<400> SEQUENCE: 116

```
ctgattattt ttcgcattct gattagccat cgccgc                              36

<210> SEQ ID NO 117
<211> LENGTH: 36
<212> TYPE: DNA
<213> ORGANISM: Artificial Sequence
<220> FEATURE:
<223> OTHER INFORMATION: DNA sequence coding PTD #56

<400> SEQUENCE: 117
ctgattattt ttcgcattct gattagccat catcat                              36

<210> SEQ ID NO 118
<211> LENGTH: 33
<212> TYPE: DNA
<213> ORGANISM: Artificial Sequence
<220> FEATURE:
<223> OTHER INFORMATION: DNA sequence coding PTD #57

<400> SEQUENCE: 118
ctgattattt ttcgcattct gattagccat aaa                                 33

<210> SEQ ID NO 119
<211> LENGTH: 33
<212> TYPE: DNA
<213> ORGANISM: Artificial Sequence
<220> FEATURE:
<223> OTHER INFORMATION: DNA sequence coding PTD #58

<400> SEQUENCE: 119
ctgattattt ttcgcattct gattagccat cgc                                 33

<210> SEQ ID NO 120
<211> LENGTH: 30
<212> TYPE: DNA
<213> ORGANISM: Artificial Sequence
<220> FEATURE:
<223> OTHER INFORMATION: DNA sequence coding PTD #59

<400> SEQUENCE: 120
ctgattattt ttcgcattct gattagccat                                     30

<210> SEQ ID NO 121
<211> LENGTH: 36
<212> TYPE: DNA
<213> ORGANISM: Artificial Sequence
<220> FEATURE:
<223> OTHER INFORMATION: DNA sequence coding PTD #60

<400> SEQUENCE: 121
ctgattattt ttgcgattgc ggcgagccat aaaaaa                              36

<210> SEQ ID NO 122
<211> LENGTH: 36
<212> TYPE: DNA
<213> ORGANISM: Artificial Sequence
<220> FEATURE:
<223> OTHER INFORMATION: DNA sequence coding PTD #61

<400> SEQUENCE: 122
ctgattattt ttgcgattct gattagccat aaaaaa                              36

<210> SEQ ID NO 123
<211> LENGTH: 24
<212> TYPE: DNA
<213> ORGANISM: Artificial Sequence
```

<220> FEATURE:
<223> OTHER INFORMATION: CpG

<400> SEQUENCE: 123
tcgtcgtttt gtcgttttgt cgtt                                              24

<210> SEQ ID NO 124
<211> LENGTH: 21
<212> TYPE: PRT
<213> ORGANISM: Artificial Sequence
<220> FEATURE:
<223> OTHER INFORMATION: PTD #27-GG-[D-Leu-4]-OB3

<400> SEQUENCE: 124

Met Ile Ile Phe Arg Ala Leu Ile Ser His Lys Lys Gly Gly Ser Cys
1               5                   10                  15

Ser Leu Pro Gln Thr
            20

<210> SEQ ID NO 125
<211> LENGTH: 21
<212> TYPE: PRT
<213> ORGANISM: Artificial Sequence
<220> FEATURE:
<223> OTHER INFORMATION: PTD #22-GG-[D-Leu-4]-OB3

<400> SEQUENCE: 125

Met Ile Ile Phe Arg Leu Leu Ile Ser His Lys Lys Gly Gly Ser Cys
1               5                   10                  15

Ser Leu Pro Gln Thr
            20

<210> SEQ ID NO 126
<211> LENGTH: 21
<212> TYPE: PRT
<213> ORGANISM: Artificial Sequence
<220> FEATURE:
<223> OTHER INFORMATION: PTD #24-GG-[D-Leu-4]-OB3

<400> SEQUENCE: 126

Met Ile Ile Phe Arg Leu Leu Ala Ser His Lys Lys Gly Gly Ser Cys
1               5                   10                  15

Ser Leu Pro Gln Thr
            20

<210> SEQ ID NO 127
<211> LENGTH: 21
<212> TYPE: PRT
<213> ORGANISM: Artificial Sequence
<220> FEATURE:
<223> OTHER INFORMATION: PTD #18-GG-[D-Leu-4]-OB3

<400> SEQUENCE: 127

Met Ile Ile Phe Arg Leu Leu Ala Tyr His Lys Lys Gly Gly Ser Cys
1               5                   10                  15

Ser Leu Pro Gln Thr
            20

<210> SEQ ID NO 128
<211> LENGTH: 12
<212> TYPE: PRT
<213> ORGANISM: Artificial Sequence
<220> FEATURE:
<223> OTHER INFORMATION: PTD #128

```
<400> SEQUENCE: 128

Met Ile Ile Phe Arg Leu Ala Ala Ser His Lys Lys
1               5                   10

<210> SEQ ID NO 129
<211> LENGTH: 12
<212> TYPE: PRT
<213> ORGANISM: Artificial Sequence
<220> FEATURE:
<223> OTHER INFORMATION: PTD #129

<400> SEQUENCE: 129

Met Ile Ile Phe Arg Leu His Ala Ser His Lys Lys
1               5                   10

<210> SEQ ID NO 130
<211> LENGTH: 12
<212> TYPE: PRT
<213> ORGANISM: Artificial Sequence
<220> FEATURE:
<223> OTHER INFORMATION: PTD #130

<400> SEQUENCE: 130

Met Ile Ile Phe Arg Leu Leu Leu Ser His Lys Lys
1               5                   10

<210> SEQ ID NO 131
<211> LENGTH: 12
<212> TYPE: PRT
<213> ORGANISM: Artificial Sequence
<220> FEATURE:
<223> OTHER INFORMATION: PTD #131

<400> SEQUENCE: 131

Met Ile Ile Phe Arg Leu Leu His Ser His Lys Lys
1               5                   10

<210> SEQ ID NO 132
<211> LENGTH: 12
<212> TYPE: PRT
<213> ORGANISM: Artificial Sequence
<220> FEATURE:
<223> OTHER INFORMATION: PTD #132

<400> SEQUENCE: 132

Met Ile Ile Phe Arg Leu Leu Ala Glu His Lys Lys
1               5                   10

<210> SEQ ID NO 133
<211> LENGTH: 12
<212> TYPE: PRT
<213> ORGANISM: Artificial Sequence
<220> FEATURE:
<223> OTHER INFORMATION: PTD #133

<400> SEQUENCE: 133

Met Ile Ile Phe Arg Leu Leu Ala Ser Lys Lys Lys
1               5                   10

<210> SEQ ID NO 134
<211> LENGTH: 12
<212> TYPE: PRT
<213> ORGANISM: Artificial Sequence
<220> FEATURE:
<223> OTHER INFORMATION: PTD #134
```

```
<400> SEQUENCE: 134

Met Ile Ile Phe Arg Leu Leu Ala Ser Leu Lys Lys
1               5                   10
```